United States Patent
Lequette et al.

(10) Patent No.: US 10,485,591 B2
(45) Date of Patent: Nov. 26, 2019

(54) BONE ANCHORING SYSTEM, ASSOCIATED IMPLANT AND INSTRUMENTATION

(71) Applicant: LDR Medical, S.A.S., Sainte-Savine (FR)

(72) Inventors: Samuel Lequette, Pessac (FR); Emmanuel Bougere, Bordeaux (FR); Nicolas Bidegaimberry, Gradignan (FR); Aymeric Fresneau, Bordeaux (FR)

(73) Assignee: LDR Medical, S.A.S., Sainte-Savine (FR)

( * ) Notice: Subject to any disclaimer, the term of this patent is extended or adjusted under 35 U.S.C. 154(b) by 0 days.

(21) Appl. No.: 15/582,568

(22) Filed: Apr. 28, 2017

(65) Prior Publication Data

US 2017/0311997 A1    Nov. 2, 2017

(30) Foreign Application Priority Data

Apr. 28, 2016    (FR) .................... 16 53849

(51) Int. Cl.
*A61F 2/44* (2006.01)
*A61B 17/72* (2006.01)
(Continued)

(52) U.S. Cl.
CPC .......... *A61B 17/72* (2013.01); *A61B 17/7076* (2013.01); *A61B 17/844* (2013.01);
(Continued)

(58) Field of Classification Search
CPC .... A61F 2/44; A61F 2002/305; A61B 17/844; A61B 17/7076
See application file for complete search history.

(56) References Cited

U.S. PATENT DOCUMENTS 8,932,359 B2 * 1/2015 Brett ...................... A61F 2/442
                                                                623/17.16
2011/0196494 A1 8/2011 Yedlicka et al.
(Continued)

FOREIGN PATENT DOCUMENTS

FR          2954692 A1    7/2011
WO    WO-2010092893 A1    8/2010
(Continued)

OTHER PUBLICATIONS

"International Application Serial No. PCT/EP2017/060307, International Search Report dated Sep. 1, 2017", 4 pgs.
(Continued)

*Primary Examiner* — Bruce E Snow
(74) *Attorney, Agent, or Firm* — Schwegman Lundberg & Woessner, P.A.

(57) ABSTRACT

An anchoring system for the implantation of at least one anchoring device in at least one preferably bone tissue, the system is disclosed, with some embodiments comprising:
- at least one anchoring device comprising a curved body extending between an anterior end intended to penetrate without any deformation in the bone tissue and a posterior end intended to remain turned outward of the bone tissue,
- at least one guide extending along a longitudinal axis between a posterior end and an anterior end and comprising at least one guiding surface, substantially along the longitudinal axis, able to guide at least one anchoring device.

16 Claims, 31 Drawing Sheets

(51) Int. Cl.
  *A61F 2/46*     (2006.01)
  *A61B 17/70*    (2006.01)
  *A61B 17/84*    (2006.01)
  *A61F 2/30*         (2006.01)
  *A61B 17/04*        (2006.01)
  *A61B 17/86*        (2006.01)

(52) U.S. Cl.
  CPC ......... *A61F 2/4611* (2013.01); *A61B 17/0401* (2013.01); *A61B 2017/8655* (2013.01); *A61F 2002/30579* (2013.01); *A61F 2002/4623* (2013.01)

(56) References Cited

U.S. PATENT DOCUMENTS

2011/0230971 A1*  9/2011  Donner .................. A61B 17/70
                                                    623/17.16
2015/0127109 A1   5/2015  Brett

FOREIGN PATENT DOCUMENTS

| WO | WO-2011080535 A1 | 7/2011 |
| WO | WO-2012129205 A1 | 9/2012 |
| WO | WO-2013032716 A1 | 3/2013 |
| WO | WO-2017186966 A1 | 11/2017 |

OTHER PUBLICATIONS

"International Application Serial No. PCT/EP2017/060307, Written Opinion dated Sep. 1, 2017", 5 pgs.
"European Application Serial. No. 17725519.7, Response filed Jun. 17, 2019 to Office Action dated Dec. 5, 2019", 18 pgs.

\* cited by examiner

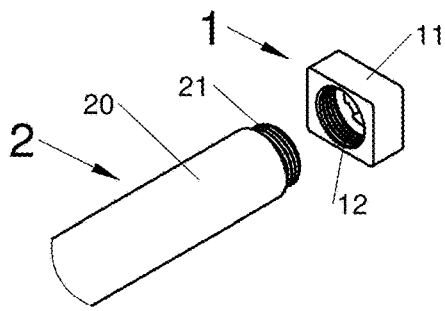
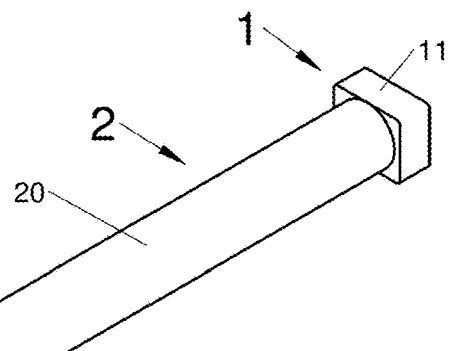
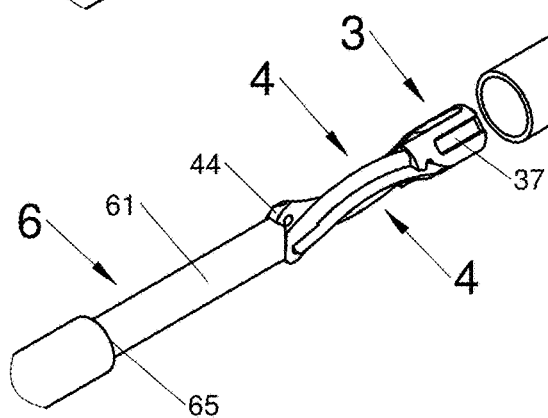
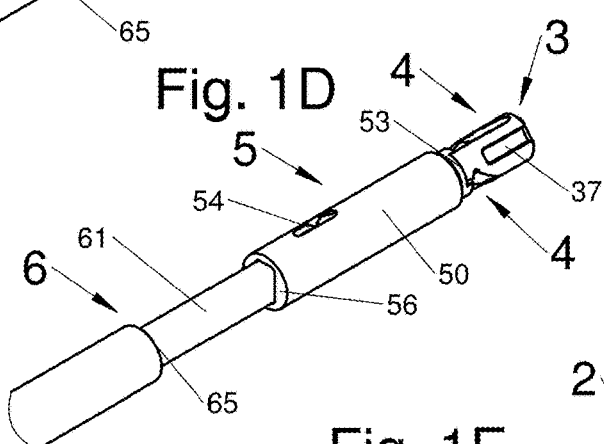
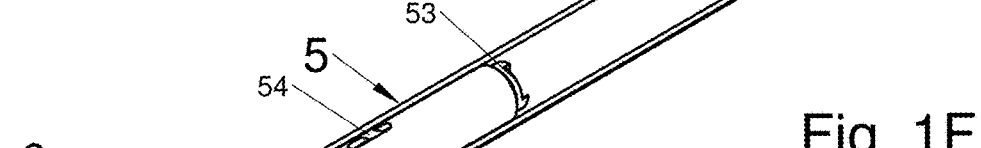
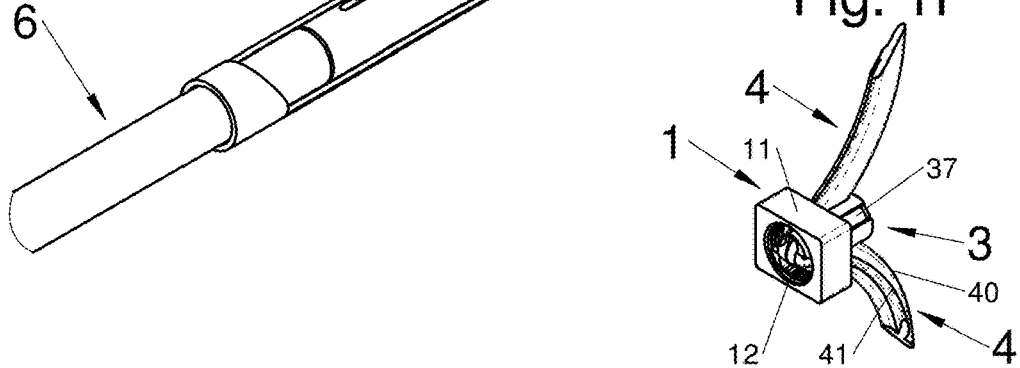

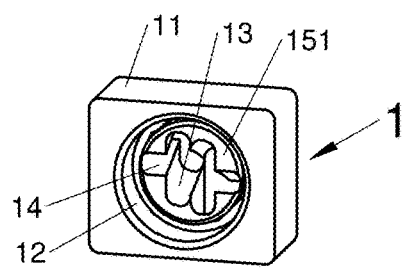
Fig. 3A
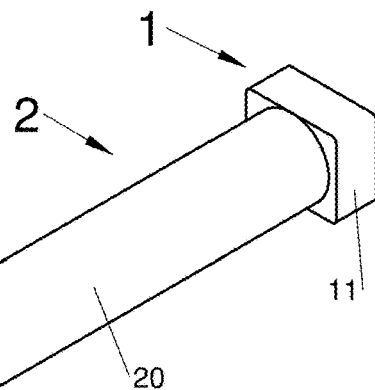
Fig. 3B
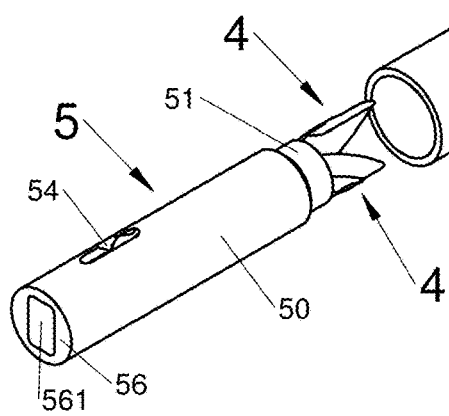
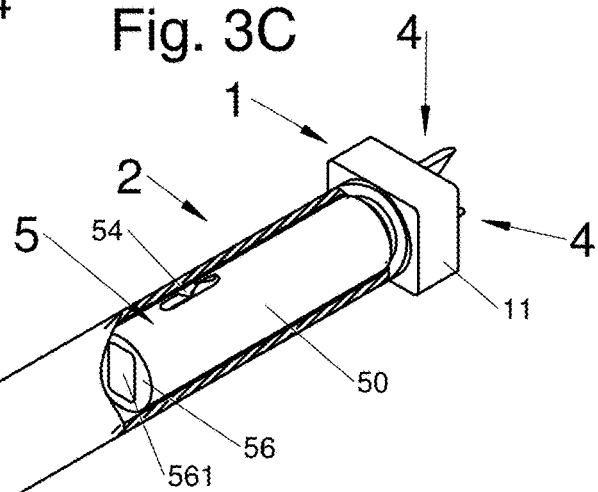
Fig. 3C
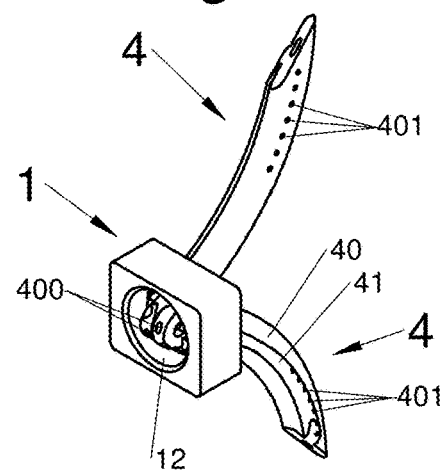
Fig. 3D

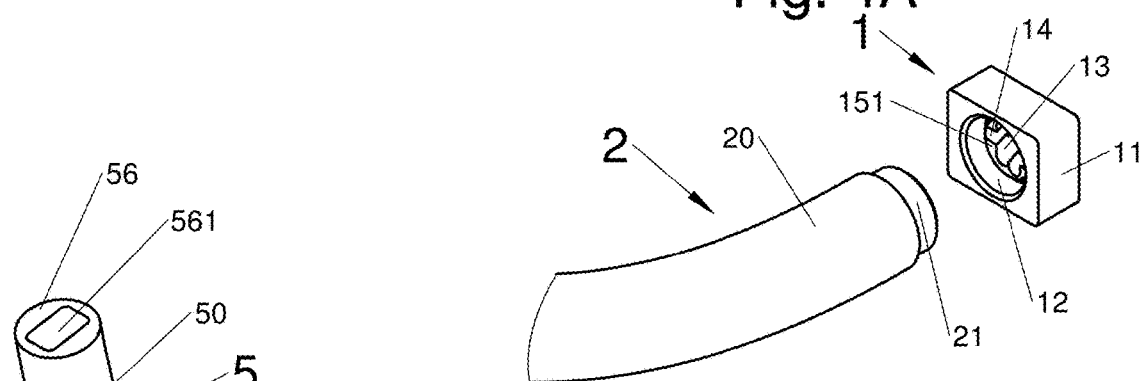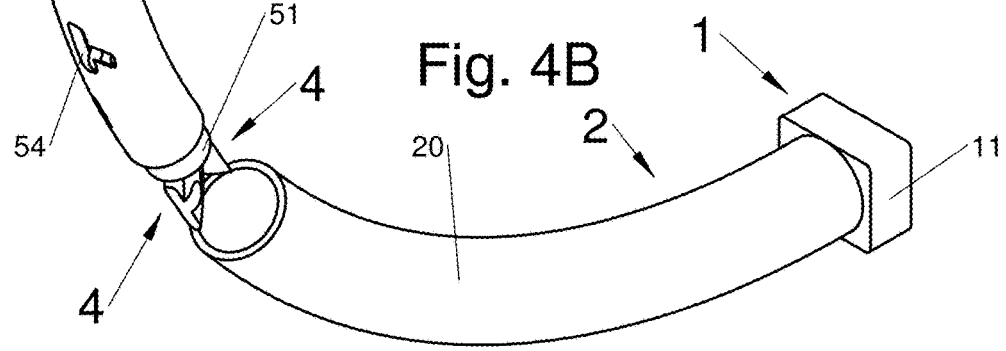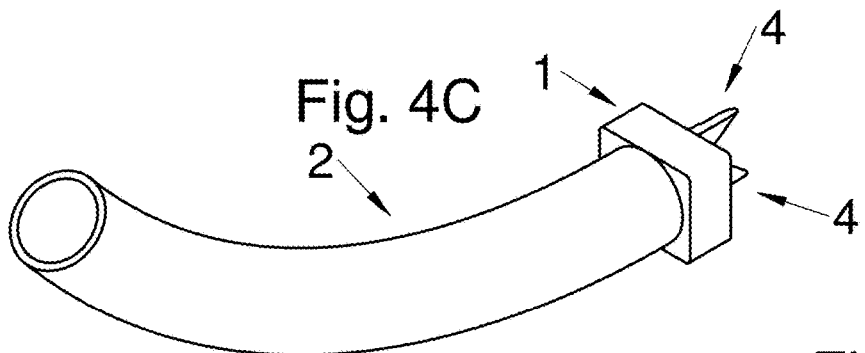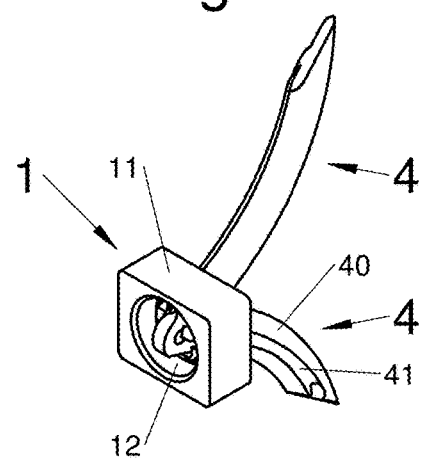

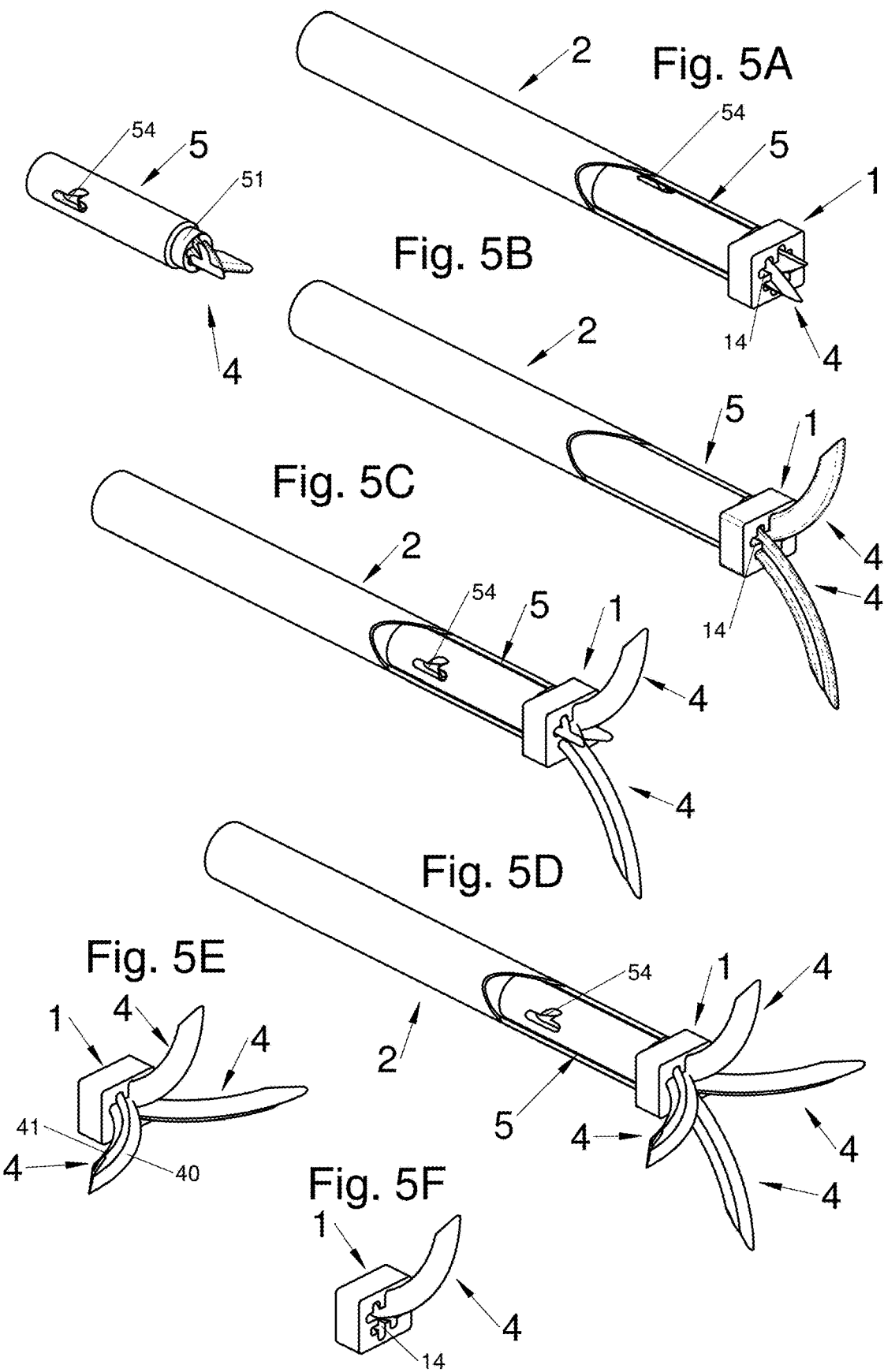

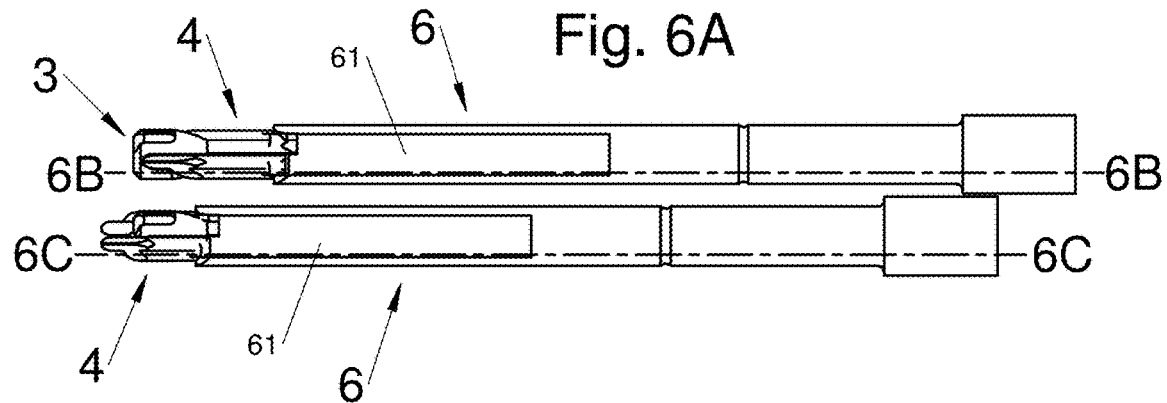
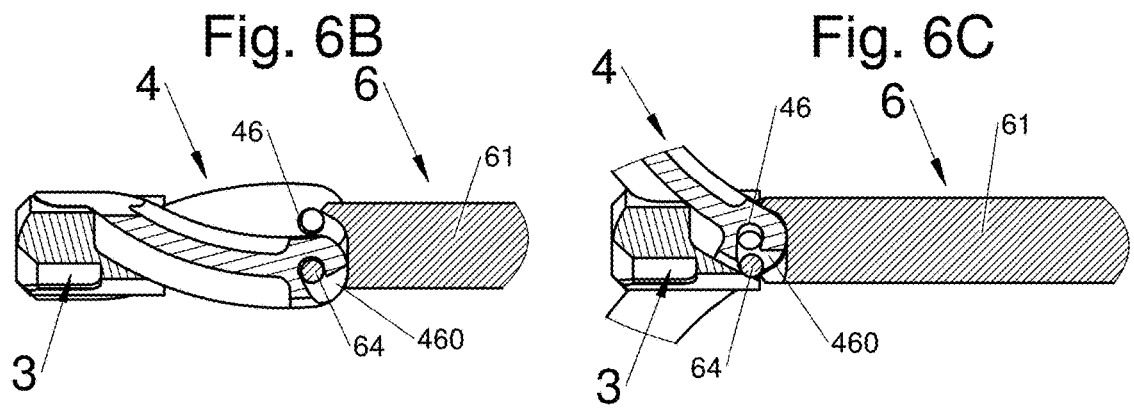
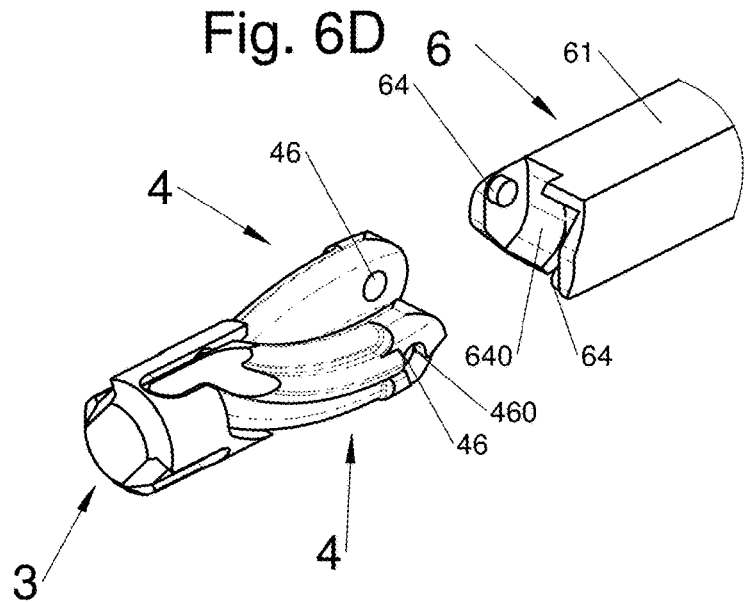

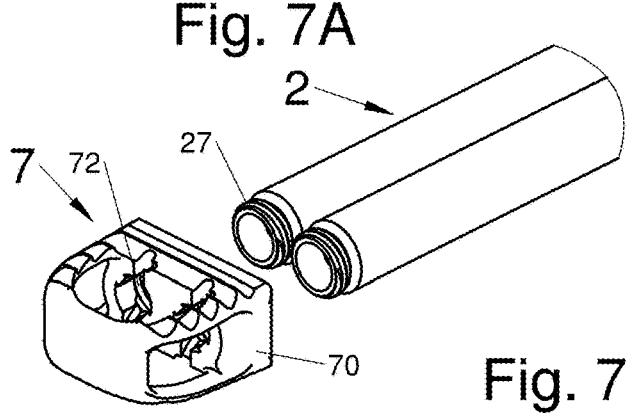
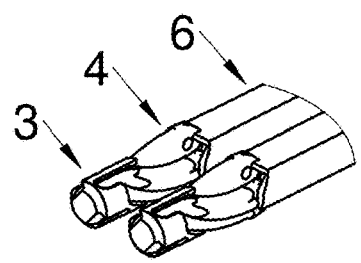
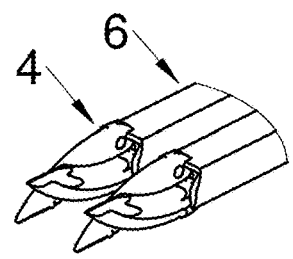
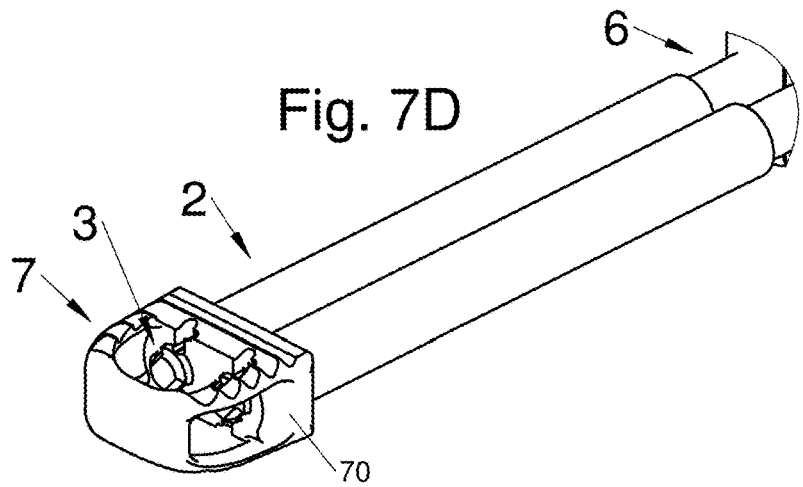
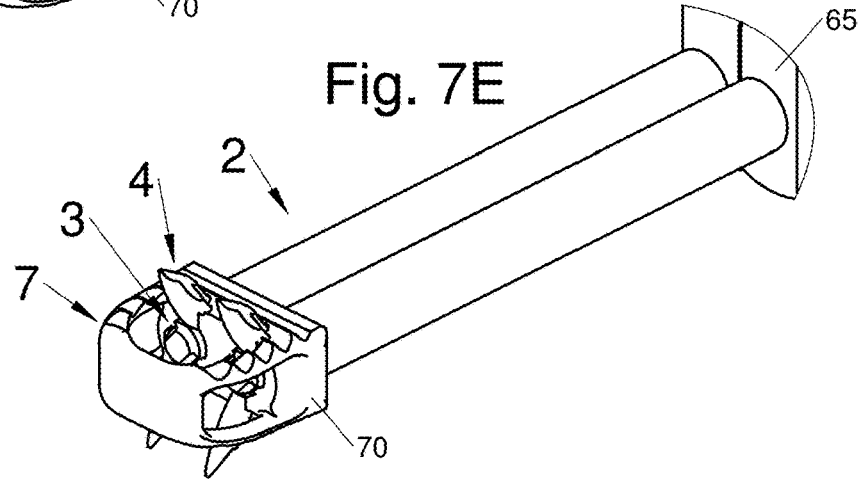

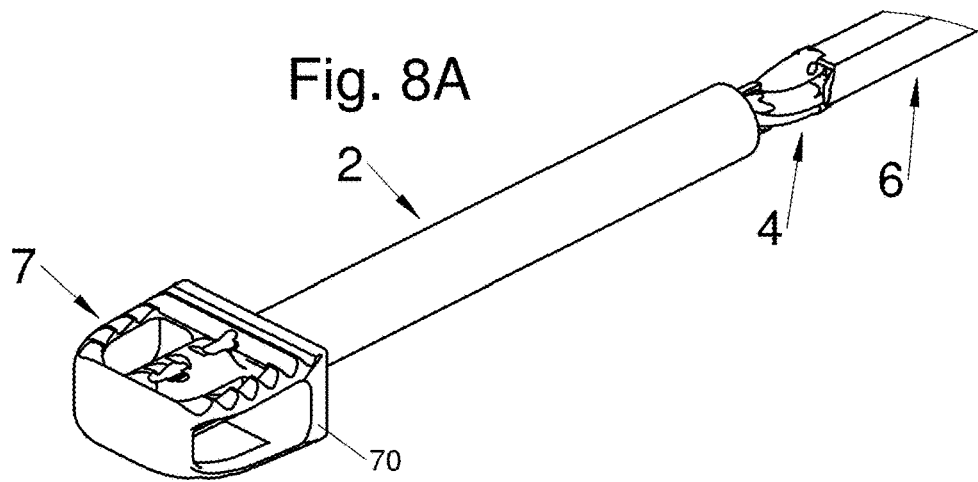
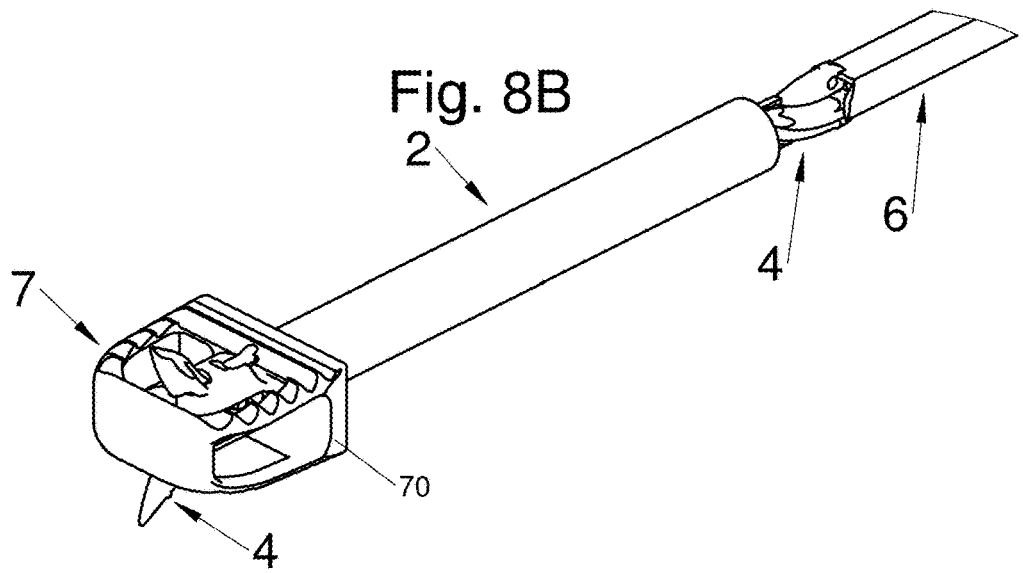
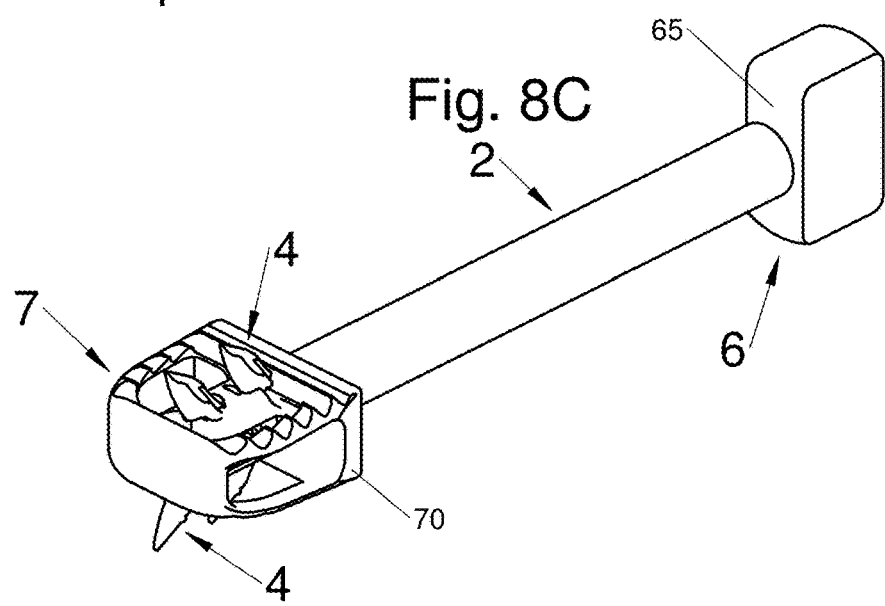

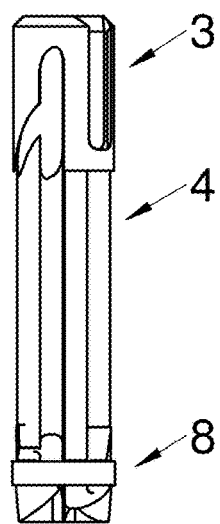
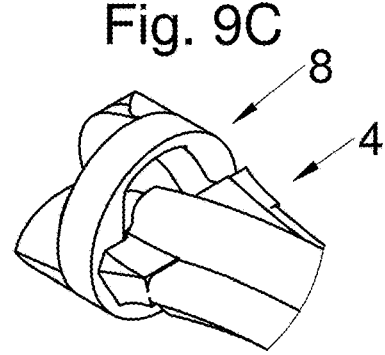
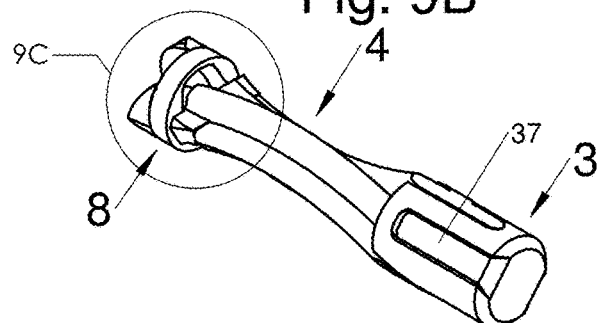
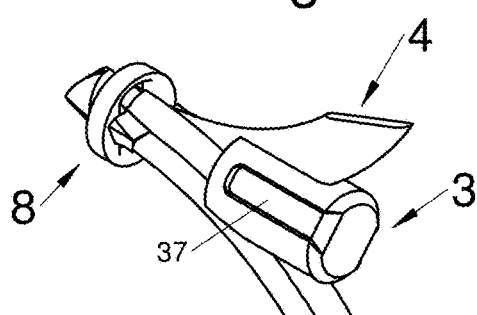
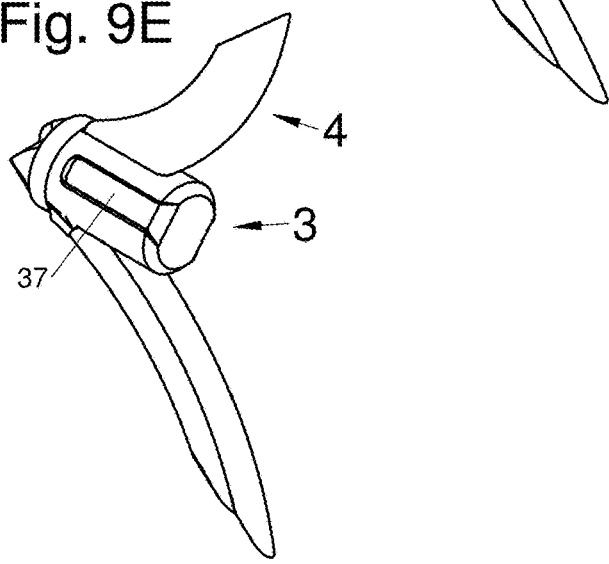
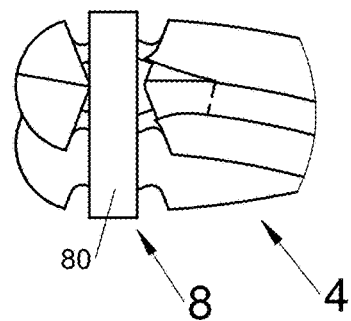

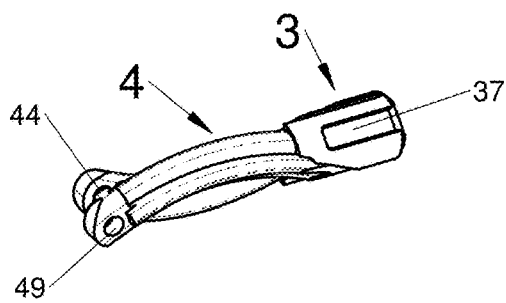
Fig. 12A
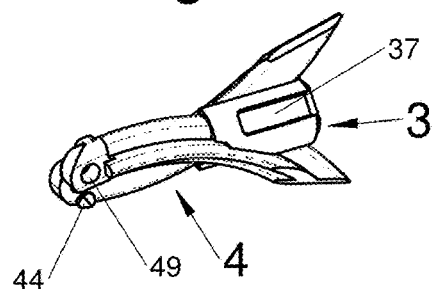
Fig. 12B
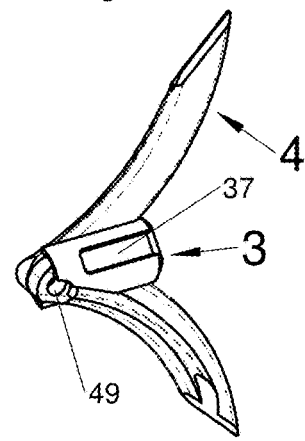
Fig. 12C
Fig. 12D
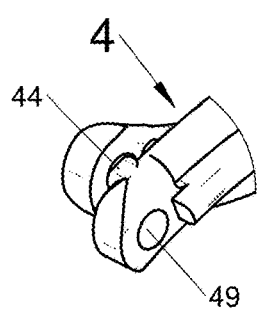
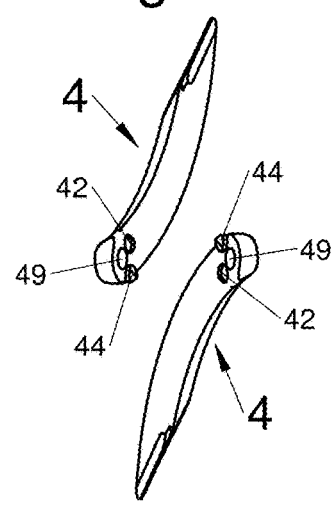
Fig. 12E

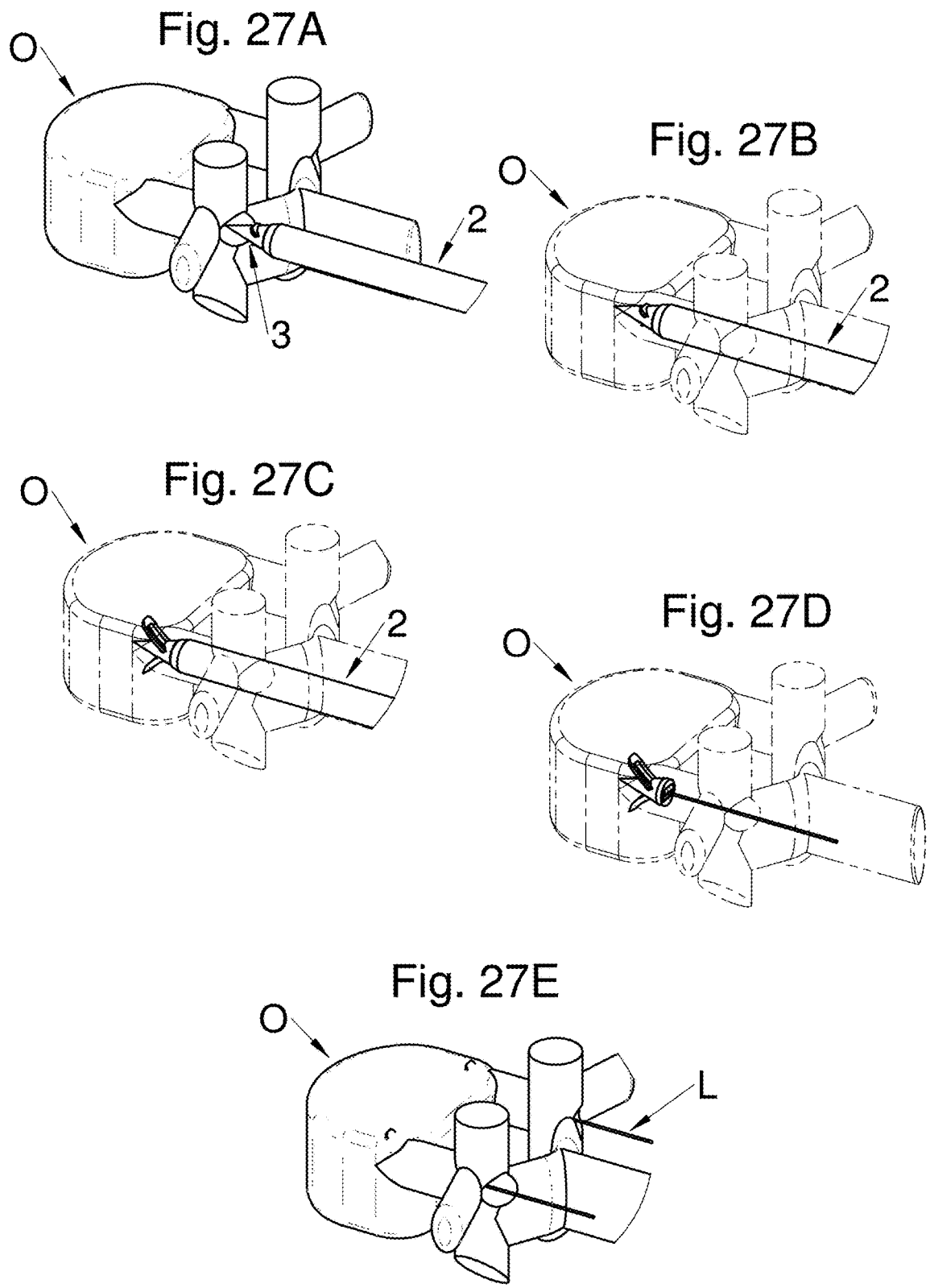

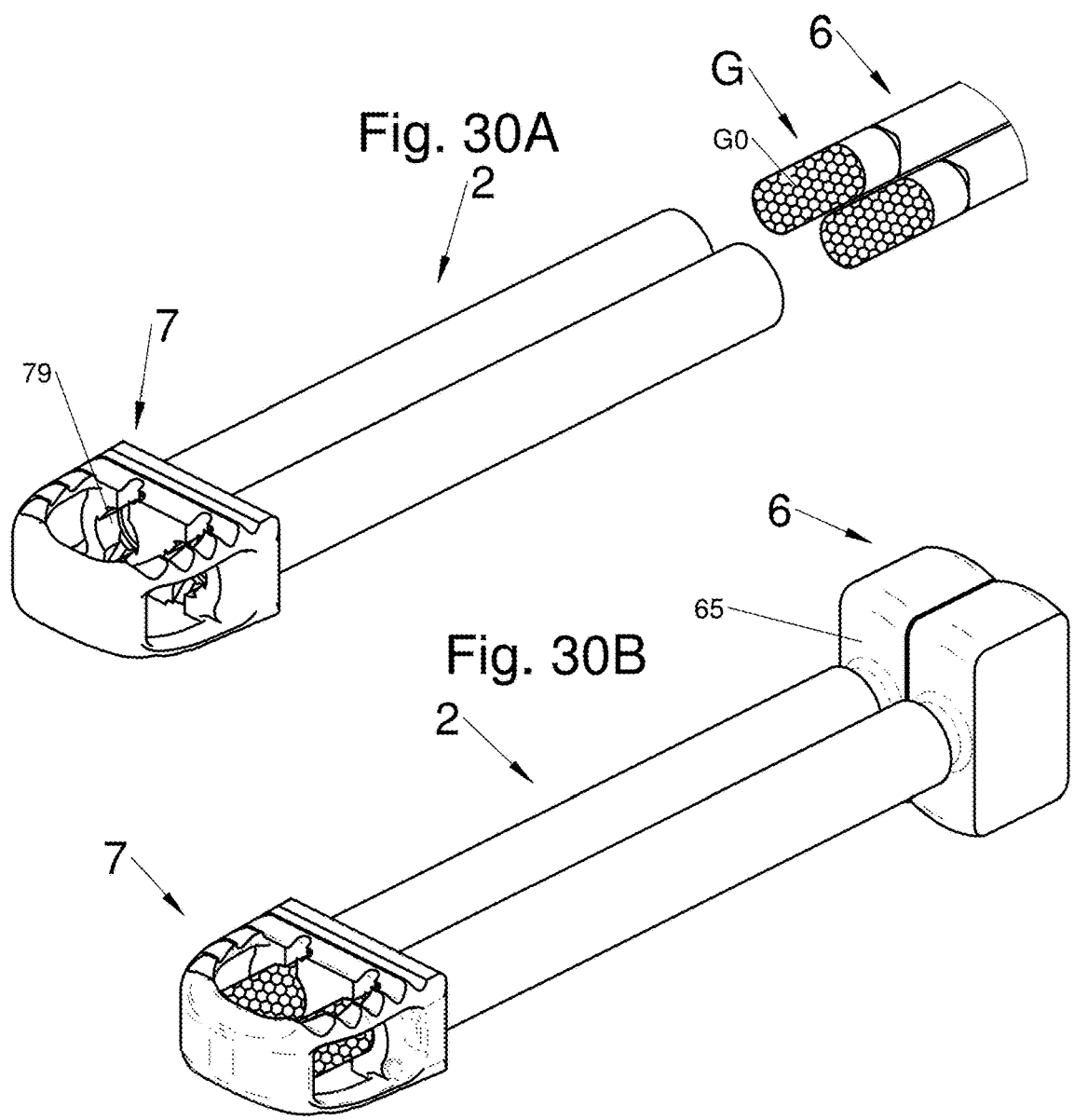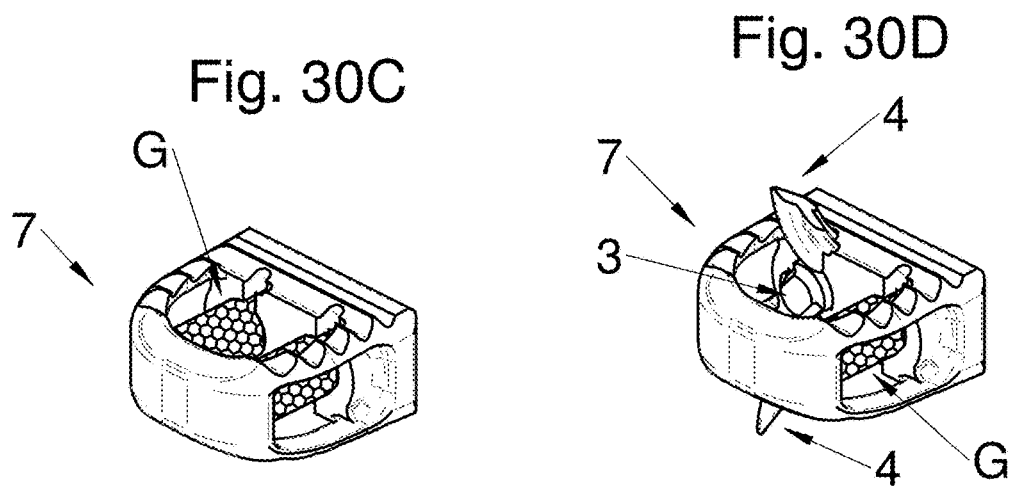

Fig. 31A
Fig. 31B
Fig. 31C
Fig. 31D
Fig. 31E
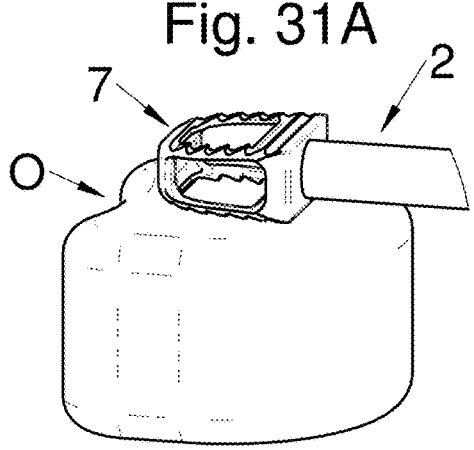
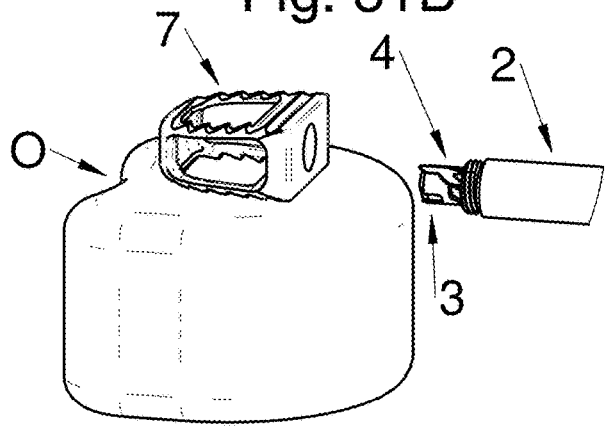
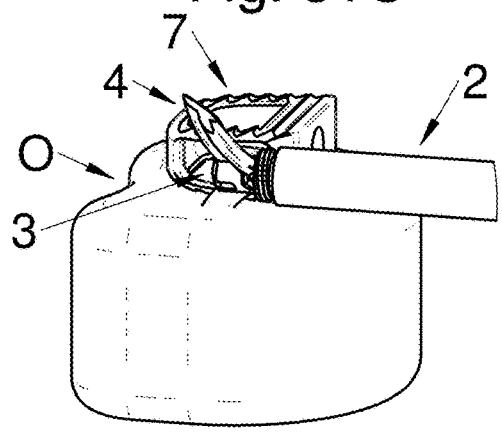
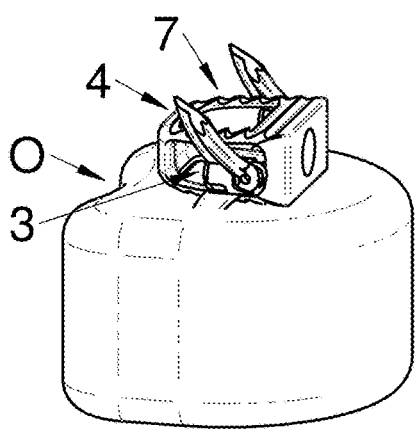
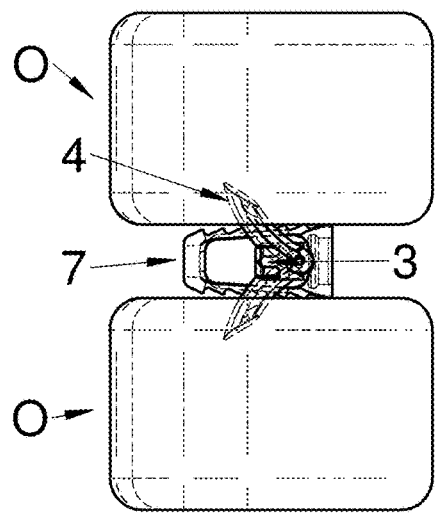

BONE ANCHORING SYSTEM, ASSOCIATED IMPLANT AND INSTRUMENTATION

CROSS-REFERENCE TO RELATED APPLICATIONS

Priority is claimed under 35 U.S.C. § 119 to French Patent Application No. FR1653849 filed in FRANCE on Apr. 28, 2016.

BACKGROUND

The present invention relates to the field of orthopedic surgery and in particular spinal surgery.

The invention more particularly relates to bone anchoring instrumentations, for implanting at least one anchoring device in at least one bone tissue, optionally associated with at least one implant, in particular a spinal implant (such as intervertebral prostheses and intersomatic cages).

A problem in this field relates to the reliability and stability of anchoring devices inside bone tissues, whether these anchoring devices are either associated with one or several implants or not. In particular, the anchoring devices should preferably cause minimum lesions to the bone tissue (avoid cracks and more significant damages than is required by the size of the actual device), but they should especially allow reliable fixation since many therapeutic techniques rely on bone growth which generally requires that the devices anchored in the bone tissue remain as immobile as possible. Further, another problem relates to the facility of implantation. Indeed, there exists a risk that the anchoring device be poorly positioned, especially because of the difficulty in technically carrying out the implantation of the anchoring device. Thus, it is for example possible that a too external (or even internal) position of the anchoring device with respect to the bone tissue, have detrimental consequences, such as for example the weakening of its stabilizing capability.

Patent applications published as WO 2008/149223, WO 2011/80535 and FR 2 987 256 filed by the applicant of the present application are known in the prior art, entirely incorporated herein by reference and to which the reader may refer for examining the various solved problems and the advantages provided by this type of solutions, including a bone anchoring instrumentation, particularly for the fixation, between vertebrae, of implants such as intervertebral disc prostheses or intersomatic cages. In the particular case of the rachis, various types of vertebral implants are known such as intervertebral disc prostheses or intersomatic cages or of corpectomy for example, or further vertebral plates or interspinal implants. These various types of implants generally have to be as less invasive as possible in order to facilitate their implantation and limit the risks of damages to the sensitive surrounding tissues which are notably nerves and blood vessels. The same applies for the bone anchoring devices (such as the straight or curved anchors or further screws) since it is preferable that the fixation occupies as less space as possible while being as reliable as possible.

However, these solutions are very specific to the implants for which they are intended to allow fixation and cannot be used or adapted for other types of orthopedic surgery (i.e., other implants and other bone tissues than those of the rachis). Further, the reliability of the bone anchoring may still be improved, especially in order to allow the fixation of other types of implants (for example smaller implants) for which the bone anchoring has to be more stable. Indeed, depending on the type of implant which is to be placed and/or depending on the type of bone on which the implant is desirably anchored, it may be desirable to have an extended anchoring and/or variable depth, especially a more "expansed" or "deployed" anchoring, i.e. greater than allowed by these known solutions. Thus, it is generally intended that the anchoring devices may be rapidly or easily implanted with minimum invasivity, i.e. one seeks to limit the size of the incisions and of the damages on the surrounding tissues. Indeed, access to the implantation sites (such as the intervertebral spaces) is often delicate because of the congestion, especially near the intervertebral space because of the presence of blood vessels and nerves. It will be noted that the invasivity problem provides additional constraints for addressing the problem of stability, especially because the fact of reducing the dimensions for reducing the invasivity is accompanied by risks of unstability. It is therefore interesting to provide a solution which gives the possibility of reconciling the constraints related to invasivity and stability, i.e. limiting the invasivity (reduced as compared with known solutions) while providing a performing anchoring, or even as more performing, in the bone tissue.

In this context, it is interesting to propose a bone anchoring, notably through implants and/or anchoring devices and/or instrumentation, which may be easy, stable, reliable and as less invasive as possible.

BRIEF SUMMARY

Various embodiments of the present invention have the purpose of overcoming some drawbacks of the prior art by proposing a bone anchoring system, in particular facilitating rapid implantation of at least one anchoring device in at least one bone tissue while providing stable anchoring and reduced invasivity.

This aim is attained by an anchoring system, for implantation of at least one anchoring device in at least one tissue, preferably a bone tissue, the system comprises at least the following instruments:
  at least one anchoring device comprising a body, preferably curved, extending between an anterior end intended to penetrate without any deformation in the bone tissue and a posterior end intended to remain turned outward of the bone tissue, both of these ends defining a longitudinal axis;
  at least one guide extending along a longitudinal axis between a posterior end and an anterior end and comprising at least one guiding surface (for example in a groove or on a rib) oriented substantially along (for example parallel to, or at least not orthogonal to) the longitudinal axis, and configured to guide said anchoring device.

Preferably, the guiding surface (or guiding surfaces) of the guide are configured to guide the anchoring device, preferably at least two anchoring devices, along the trajectory of their curvature. Indeed, the guiding surface and the anchoring device are complementary such that the guide facilitates the deployment of the anchoring device and the penetration of the latter in the osseous tissue.

According to another feature, the anchoring system comprises means for cooperation with at least one implant so as to anchor said implant in said bone tissue.

According to another feature, said implant comprises at least one bone fixation plate intended to be fixed on said bone tissue by at least one anchoring device of said system.

According to another feature, the implant comprises at least one opening able to receive a bone graft.

According to another feature, the implant comprises at least one peripheral wall, at least one part, called posterior, includes at least one passage with adapted dimensions for receiving at least one anchoring device so as to allow the passing of this rigid anchoring device without any deformation in the bone tissue.

According to another feature, the peripheral wall is configured, at least at the posterior part, for cooperating with at least one gripping end of one of the instruments of said system.

According to another feature, said instrument, the gripping end of which cooperates with the peripheral wall of implantation of the implant, is the support and/or the fixation plate and/or the guide.

According to another feature, the anchoring system comprises at least one additional instrument from among the following instruments:
- at least one support comprising a hollow and elongated body along a longitudinal axis extending between a first end, and a second end, said hollow body being able to receive said anchoring device and to guide it towards the bone tissue;
- at least one fixation plate, intended to be placed bearing against the bone tissue, comprising a body crossed by a guide opening able to guide at least one anchoring device and of receiving the first end of the support;
- at least one loader, comprising a hollow body, able to receive the anchoring device, and elongated along a longitudinal axis extending between a first end and a second end.

According to another feature, the anchoring system a comprises at least one impactor comprising a head, with shapes and dimensions adapted for sliding inside the support and/or the loader and pushing the anchoring device towards the bone tissue.

According to another feature, the bone anchoring device has a shape of plate curved and elongated along a longitudinal axis extending between its anterior end and its posterior end.

According to another feature, the plate of the anchoring device is provided with at least one longitudinal rib or with at least one second plate extending along the longitudinal axis, not parallel to the first plate, and giving to the anchoring device an L-shaped, T-shaped, V-shaped, U-shaped or H-shaped section.

According to another feature, on the one hand, the impactor comprises at least one surface for pushing the anchoring device and, on the other hand, the anchoring device and the impactor comprise at least one mutual cooperation abutment for maintaining the anchoring device in position with respect to the impactor.

According to another feature, the anchoring system comprises two anchoring devices retained together by at least one retaining element.

According to another feature, the retaining element comprises a ring-shaped body positioned around or in proximity to the posterior end of the anchoring device.

According to another feature, the retaining element comprises an external threading or an internal tapping complementary of another instrument of the system.

According to another feature, the anchoring system comprises two curved anchoring devices each having at least one radius of curvature and positioned one beside the other inside the support, and optionally inside the loader, in a folded-back position in which their longitudinal axes are substantially parallel with each other, but their radii of curvature are oriented in different directions, so as to allow deployment towards a deployed position when they are implanted in the bone tissue.

According to another feature, the anchoring system comprises at least one deployment guide allowing the anchoring devices to be deployed in the bone tissue by following a trajectory defined by their radii of curvature.

According to another feature, the plate of the anchoring device comprises at least one housing or a groove able to receive a binding means allowing to bind the anchoring device to the implant.

According to another feature, the support and the plate comprise mutual coupling means.

According to another feature, the support and the implant comprise mutual coupling means.

According to another feature, the posterior end of the support is open for allowing insertion of the impactor and/or the loader into the support in order to push and guide the anchoring device towards the bone tissue.

According to another feature, the body of the support is curved for guiding the anchoring device(s) along a curvilinear path of approach to the bone tissue.

According to another feature, the body of the loader is curved.

According to another feature, the pusher of the impactor is adapted for pushing the head of the impactor in an opening of the loader so as to implant the anchoring device contained in the loader in the bone tissue.

According to another feature, the head is of the same dimension as the loader and the pusher of the impactor comprises at least one abutment allowing limitation of the movement of the head beyond the loader.

According to another feature, the head of the impactor comprises on the one hand at least one pushing surface able to cooperate with the posterior end of the anchoring device and maintaining the latter against the impactor by the mutual cooperation between the cooperation abutment of the impactor and the cooperation abutment of the anchoring device.

According to another feature, the fixation plate comprises, in addition to the guide opening adapted for at least partially guiding the anchoring device, at least one opening adapted for at least partially receiving the guide.

According to another feature, the plate comprises at least one abutment for maintaining the guide in the plate.

According to another feature, the anterior end of the loader comprises a means for cooperating with the posterior end of the guide.

According to another feature, the loader comprises at least one opening in a wall of the loader so as to allow the introduction of at least one anchoring device inside the loader.

According to another feature, the guide comprises at least one groove intended to cooperate with the walls of the passage in the implant or in the plate.

According to another feature, the anterior end of the guide comprises a chamfer or a bevel facilitating the penetration of the element in the bone tissue.

According to another feature, the guide and the plate comprise mutual coupling means.

According to another feature, the anchoring device comprises locking means cooperating with at least one of the following means:
- complementary means of a guide,
- complementary means of at least one additional lock,
- complementary means of a fixation plate.

Another aim is to propose an implant configured for facilitating and accelerating its implantation and its anchoring in at least one bone tissue in a stable and reliable way and as less invasive as possible.

This aim is attained by a vertebral implant comprises at least one means for cooperation with the support and at least one coupling means with at least one anchoring device for the use of the implant in a system according to one of the features of various embodiments of the present invention.

According to another feature, the bone anchoring instrumentation comprises at least one support able to receive at least one anchoring device and to guide it towards the bone tissue in order to obtain a system according to one of the features of various embodiments of the present invention.

Another aim is to propose bone anchoring instrumentation configured for facilitating and accelerating the implantation of an implant and/or bone anchoring, by improving the stability, the reliability and by reducing the invasivity of the implantation.

This aim is attained by a bone anchoring instrumentation comprises at least one additional instrument or implant according to one of the features of various embodiments of the present invention.

BRIEF DESCRIPTION OF THE SEVERAL VIEWS OF THE DRAWING

Other particularities and advantages of various embodiments of the present invention will appear more clearly upon reading the description hereafter, made with reference to the appended drawings, wherein:

FIG. 1A illustrates a rear perspective view of a bone anchoring system according to an embodiment comprising a support and an fixation plate; the FIG. 1B illustrates a rear perspective view of the anchoring system completed with two anchors, a guide and an impactor; the FIG. 1C illustrates a front perspective view of a part of the anchoring system comprising the fixation plate, the support, the guide; the FIGS. 1D and 1E illustrate rear perspective views of the anchoring system completed with the anchors and a loader; and the FIG. 1F illustrates a rear perspective view of a part of the anchoring system comprising the fixation plate, the guide and the deployed anchors;

FIG. 3A illustrates a rear perspective view of an fixation plate according to an embodiment; the FIGS. 3B and 3C illustrate rear perspective views, with a transparent portion in the FIG. 3C, of a bone anchoring system according to an embodiment comprising two anchors, an fixation plate, a support and a loader, respectively before and after the introduction of the loader into the support; the FIG. 3D illustrates a rear perspective view of a part of the anchoring system with its micro-perforated anchors (provided with cannulas), deployed through the fixation plate;

FIG. 4A illustrates a rear perspective view of a part of the bone anchoring system according to an embodiment comprising an fixation plate and a curved support; the FIGS. 4B and 4C illustrate rear perspective views of the anchoring system completed with two anchors and a curved loader, respectively before and after the introduction of the loader into the support; and the FIG. 4D illustrates a rear perspective view of a part of the anchoring system with its anchors deployed through the fixation plate;

FIG. 5A illustrates a front perspective view, with a transparent portion, of a bone anchoring system according to an embodiment comprising two first anchors being deployed through an fixation plate, via a loader introduced into a support; the FIGS. 5B and 5C illustrate front perspective views, with a transparent portion, of the anchoring system comprising the deployed anchors and the loader containing two second anchors, respectively, before introducing a second loader provided with two second anchors while the first two anchors are deployed and after introducing the second loader into the support for deployment of the second two anchors; the FIG. 5D illustrates a front perspective view, with a transparent portion, of the anchoring system with the four deployed anchors; the FIGS. 5E and 5F illustrate front perspective views of a part of the anchoring system comprising the fixation plate, respectively with three deployed anchors and with a single deployed anchor;

FIG. 6A illustrates a profile view of two bone anchoring systems according to an embodiment comprising two anchors, a guide and an impactor, respectively before and after deployment of the anchors; the FIGS. 6B and 6C illustrate sectional views respectively along the plane 6B-6B and along the plane 6C-6C of the FIG. 6A of the anchoring systems of the FIG. 6A; the FIG. 6D illustrates a front perspective of these systems before coupling between the impactor and the anchors retained by the guide;

FIG. 7A illustrates a front perspective view of a bone anchoring system according to an embodiment comprising an implant and a support; the FIGS. 7B and 7C illustrate front perspective views of an impactor on which are mounted two anchors, with and without a guide respectively retaining the anchors; the FIGS. 7D and 7E illustrate front perspective views of the same anchoring system, respectively before and after deployment of the anchors through the implant;

FIGS. 8A, 8B and 8C illustrate front perspective views of an anchoring system according to an embodiment comprising an implant, four anchors, a support and an impactor, respectively before the deployment of the first two anchors through the implant, and during and after the deployment of two second anchors through the implant;

FIG. 9A illustrates a profile view of an embodiment of a bone anchoring system, comprising two anchors retained at their posterior end by a retaining element on the one hand and at their anterior end by a guide on the other hand; the FIGS. 9B, 9D and 9E illustrate front perspective views of the system, respectively before, during and after the deployment of the anchors; the FIGS. 9C and 9F respectively illustrate a perspective view and a profile view of the posterior end of the anchors retained by the retaining element;

FIGS. 12A, 12B and 12C illustrate rear perspective views of an embodiment of a bone anchoring system, comprising two anchors retained by a guide at their anterior end, respectively before, during and after the deployment of the anchors; the FIG. 12D illustrates a rear perspective view of the posterior end of the anchors; and the FIG. 12E illustrates a perspective view of both anchors provided with locking means;

FIGS. 27A, 27B, 27C, 27D and 27E illustrate rear perspective views of a vertebra and a bone anchoring system according to an embodiment comprising two anchors, a support and a guide, respectively before introducing the system into one of the vertebral pedicles, before introducing the system into the pedicle but before deployment of the anchors, and then after deployment of the anchors, after withdrawal of the support, and finally after repeating the same steps for the other vertebral pedicle;

FIGS. 30A and 30B illustrate front perspective views of an embodiment of a bone anchoring system comprising an implant which may be implanted by using an instrumentation comprising two supports and two impactors, respectively before and after introducing a graft into the implant; the FIGS. 30C and 30D illustrate perspective views of a part of the system comprising the implant, respectively after introducing two grafts and after introducing one graft and two anchors and a guide into the implant;

FIG. 31E illustrates a profile view of an embodiment of a bone anchoring system after insertion and anchoring of an implant between two adjacent bone structures, the FIGS. 31A, 31B, 31C and 31D illustrate perspective views of one of these two bone structures for more clarity and of this system, respectively after introducing the implant through a support, after withdrawal of the support and then return of the support loaded with a first bone anchoring, during the impaction of a first bone anchoring in both bone structures and after impaction of a second bone anchoring in these two bone structures and withdrawal of the support.

DETAILED DESCRIPTION OF VARIOUS EMBODIMENTS

Figure 2A:
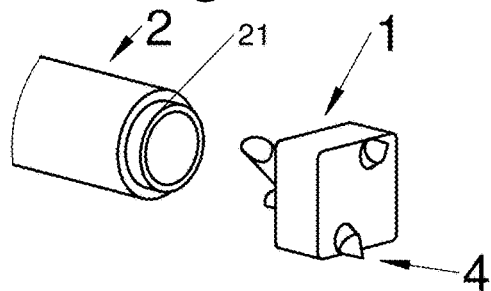
FIGS. 2A and 2B illustrate front perspective views of a part of a bone anchoring system, according to an embodiment comprising anchors, an fixation plate and a support, respectively before and after the deployment of the anchors; the FIGS. 2C and 2D illustrate front perspective views of a part of a bone anchoring system, according to another embodiment comprising anchors, an fixation plate and a support, respectively before and after the deployment of the anchoring device; the FIGS. 2E, 2F and 2G respectively illustrate front perspective views of a part of another anchoring system, comprising an fixation plate, a guide and anchors for which the angular orientation is adjustable.

The present application relates to an anchoring system for implanting at least one anchoring device in at least one tissue, preferably bone tissue. The present application refers by the terms of "bone anchoring device", "anchor" or further more generally "bone anchoring" to various types of devices comprising at least one element intended to penetrate the bone tissue, along a rectilinear or (preferably) curved path, under the action of a thrust generally exerted as repeated strikes, impacts, on the anchor. It will be noted that by the term of "impacting" is designated here the action of planting the anchoring device in the bone tissues, generally by successive strikes, by means of an impaction device designated here by the term of "impactor". In various embodiments, the bone anchoring is obtained by a combination of several distinct elements including anchors (4). In particular, these anchors (4) are sometimes anchored alone in the bone but they may be combined with at least one other element also intended to remain in place in or against the bone tissue, such as at least one guide (3) and/or at least one fixation plate (1), for example through at least one support (2) facilitating the implantation of the anchoring device (optionally with the guide and/or the fixation plate). The terms of "anchor or anchoring" in the present application refers to a sufficiently solid and deep implantation of at least one anchoring device in the bone tissues for ensuring good hold of this device, optionally associated with another element, such as an implant, for example being supported against this bone tissue. These terms are therefore used as opposed to other less reliable stabilization means, for example such as simple anti-skid teeth frequently used in the prior art. According to the definition of the present application, an "anchored" implant typically includes at least one anchoring device, such as a screw or an anchor, but it may also be simply linked to such anchoring, through a rigid or flexible means (like for example a ligament, a metal braid, for example formed by a weaving, a braiding or a knitting of a biocompatible material).

The present application also relates to at least one instrumentation adapted for achieving the bone anchoring and which may be part of said system. Further, the instrumentation may also be used for the implantation and/or fixation of at least one type of implant which may also be part of said bone anchoring system. Generally, various embodiments of the present invention preferably comprise an anchoring device (4) which may therefore include or be designated in the present application under the term of "anchor" (4) with reference to its anchoring function as described below, without inducing any limitation. Anchors of various types are already described in the literature, notably in the published applications FR 2 916 956, FR 2 954 692, WO 2008/149223 and WO 2013/124453 filed by the applicant of the present application. However, the present application draws an advantage from the teachings of these applications and from recent discoveries of the applicant detailed in the present application, especially dealing with the path of the anchors (4) during their penetration into the bone tissue and/or with their locking and/or with their deployment which may advantageously be accomplished via a conduit in an instrument.

Generally, the present application relates to an anchoring system for implanting at least one anchoring device in at least one bone tissue. In some embodiments, the anchoring system comprising at least one of the following elements or instruments:

an anchoring device (4) able to be implanted in a bone tissue (O), a guide (3) able to guide the anchoring device (4) towards the bone tissue (O).

Of course, it is possible (or even often preferred) to use several anchoring devices (4) (or "anchors") at the same time. Generally, at least two anchors (4) will be used in combination with each other because their combination provides advantages described in the present application, which prove that there are not just juxtaposed but indeed combined, thereby providing a synergic effect. In particular, two anchors deployed at the same time are fast and easy to implant, but further provide a reliable fixation which is impossible to obtain with any of the anchoring devices known in the prior art. In general, it is possible to guide these devices (especially when they are two) by a single guide or a single and same plate, in particular when they are implanted with the help of a support (2), optionally completed with a loader (5).

In some embodiments, the anchoring system comprises at least one additional instrument, for example, from among the following types of instruments:
- a support (2) able to guide the anchoring device (4) towards the bone tissue (O),
- an fixation plate (1) able to be arranged bearing against the bone tissue (O),
- a loader (5) able to receive the anchoring device (4),
- an impactor (6) able to slide inside the support (2) and/or the loader (5), for pushing the anchoring device (4) towards the bone tissue (O).

More particularly, a system will generally be selected for which the instruments have technical features allowing it to address at least one part of the problems mentioned in the present application. Thus, some embodiments relate to a bone anchoring system comprising:
- at least one anchoring device (4) comprising a body, preferably curved, extending between an anterior end intended to penetrate into the bone tissue (O) and a posterior end intended to remain outside the bone tissue (O),
- at least one guide (3) extending along a longitudinal axis between a posterior end and an anterior end and comprising at least one guide groove (34), substantially parallel to the longitudinal axis, able to guide at least one anchoring device (4) toward the bone tissue (O).

Anchoring systems comprising at least one anchoring device and cooperating with at least one guide, for example such as in some embodiments described herein, has the advantage of guiding the deployment of said anchoring device towards (or into) the bone tissue. Indeed, the guide may generally be disposed on the anterior end of the anchor so as to guide it forward along the trajectory of implantation. In particular, when at least two anchors are used in combination, they are generally disposed into a the folded position and deployed to a final position within the osseous tissue (in a so-called deployed position), in which their respective anterior ends diverge from each other, in such a manner that the curved bodies of the anchors have a posterior portion lying apposed to each other (and often locked or at least maintained by a cooperation of their respective shapes or configurations or means) while their anterior have been spread from each other because of the trajectory of implantation (which preferably follows the curvature of the anchor itself). Consequently, the guide participates in the indexing of the orientation of the device(s) thanks to their complementarity of shapes and/or the complementarity of their shapes with the guiding surfaces of the guide (for example as the guiding groove (34) cooperating with an external surface, such as the plate 40 and/or the groove 41 of the anchoring device). This may help to avoid an incorrect positioning of the anchoring device. Thus, the guide orientates and directs the deployment of the anchoring device to the bone tissue, so as to improve the simplicity and ease of the implantation, and to reduce the invasiveness of the whole system. Moreover, by the cooperation of the anchoring devices with the guide contributes to the stability of the system.

In some embodiments, this anchoring system further comprises:
- at least one support (2) comprising a hollow and elongated body (20) along a longitudinal axis extending between a first end, and a second end, said hollow body (20) being able to receive said anchoring device (4) and guiding it towards the bone tissue (O),
- at least one fixation plate (1), intended to be placed against the bone tissue (O), comprising a body (10) crossed by a guide opening (14) able to guide at least one anchoring device (4) and to receive the first end of the support (2);
- at least one loader (5), comprising a hollow body (50), able to receive the anchoring device (4), and elongated along a longitudinal axis extending between a first end and a second end;
- at least one impactor (6) comprising a head (61), with shapes and dimensions adapted for sliding inside the support (2) and pushing the anchoring device (4) towards the bone tissue (O).

Some embodiments relate to systems comprising all these elements or instruments, but any combination of at least one portion of these elements or instruments is possible. It will be noted that in some of these embodiments, the system comprises several anchors, sometimes cooperating with each other in order to obtain more stability and more reliability of the anchoring. It is possible to provide anchors which are different from each other, for example complementary with each other, especially for their mutual locking as detailed in the present application, but in most of the embodiments described here, both anchors are the same, which has the advantage to obtaining symmetrical anchoring and of limiting the manufacturing costs and those for managing the inventories of different anchors, while limiting the risks of confusion between the various types of anchors.

On the other hand, the present application also relates to a method for preparing at least one bone anchoring, prior to orthopedic surgery. Indeed, the various devices of the system according to various embodiments of the invention are generally complementary with each other and have many advantages in terms of preparation cost and preparation time, in addition to those for the implantation. Therefore they may for example be delivered as a kit or at least partially assembled or arranged (retained) relatively to each other in order to allow a gain in time, for example by providing a sterile package of some embodiments of the system ready for use by the surgeon. Thus, some embodiments of a preparation method in view to bone anchoring are within the scope of the present application and bone anchoring methods may also be contemplated if required. The present application therefore also relates to some embodiments of a preparation method for implanting at least one anchoring device (4) in at least one bone tissue (O), comprising provision of the following elements, as described in the present application:
- at least one device (4) comprising a body, preferably curved, extending between an anterior end intended to penetrate without any deformation into the bone tissue (O) and a posterior end intended to remain outside the bone tissue (O),
- at least one guide (3) extending along a longitudinal axis between a posterior end and an anterior end and comprising at least one guiding surface (for example in a groove (34) or on a rib) oriented substantially along (for example parallel to, or at least not orthogonal to) the longitudinal axis, and configured to guide said anchoring device.

Preferably, the guiding surface (or guiding surfaces) of the guide are configured to guide the anchoring device, preferably at least two anchoring devices, along the trajectory of their curvature. Indeed, the guiding surface and the anchoring device are complementary such that the guide facilitates the deployment of the anchoring device and the penetration of the latter in the osseous tissue.

In some embodiments, this preparation method comprises provision of at least one additional element from among the following, as described in the present application:

- at least one support (2) comprising a hollow and elongated body (20) along a longitudinal axis extending between a first end and a second end, said hollow body (20) being able to receive said anchoring device (4) and to guide it towards the bone tissue (O),
- at least one fixation plate (1), intended to be placed bearing against the bone tissue (O), comprising a body (10) crossed by a guide opening (14) able to guide at least one anchoring device (4) and to receive the first end of the support (2);
- at least one loader (5), comprising a hollow body (50) able to receive the anchoring device (4) and elongated along a longitudinal axis extending between a first end and a second end.
- at least one impactor (6) able to sliding in the support (2) and/or the loader (5) and pushing the anchoring device (4) in order to have it penetrate into the bone tissue, generally under the action of a thrust exerted on the impactor, especially by repeated strikes.

It will be noted that in the present application, the terms of "instrumentation" or "instrument" are used for referring to various types of tools but also to elements which are in fact implants, in the sense that they are intended to remain inside the body of the patient. The terms of "elements" or "instruments" or "instrumentation" or further "implant" are thus use for various types of devices, whether these are actually anchors, instruments or implants. Indeed, some embodiments of the present application propose a set of elements, a part of which is only used during the implantation but another part of which remains in the body of the patient, especially at least partially inside a bone tissue of the patient. These terms therefore do not only designate instruments in the strict sense. Thus, the fixation plate (1), the support (2), the guide (3), the anchoring device (4), the retaining element (8) or the locking plug (10) may be considered both as instruments of the anchoring system since they generally participate in the implantation, but they may in fact be considered as implants since they sometimes participate in the bone fixation itself and may be intended to remain in the body of the patient. Thus, the fixation plate (1), the support (2), the guide (3), the anchoring device (4), the retaining element (8) and the locking plug (10) are for example instruments participating in the implantation of the implant in the bone tissue during the bone fixation, and in the implants once the anchoring instrumentation has been withdrawn from the bone tissue, i.e. at the end of the bone fixation. These terms are therefore used herein indifferently from each other and should not be construed in a limiting way. The bone anchoring system itself is considered as any possible combination of at least two of these elements, implants or instruments and always comprises at least one anchor (4).

Some embodiments of the invention will now be described with reference to the figures, which are illustrative and non-limiting, of the present application. Some embodiments relate at least to one of the three groups of following objects:

- a bone anchoring instrumentation (1, 2, 3, 5, 6) for implanting at least one anchoring device (4) in at least one bone tissue (O),
- an implant (7, P) cooperating with the instrumentation (1, 2, 3, 5, 6) of the present application so as to anchor said implant with at least one anchoring device (4) in at least one bone tissue (O),
- an anchoring system (1, 2, 3, 4, 5, 6, 7, P, 8, 10) for implanting at least one anchoring device (4), optionally associated with an implant (7, P) in at least one bone tissue (O) by means of the bone anchoring instrumentation (1, 2, 3, 5, 6) of the present application.

Each of these groups of objects may include various possible embodiments, relating to a given object. Each of the objects includes various elements (generally constitutive of the object) characterized by at least one technical feature. Each object (of a given group) concerned by at least one technical feature may be associated with at least one other object (of the same or of another group), for example as regards at least one complementary technical feature, so that the groups of objects share a common inventive concept. The various elements (for example, a plate, a tab, an abutment, a thickened portion, etc.) as well as their technical features (for example, curvature, flexibility, possibility of disengagement, height, abutment surface, etc.) are described with more details hereafter in the present application. At least one technical feature corresponding to an element of a given object solves at least one technical problem, in particular from among those mentioned in the preamble of the present application. The present application therefore describes various embodiments or configurations for each object or group of objects, by specifying at least one technical feature of at least one element. It will be understood upon reading the present application that each of the technical features of each element, described in at least one embodiment or one configuration, may be isolated from the other features of the relevant object (or concerned and/or associated objects) by said embodiment or said configuration (and therefore concerning the same element or a different element) and/or may be combined with any other technical feature described here, in various embodiments or configurations, unless the opposite is explicitly mentioned, or that these features are incompatible with each other and/or that their combination does not operate, in particular because the structural adaptations which may be required by such isolations or combinations of features, may be directly derived from the appreciation of the present application. Generally, the specific technical feature(s) relating to a given element should not be considered as exclusive of those relating to another element or instrument, nor other technical features relating to this same element or instrument, except when it clearly appears that the combination is impossible or non-functional. Although the present application details various embodiments or configurations of the invention (including preferred embodiments), its scope should not be limited to the given examples.

In some embodiments, the anchor (4) is elongated along a longitudinal axis extending between a first end, designated here as an "anterior end", intended to penetrate a bone tissue and a second end, designated here as a "posterior end", on which the thrust is exerted during the implantation and generally intended to remain withdrawal and slightly exceeding out from the bone tissue. It will be noted that the terms of "posterior" and "anterior" of the anchor (4), of the implant (7) and of the others elements or instruments (1, 2, 3, 5 and 6) are used in the present application with reference to the meaning according to which they are introduced. Thus, for the anchor (4), the first end, called anterior end, is the one intended to be inserted first and to penetrate into a bone tissue in order to fix an implant for example (figures of the plates 6, 8, 26 and 29). It will also be noted that reference is made here to a longitudinal axis between both of these ends and that this longitudinal axis therefore corresponds to an antero-posterior axis of the anchor (4), of the implant (7) and of the instrumentation (1, 2, 3, 5, 6), always with reference to the insertion direction of the anchor (4). As regards the implant (7, P), its wall or its end designated as a posterior end is the one including an opening for inserting the anchor (4) and/or means for coupling with at least one instrument such as for example the support (2), that this wall is actually posterior to the implant (7) or not during its implantation. As regards the instruments (1, 2, 3, 5, 6), the called anterior end (27, 37, 53, 61) is the one intended to be in abutment against the bone tissue (O) or against the implant (7, P) or against another element or component of the system.

On the other hand, the term of "substantially" is regularly used in the present description, notably relating to a feature such as an orientation or a direction, so as to indicate that the relevant feature may in fact be slightly different and not be exactly as designated (for example, the expression "substantially perpendicular" should be construed as "at least approximately perpendicular" since it may be possible to select an orientation which is not exactly perpendicular in order to be nonetheless able to fulfill substantially the same function). Further, the term "substantially" used in the present application may also be construed as defining that a technical feature may "generally" and often "preferably" be, as indicated but that other embodiments or configurations may be within the scope of the present invention.

Moreover, the term of "bone tissue(s)" generally designates in the present application any types of bones, whether this is a compact bone (such as for example the cortical bone or the periosteum) or a spongy (soft, porous) bone because the anchoring system of the present application may be implanted in any type of bone tissue and various embodiments are more or less adapted to some types of bone tissues. It will be noted that the use of the system may be contemplated in tissues other than bones, but that this design makes it particularly adapted to the mechanical stresses of the bone tissue.

Different types of proposed configurations in the present application are particularly advantageous since they give the possibility of addressing the problems of stability, reliability, rapidity and non-invasivity of bone anchoring in the field of orthopedic surgery. Indeed, different configurations allow to simplify and generalize the bone anchoring method for the surgeon, for example by using the same instrumentation for the implantation of the implant as for its anchoring in the bone tissue with the anchoring device, which has as advantages to reduce the time and cost of a surgical operation. Further, different configurations allow to implanting one or several bone implants and also implanting one or several anchoring devices, with the same instrumentation. Thus, this type of configuration allows minimization of the invasivity of the surgical operation since the surgeon may limit the number of necessary incisions. Some of these advantages are related to the use of a tool, here called a support (2) without inducing any limitation, which has a hollow body forming a conduit able to notably receive said anchoring device (4) and to guide it towards the bone tissue (O).

Further, this support (2) allow to hold an implant in view to its bone anchoring and optionally bringing various types of elements (especially anchors) or materials (especially of the graft or a substitute) as far as the implant on the anchoring site.

Figure 15A:
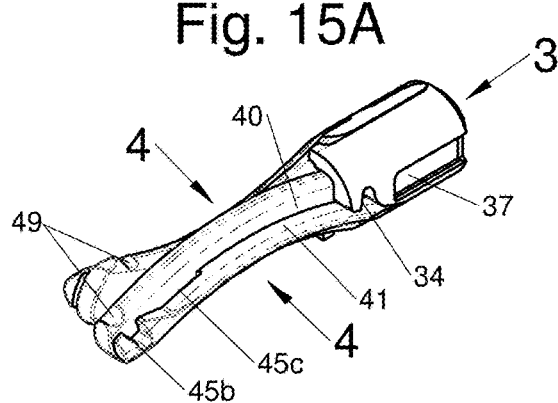
FIGS. 15A, 15B and 15C illustrate rear perspective views of an embodiment of a bone anchoring system, comprising a guide and two anchors, respectively before, during and after the deployment of the anchors; the FIG. 15D illustrates a profile view of the posterior end of this system and the FIGS. 15E and 15F respectively illustrate profile and rear face views, of this system with its deployed anchors.
Figure 15B:
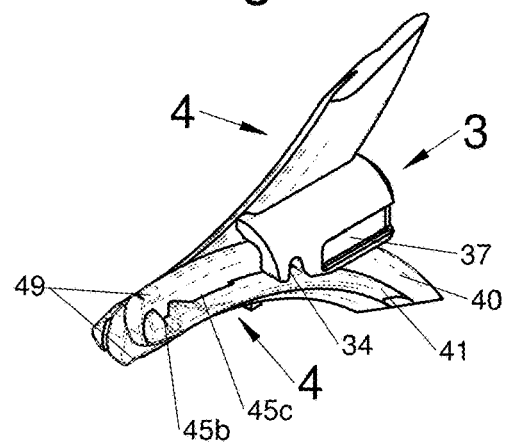
Figure 20F:
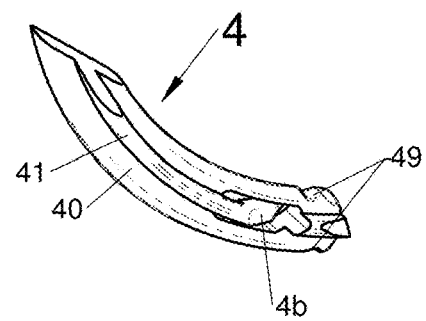
FIGS. 20E and 20F illustrate perspective views of an embodiment of an anchor of a bone anchoring system; the FIGS. 20A, 20B and 20C illustrate perspective views of this system comprising two anchors and a guide, respectively before, during and after deployment of the anchors; and the FIG. 20D illustrates a perspective view of the posterior end of the anchors locking to each other.
Figure 20E:
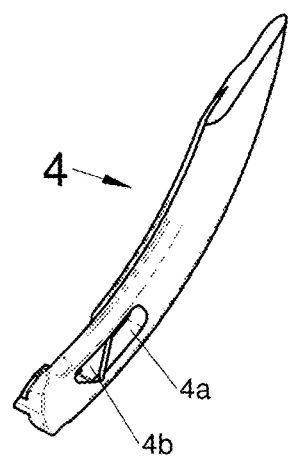
Figure 20A:
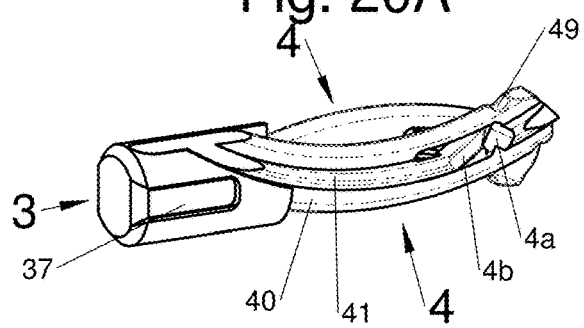
Figure 20B:
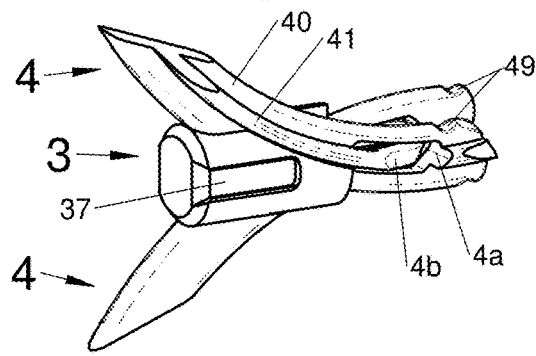
Figure 20C:
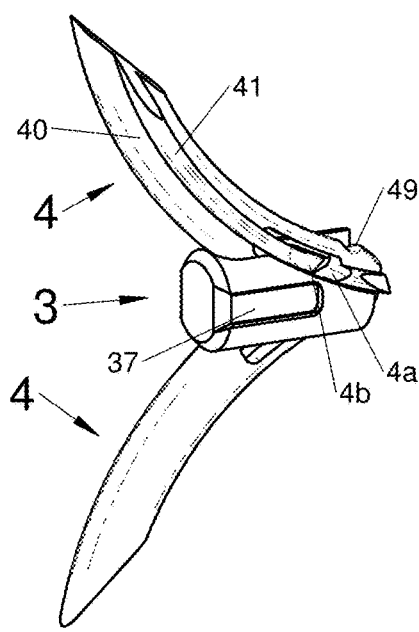
Figure 21A:
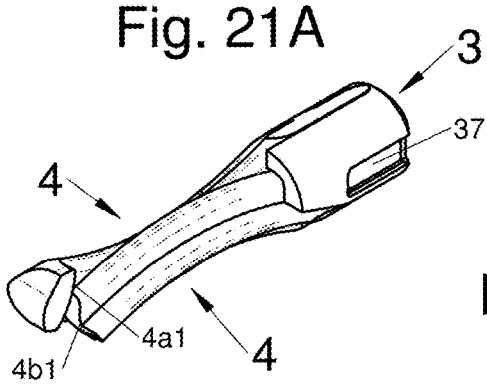
FIGS. 21A, 21B and 21C illustrate perspective views of an embodiment of a bone anchoring system, respectively before, during and after deployment of the anchors; the FIGS. 21D, 21E and 21F illustrate profile views of the posterior end of the anchors, respectively before, during and after deployment of the anchors.
Figure 21B:
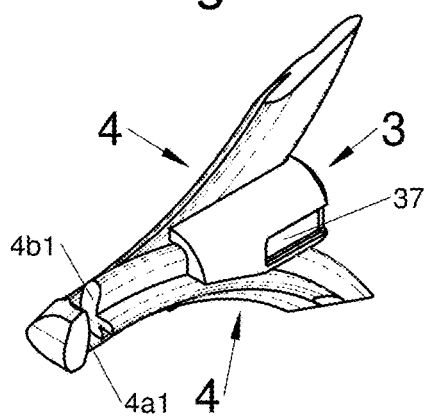
Figure 24A:
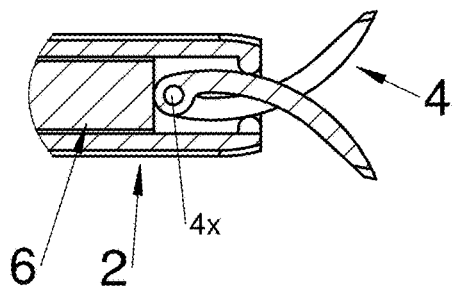
FIG. 24A illustrates a sectional view along a plane 24A-24A of the FIG. 24C of a bone anchoring system according to an embodiment comprising two deployed anchors, a support and an impactor; the FIGS. 24B, 24C and 24D illustrate perspective views of the anchoring system, respectively before introducing the anchors into the support and then during and after deployment of the anchors; and the FIG. 24E illustrates a perspective view of the posterior end of one of the anchors.
Figure 24B:
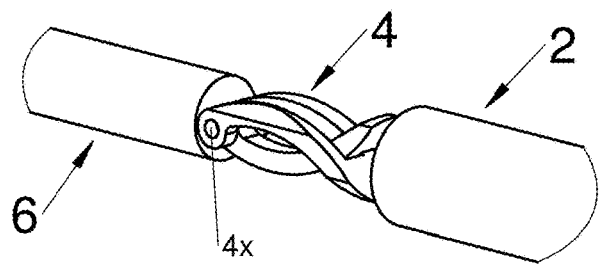
Figure 24C:
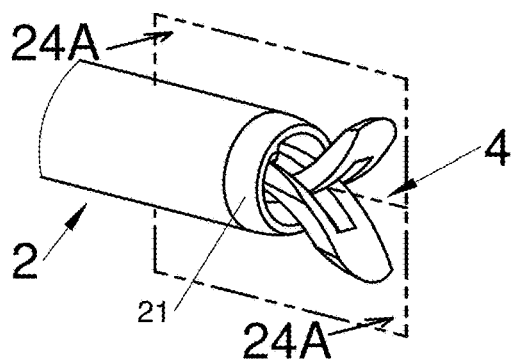
Figure 24D:
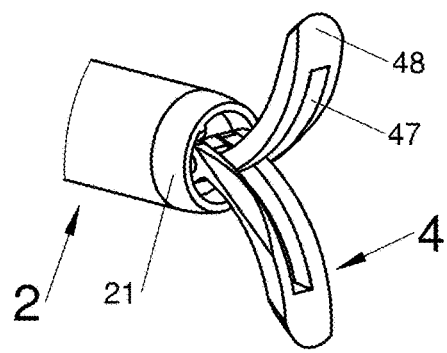
Figure 24E:
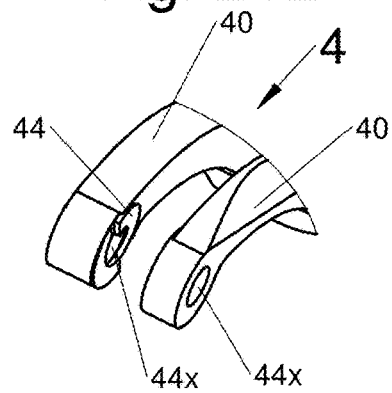

Moreover, some embodiments facilitate and/or make the implantation of anchors (4) reliable in the bone tissue, thanks to guidance of the anchor, achieved at least by a support (2) of the anchoring system and optionally by another element of the system, all along the path in this support (2), until the anchor penetrates the bone tissue. In some embodiments, this guidance is obtained by a "side by side" arrangement of two anchors, preferably with complementary shapes or even identical and arranged symmetrically with respect to the other, for example as illustrated in the FIG. 1B or 24B. On the other hand, this guidance may be obtained by the shape complementarily between the anchor or the anchors (4) and the inner walls of the conduit in the support (2), for example as illustrated in the FIG. 1E or 24D. Further, in some embodiments, the anchoring system further comprises a guide (3) for deployment of the anchors, for example as illustrated in FIG. 1B, 6D, 25C or 26E. This guide (3) is also used for reinforcing the reliability of the deployment of the anchors, for example by its shape complementarily. Indeed, this guide generally appears as a part, for example as a socket (full or hollow) of which the peripheral walls are configured in order to fit the shapes of the anchors, by allowing sliding of the anchors along the guide and thereby guiding the path of the anchors towards their implantation site. For example, grooves on the perimeters of the guide will be provided for guiding the sliding of the anchors towards their anchoring point in the bone tissue, by cooperating with the shape of the anchor (for example having ribs), for example as illustrated in the FIG. 15B, 20B or 21B. On the other hand, in some embodiments, additional guidance is provided by a fixation plate (1) of the anchoring system including guiding means. The fixation plate (1) is able to be placed bearing against the bone tissue (O) or an implant (7, P) or may be configured so as to be able to be assembled with said implant, by mutual complementary means of the implant and of the plate. On the other hand, the plate participates in the guidance of the deployment of the anchors of the anchoring device. Indeed, the fixation plate comprises for example and in a non-limiting way, at least one opening (14), the walls of which are complementary to those of the anchor, for example by forming grooves intended to fit the contours of the anchor or of the anchors which the plate is intended to receive. The FIGS. 2E, 2F and 2G show examples of such guidance of the anchors with the plate and it will be noted that the orientations of the anchors are different from one figure to the other in order to show this advantage which these embodiments have of a guidance by a plate. The FIGS. 5D, 5E and 5F show other guidance examples by a plate, but this time for four anchors (4) and without any guide (3) passing through the plate (1), unlike the examples of FIGS. 2E, 2F and 2G wherein the guide (3) facilitates guidance of the anchors in the plate and participates in the indexation of the orientation of the anchors by the shape complementarily of the peripheral wall of the guide (3) with the inner wall of the opening (14) in the plate (1). It will be noted that in the examples of the FIGS. 2E and 2F, the orientation of the anchors relatively to the plate and the guide may be set in an angular range determined by the shape of the opening (14) and the shape of the guide (3) and of the anchors (4) since the opening (14) of the plate allows adjustment of this orientation, while in the FIG. 2F, the opening allow only a single orientation which is therefore indexed and set to a single value, instead of being indexed in a range of values for example like in the FIGS. 2E and 2F. In particular, the FIG. 1C shows an example of this complementarily between the guide (3) and the plate (1), with a rib (37) in the peripheral wall of the guide (3) which cooperates with a projection (137) in the opening of the plate (1) allowing indexation of the orientation of the guide (3) and of the anchors (4) through the plate (1). It will be noted that the term of guide (3) has a functional definition and that the examples of structures provided as an example here should not be considered as limiting, but that the guide on the other hand necessarily has a particular shape in order to ensure its guiding function. Further, the plate term used here for designating another element of the system which contributes to the stability of the assembly in various embodiments, but this term and the shape examples provided should not be considered as limiting either since a plate may be provided in the form of a plate or parallelepiped or general cylinder or any shape capable of providing an opening for guiding the anchors, since this is also the main function of this plate. The plate also has the advantage of optionally being able to extend the contact surface area of the bone anchoring and facilitate the addition of other elements of the system, such as for example a particular implant. The final assembling between the anchor (or the anchors) and the plate is generally provided so that the plate remains outside the bone and retains the posterior end of the anchor while the anterior end and a major part of the latter has completely penetrated the bone. The plate therefore remains generally posterior to the anchor and to the other elements, while the guide (3) remains generally foremost, notably because it is sometimes provided for also penetrating the bone tissue itself.

Thus, in some embodiments, the support (2) of the anchoring system is able to cooperate with a fixation plate (1) and/or a guide (3) through cooperation means (12, 21, 13, 137), for example as illustrated in the FIGS. 1A and 1C. These cooperation means (12, 21, 13, 137) generally form coupling means for generally removably binding the elements or instruments together during surgery. This coupling often allow to arrange the elements or instruments relatively to each other, notably by indexing (and/or by adjusting) the orientations, notably the guiding means for the bone anchoring. Thus, by the terms of "cooperation" and/or "coupling" herein one refers to the fact of joining the elements by assembling them, or even by retaining one relative to the other. For example, the fixation plate (1) comprises at least one coupling means (12), such as a tapping or a recess or a raised part or an abutment for example, or any combination of this type of means. This cooperation means is provided so as to be complementary to at least one coupling means (21) of the support, for example formed by a threading or a raised part or a recess or an abutment, respectively or any combination of this type of means. On the other hand, when it is intended to be used in combination with a guide (3), the fixation plate (1) and the guide preferably comprise at least one mutual coupling means (13, 137). For example, a groove of the plate (1) may be provided for accommodating and guiding at least partially a guide (3). Further, in the embodiments where a loader is provided (5), the latter preferably comprises a hollow body giving the possibility of loading at least one anchor for introducing it into the support. This loader (5) therefore generally forms a means for coupling said anchor (4) with the support (2) into which it is intended to be introduced, since the anchor is loaded in the loader, for example via at least one loading opening (54), generally in the wall of the loader when the anchors are curved, for example as illustrated in the FIGS. 5C and 5D, although the anchors may also be loaded through one of the open ends of the loader generally. These loading openings (54) in the walls are provided with a complementary shape of the section of the anchors and the loader is generally provided according to the length and the shape (rectilinear or curved) of the anchors. Further, the loader also forms a means for coupling (in addition to guiding) the anchors between them when it is intended to load several of them at a time. Indeed, in most of the figures of the present application, the anchors are used pairwise and when a loader is used, it allows them to be maintained side by side, as thus the support (2) when the latter is provided for being used without a loader (5). On the other hand, in some embodiments, the loader (5) comprises coupling means (53) with the guide (3) for facilitating the mounting of the guide (3) on the loader (5), for example as illustrated in the FIGS. 1D and 1E. These coupling means (53) give the possibility that the guide (3) be retained on the loader (5) and that the anchors (4) may then be introduced into the loader, which facilitates the assembling as compared with other embodiments where the guide (3) has to be put at the end of the anchors (4) and then load the whole in the loader (5). A method for preparing the system may therefore include a step for coupling the loader and the guide (3) by means of such coupling means (53). On the other hand, in the embodiments using an impactor (6), the latter may simply be configured for pushing the anchors, but it is often provided that the anchors (4) are held by the impactor (6) by means of the mutual coupling means (46, 64, 460, 640), as detailed further on in the present application.

Deployment

In some embodiments, the anchors (4) are used at least pairwise, which has the advantage of providing a more stable and reliable anchoring, and/or of accelerating the surgical procedure, but various other advantages are also possible. In particular, during the combined use of at least two anchors, the latter may be provided with mutual locking means (42, 44, 4a, 4b, 46, 49) and allow their automatic blocking in the bone tissue once they have been impacted therein. On the other hand, the quality (reliability, stability) of the anchoring is often improved during the use of a combination of one or several anchors with each other, alone or combined with at least one guide and/or at least one plate. Indeed, when an anchor is used combined with a guide and/or a plate, it is often stabilized by this combination and the anchoring is thereby improved. Further, when two anchors are used in a combination with each other, their optional mutual locking gives the possibility of stabilizing them and of securing the bone anchoring, but their combination with a guide and/or a plate also allows this stability/security effect, even if they are not locked together, from the moment that they are retained by the guide and/or the plate. Finally, another stability advantage may be obtained by the orientation of both anchors used as a combination with each other, for example as illustrated in the FIGS. 26C, 27C, 28C showing illustrative examples of combinations of at least two deployed anchors in a single bone with different orientations (thanks to their curvature in these examples) which provide, through the divergent paths of both anchors inside a single and same bone, a particularly stable fixation, especially more stable than in diverse solutions of the prior art or for example in the case of a configuration of the type of the one of the FIG. 31E where each bone (in this case a vertebra) is only penetrated by anchors having substantially the same orientation and for which a backward movement is unlikely but less than in the configurations of the type of those of the FIG. 26C, 27C or 28C for example. Indeed, some embodiments provide that at least two anchors (4) are used at the same time and that the guidance means are provided for guiding the deployment of the anchors in different directions. When these anchors are deployed with different directions inside a same bone tissue (e.g., a same bone), the anchoring obtained is generally much more stable than when the anchoring is obtained along a single direction.

Further, the curved anchors are known for already improving the anchoring when the direction of the anchoring is not rectilinear and the advantage of using at least two anchors is therefore still more significant if at least one of the anchors is curved. It will be noted that these stability advantages are exclusively obtained if the anchoring is not achieved along a rectilinear path which, in the same direction as the one in which will be exerted the forces tending to withdraw the anchoring from the bone tissue. This is the case for curved anchors, but rectilinear but non-perpendicular orientations to the surface of the bone tissue are advantageous, for example like in the system illustrated in the FIG. 2A, 2B, 2C or 2D. Most of the figures of the present application moreover illustrate uses of several combined anchors, whether they are rectilinear, for example like in the FIG. 2A, 2B, 2C or 2D, or rather curved, for example like in all the other figures, but the present application may also relate to combinations of a single anchor (4) with at least one guide (3) and/or at least one plate (1) and/or with at least one support (2) for the implantation. Thus, in some embodiments, both anchoring devices (4) are arranged relatively to each other in a folded-back position when they are inserted into the support (2), and optionally inside the loader (5) and positioned in a deployed position when they are implanted in the bone tissue (O), for example through a plate (1) and/or on a guide (3). The non-collinear orientations between a first anchor and a second anchor and/or the guide (3) penetrating the bone and/or the direction in which are exerted the forces on the anchor ensure reliable bone anchoring. This is why various embodiments provide a deployment of the bone anchoring. The terms of "deploying" or "deployable" or "deployment" generally designate in the present application the fact that the bone anchoring extends over an area of larger dimensions inside the bone tissue than the dimensions of the entry point of this bone anchoring in this bone tissue. Thus, by deployment is meant the fact that the bone anchoring is provided by at least two structures which diverge inside the bone. This deployment may also relate to a divergent translation of two straight anchors and a sliding of two curved anchors which preferably each follow their radius of curvature, or a combination of a straight anchor and of a curved anchor. Further, this deployment may also relate to the pivoting of two curved anchors connected through a joint which is subject to translation towards the bone tissue. However, in the latter case, both anchors do not penetrate into the bone by following their radius of curvature and further they risk damaging the bone tissue and/or deforming during the deployment. Indeed, by observing for example the FIGS. 6B and 6C, it is seen that a curved anchor penetrating the bone tissue by following its radius of curvature will in fact have a curvilinear path which imposes that its posterior end does not move in translation towards the bone tissue but also follows this curvilinear path. Thus, the curved anchors have a curvilinear trajectory which implies that any point of the anchor in fact moves (ideally or substantially, since variations may naturally occur because of the hardness of the bone, with an unexpected movement during the implantation etc.) along the same curve as the one described by the anchor. In particular, as this is the anterior end which defines the entry point into the bone, the rest of the anchor will tend to follow its radius of curvature starting from this entry point, which in particular implies that the posterior end will move in the plane in which the radius of curvature of the anchor is included (where the radii of curvature of the anchor are included). The applicant therefore benefited from this observation for developing the present system which provides a particularly reliable fixation during deployment of at least two anchors which are free to move in the plane of their radius of curvature during the implantation for example as illustrated in a non-limiting way in the FIG. 5A to 5C or 9B to 9E of the present application. Indeed, by allowing the anchors to follow their radius of curvature, the penetration into the bone is facilitated and the anchoring is thus secured. Further, by letting the free anchor penetrate the bone along its radius of curvature, it is less likely to move during its entry into the bone and the entry point in the cortical bone is more accurate since its extent is minimized. Further, the anchor is less likely to move along this thereby specifically defined path, which limits the risks of movement of the anchor in the bone outside the space which it will occupy once deployment is complete. Moreover, if the anchors are locked (together and/or by an additional element) when they are completely implanted in the bone, the risks which may emerge inadvertently are considerably reduced since this would imply displacement of the anchors which does not coincide with the movement which they had upon penetrating into the bone. In order to come out, these anchors would therefore have to be deformed or the bone cut in order to allow such a movement. Thus, even if two curved anchors and bound through a posterior joint are contemplated in the present application, for example as illustrated in a non-limiting way in the FIGS. 24A to 24D, it is generally preferred that the anchors be free relatively to each other during their deployment and it is preferred that they be locked at the end of the deployment.

Thus, in various embodiments, the system comprises at least one deployment means (1, 2, 3, 6 and 8), generally obtained by the guiding means and by the arrangement of various elements or instruments between them, which allows the anchoring device (4) to be deployed in the bone tissue (O), by following a trajectory defined by at least one radius of curvature of the anchoring device (4). It will be noted that it is possible to provide curved anchors which have several radii of curvature, but for optimum deployment, these radii of curvature will preferably be quite close and allowed by the elasticity of the anchors, such as for example Nitinol, so that the advantageous phenomena of such a deployment are obtained as described above. In some embodiments, it is sometimes possible to benefit from this advantage of anchoring devices which do not deploy according to the trajectory defined by their radius of curvature, for example by preferably using them for an implantation in a spongy bone tissue. Indeed, in this type of configuration, for example as illustrated in the FIG. 24A, both anchors bound through a joint such as a pivot axis (4x) will penetrate the bone tissue at the same time and will be able to be deployed by diverging, one from the other but the axis (4x) will describe a translational movement and the curved anchors therefore do not describe a trajectory which follows their respective radius of curvature. This deployment of the anchors will have the consequences and drawbacks of deforming the anchors and/or of causing lesions of the bone tissue. If the bone tissue is compact, it risks splitting and it is therefore preferable to use this type of system in a spongy tissue (soft) where the lesion will have less risk of having detrimental consequences or even having, under some conditions, relatively beneficial consequences since this lesion may stimulate bone growth of the spongy tissue which will become more resistant at the end of the surgery and this bone growth.

It is understood that the present application optionally in particular relates to a system including two curved anchoring devices (4) each having at least one radius of curvature and positioned one beside the other inside the support (2), and optionally inside the loader (5), in a folded-back position in which their longitudinal axes are substantially parallel with each other, but their radii of curvature are oriented in different directions, so as to allow deployment towards a deployed position when they are implanted in the bone tissue (O).

In some embodiments, another advantage of stability can be achieved by the use of two anchors (or "anchors") in combination with one another, by automatic deployment of these anchors within the bone tissue once they have been impacted therein (for example through the support), and preferably only thanks to the hollow tube of the support, i.e. without requiring the use of any additional structure for deploying, guiding or locking on the anchors and/or the support. Indeed, as described above, the shape of the anchors enables them, on the one hand, to have different orientations (thanks to their curvatures) and divergent paths (i.e., trajectories) of deployment and, on the other hand, to move (i.e., be deployed) in the plane of their radius of curvature during the implantation. Thus, two anchors which are disposed facing each other (i.e., apposed) in a single conduit (channel or duct or tube; such as in the support) will cooperate or at least remain interconnected throughout the implantation. In this case, it is therefore not necessary to add additional means on the anchors and/or on the support, in order to keep the two anchors linked together during implantation in the bone tissue or to guide the deployment of the anchors along a predefined path. The anchors are shaped and dimensioned complementarily to the shape and dimensions of the channel or duct or tube, such that this complementarity alone may be sufficient to support and guide the anchors lying along each other, thereby facilitating their deployment along their radius of curvature. This configuration results in a stable and reliable anchoring into the bone tissue.

Locking

Figure 13A:
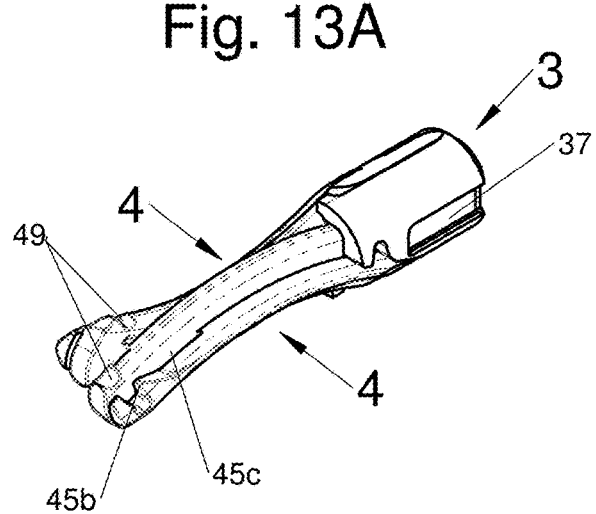
FIGS. 13A, 13B and 13C illustrate rear perspective views of an embodiment of a bone anchoring system, comprising two anchors retained by a guide at their anterior end, respectively before, during and after the deployment of the anchors; and the FIG. 13D illustrates a perspective view of both anchors.
Figure 13B:
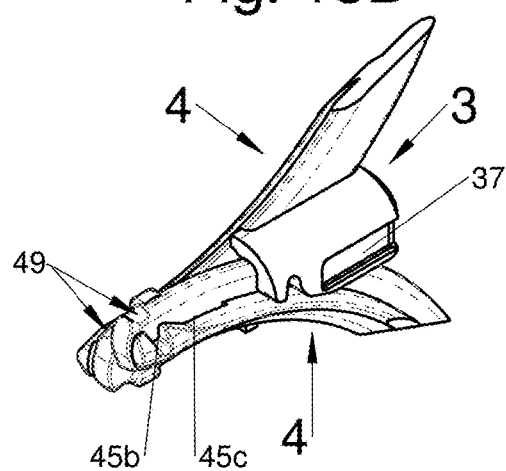
Figure 13C:
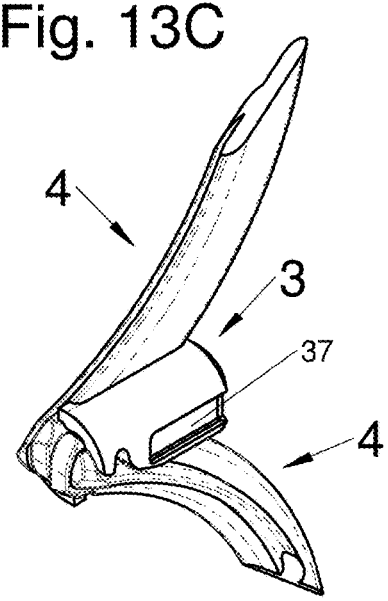
Figure 13D:
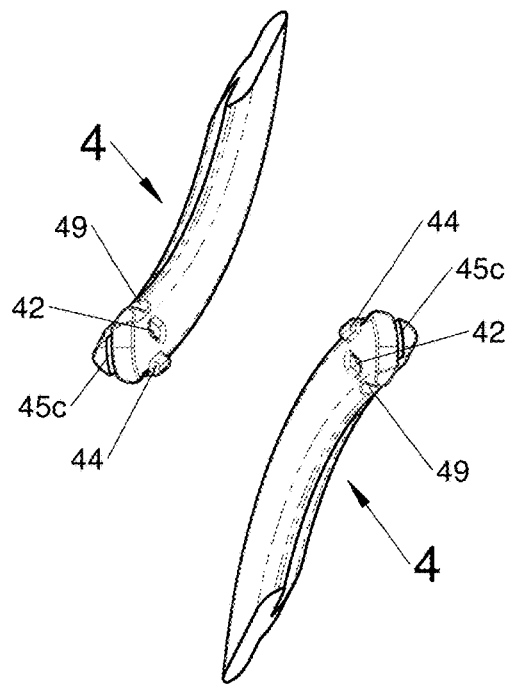

In some embodiments, the locking means the anchors are provided for securing the bone anchoring. After anchoring in the bone tissues, undesirable movements of the anchors, for example during movements of the patient, induce risks that these anchors move back and come out of the bone, which may cause significant damages for the patient. It is therefore useful to provide at least one mechanism for securing the bone anchoring, notably by locking the anchors. Various types of locking means are possible, notably for obtaining mutual locking of the anchors together and/or locking of at least one anchor with another element, instrument or implant of the system. It will be noted that these locking means the anchors together or with another element are not exclusive, as indicated by the term "and/or" and as explained generally in the present application for all the technical features which are detailed therein. Thus, for example, the FIG. 13D shows mutual locking means (42, 44) of both anchors which are compatible with the locking means the anchors (4) with the guide (3) such as those visible and demonstrated in the FIGS. 13A, 13B and 13C. Naturally, this is also obvious for the other types of locking means the anchors with another element and/or of mutual locking between two others elements, notably those described hereafter with reference to the other figures, unless the positions or arrangements of these two types of locking means are incompatible with each other.

Thus, in some embodiments, the system provides mutual locking means (42, 44) between two anchors, for example as illustrated in the FIG. 12E or 13D. These locking means (42, 44) for example include a male element (44) and a female element (42) which are complementary to each other, preferably at their posterior end or in proximity, arranged so that both anchors may freely deploy but automatically lock with each other when they are found in the final deployed position. It will be noted that these locking means (42, 44), alone or as a combination with other means on the anchors, may sometimes allow that both anchors are retained together also in a folded-back position. Indeed, in the illustrative and non-limiting example of the FIG. 12D, the male element of an anchor is initially accommodated in a housing (49) of the other anchor which is not intended for locking, but upon ablation (withdrawal of the anchor) as detailed elsewhere in the present application. Thus, both anchors, as for example visible in the FIG. 12A are initially maintained in a folded-back position (i.e., non-deployed) by the guide at their anterior end and by these complementary means at their posterior end (or in proximity thereto). During the deployment, the relative movement of the posterior ends ensures that the male element (44) of an anchor comes out of the ablation housing (49) of the other anchor, for example as illustrated in the FIG. 12B, which may for example be facilitated by a chamfer on an edge of the male element and/or by a slight gap between both anchors. Finally, at the end of the deployment, the anchors are provided so that their locking means (42, 44) are aligned and immobilize them in this position, which generally corresponds to an alignment of the whole of their posterior end, for example as illustrated in the FIG. 12D. The FIG. 12E illustratively and in a non-limiting way shows possible positions for these mutual locking means (42, 44) but many alternatives are possible and it is even possible to only provide one means, either male or female, for each anchor but this imposes the manufacturing of two anchors which are different from each other since complementary for this male or female means, unless this same single means includes a male portion and a female portion cooperating in the same way as two distinct means. As already explained with reference to deployment as defined above, this locking of both anchors together prevents the backward motion of an anchor relatively to the other when both of these anchors are deployed along two different directions, notably when they are curved and deployed along a path which follows their radius of curvature. Indeed, this backward motion (by following the same radius of curvature) imposes a relative movement of the anchors in the planes of their radii of curvature along trajectories which are different, since these planes are parallel with each other but the radii of curvature of both anchors are deployed in different directions. By preventing the relative movement of both anchors in these parallel planes, any movement of the anchors is prevented since these curvilinear trajectories are incompatible with a translational movement of the portions of the anchors (4) where the locking means (42, 44) are mutually engaged into each other. Further, this advantage is also obtained with straight anchors since this translational movement is also incompatible with the two rectilinear trajectories of both anchors, considering that these trajectories are not colinear or even parallel. It is understood that this mechanism is particularly advantageous since it represents a reliable solution at a low cost, not requiring any additional part for locking the whole of the anchoring device.

Figure 20D:
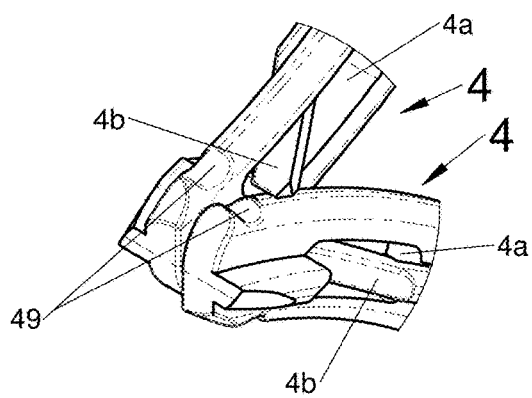

In some embodiments with mutual locking, for anchors used pairwise and positioned in contact with each other, each of these anchors (4) includes at least one tab (4*b*) emerging from a cut out of the anchor (4) and exceeding out from the face of the anchor (4) intended to be positioned in contact with the other anchor (4). These tabs (4*b*) form mutual locking means of both anchors in deployed positions. In some of these embodiments, comprising examples which are illustrated in the FIGS. 20E and 20F, these anchors (4) comprise, on at least one posterior portion, at least one opening (4*a*), preferably crossing the whole of their length, and the tab emerges from the inside of this opening (4*a*). In these embodiments, the tab (4*b*) of an anchor is configured so as to be folded back into the opening (4*a*) during the deployment of the anchors and for being locked on the other anchor (4), for example at an edge of the anchor on a posterior portion, for example as illustrated in the FIG. 20D.

Figure 21C:
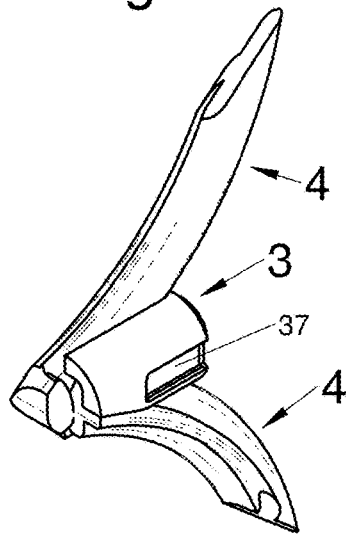
Figure 21D:
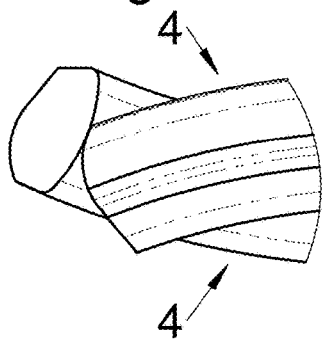
Figure 21E:
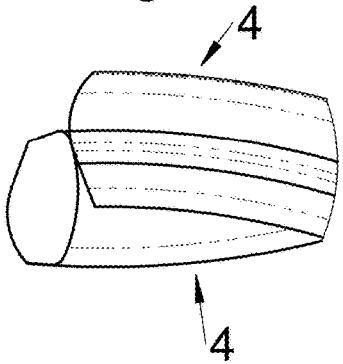
Figure 21F:
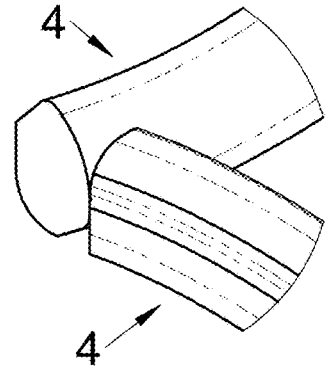

In some embodiments, one of the two anchors (4) is longer than the other one, notably but not exclusively in the case of a curved support (2) and/or loader (5). The longest anchor includes a long posterior end and holding back forming an abutment surface (4*a*1) for the posterior end (4*b*1) of the shortest anchor, for example as illustrated in the FIGS. 21A, 21B and 21C. Thus, the anchor with the abutment end (4*a*1) locks the shortest anchor by preventing it from moving backwards. The longest anchor, when it is provided with a distinct locking means, for example for locking it on a guide (3) or a plate (1), therefore allows to retaining both anchors. It will be noted that when these two anchors are curved and intended for a deployment as defined in the present application, the long end folded-back end will preferably have its abutment surface (4*a*1) complementary to the shape of the posterior end (4*b*1) of the shortest anchor so as to allow relative movement of both anchors by avoiding that both ends be damaged by their contact, for example as illustrated in the FIGS. 21D, 21E and 21F.

Figure 15C:
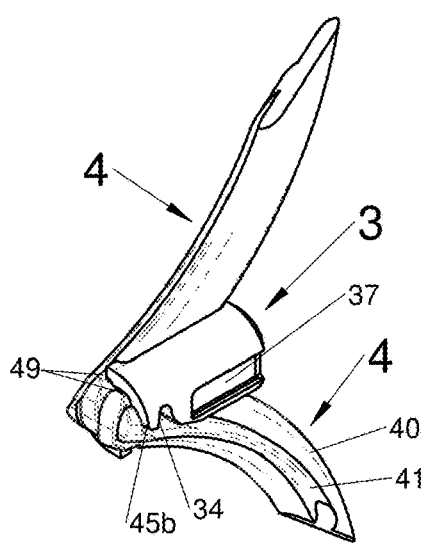
Figure 15D:
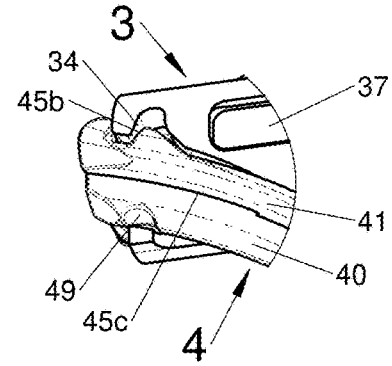
Figure 15E:
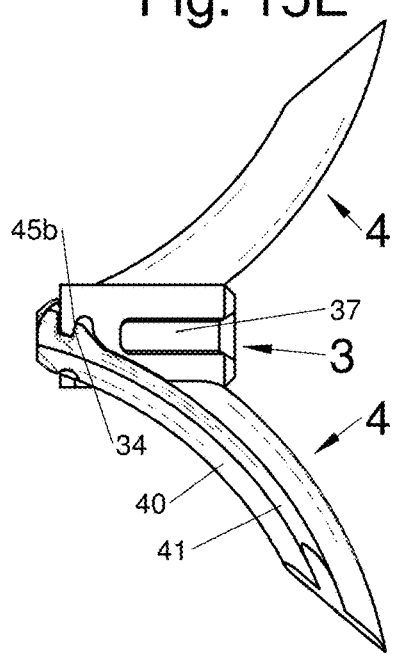
Figure 15F:
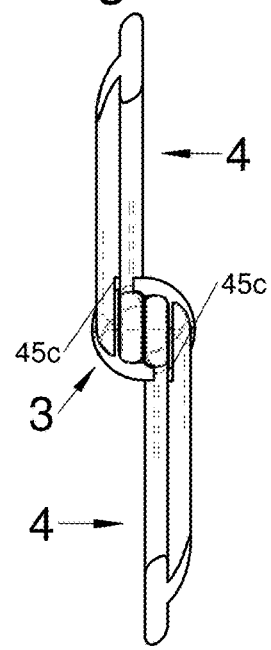
Figure 17A:
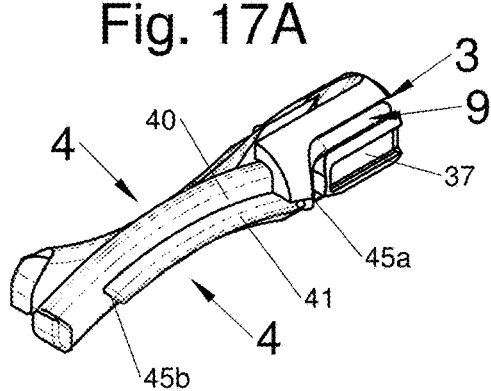
FIGS. 17A, 17B and 17C illustrate perspective views of an embodiment of a bone anchoring system, comprising anchors retained by a guide provided with a locking means, respectively before, during and after deployment of the anchors; the FIGS. 17F and 17G illustrate profile views of this system, respectively after and before deployment of the anchors; and the FIGS. 17D and 17E illustrate perspective views, respectively, of the posterior end of the anchors locked on the guide and of the locking means alone.
Figure 17B:
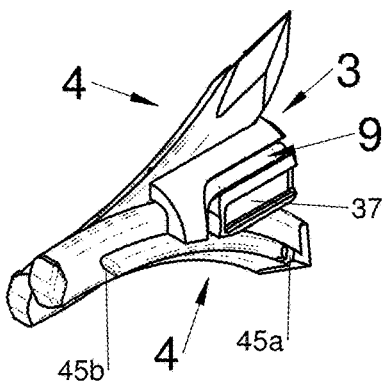
Figure 17C:
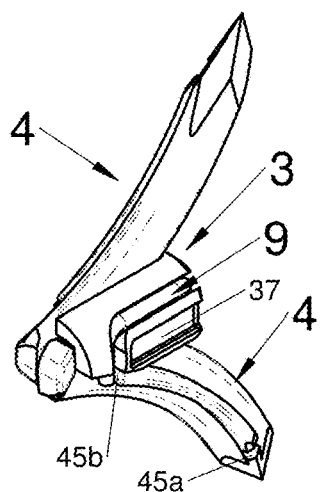
Figure 17D:
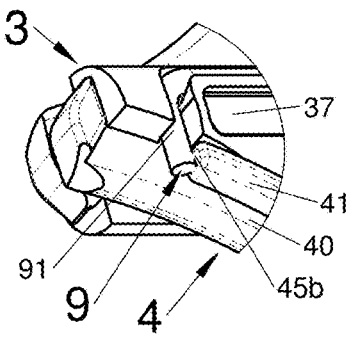
Figure 17E:
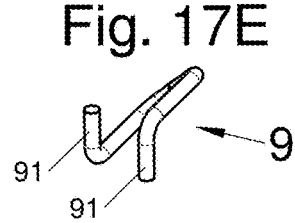
Figure 17F:
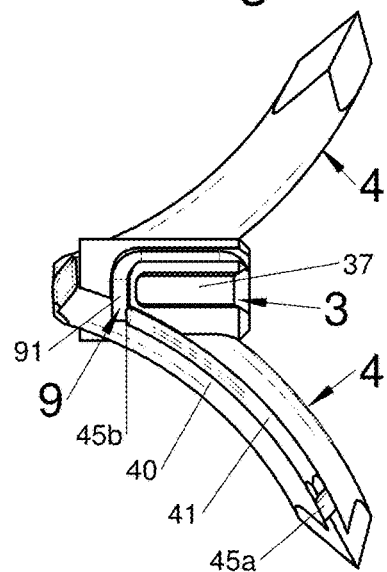
Figure 17G:
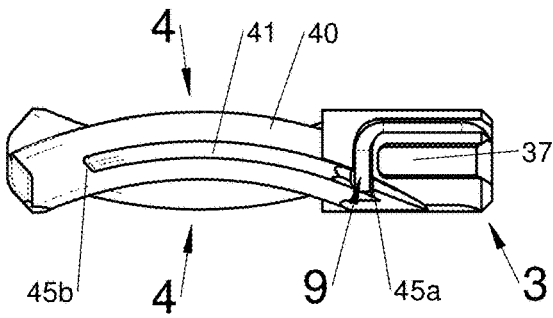
Figure 19A:
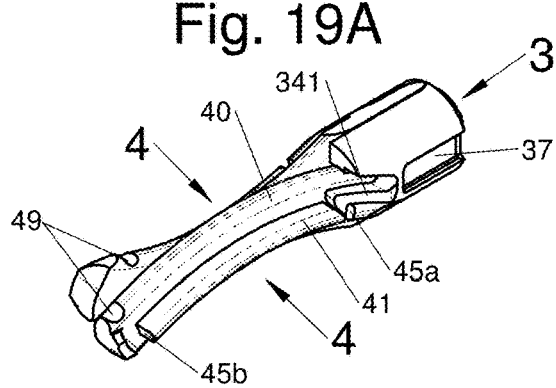
FIGS. 19A, 19B and 19C illustrate perspective views of an embodiment of a bone anchoring system, comprising two anchors retained by a guide comprising a locking means respectively before, during and after deployment of the anchors; the FIGS. 19E and 19F illustrate profile views of the system, respectively after and before deployment of the anchors; and the FIG. 19D illustrates a perspective view of the posterior end of the deployed anchors and locked on the guide.
Figure 19B:
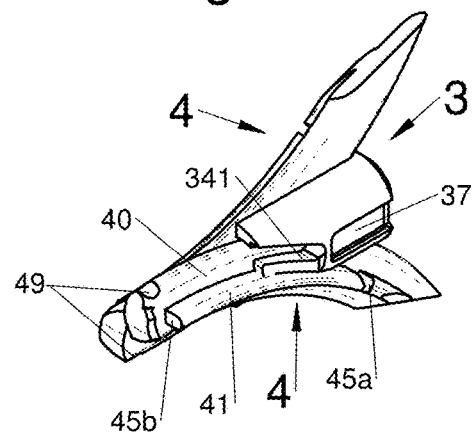
Figure 19C:
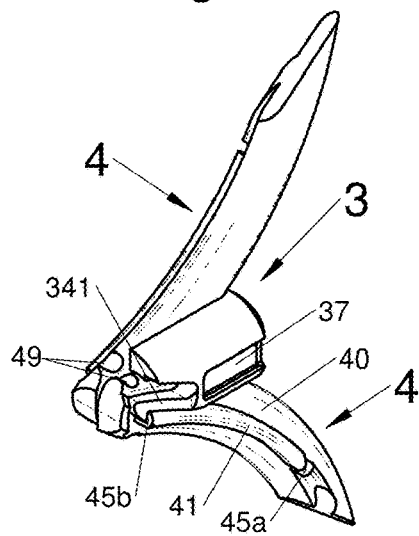
Figure 19D:
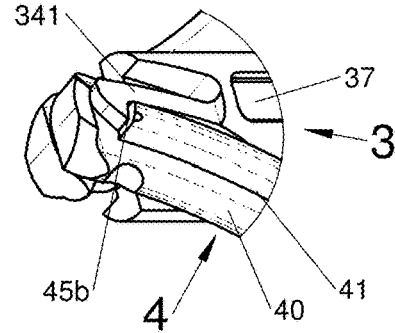
Figure 19E:
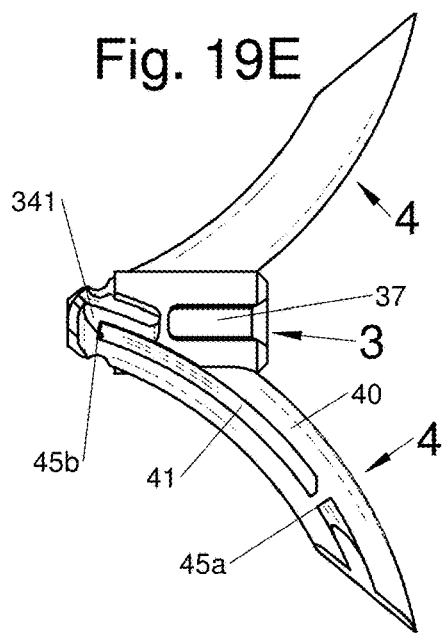
Figure 19F:
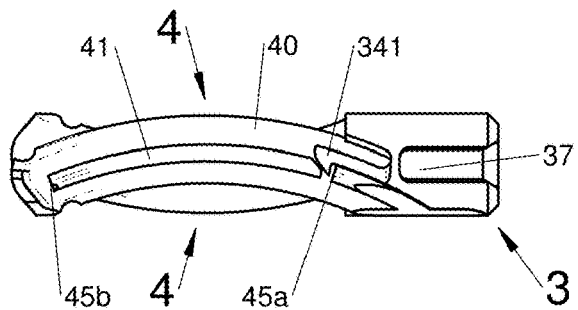

On the other hand, in some embodiments, the anchors (4) comprise locking means (45*a*, 45*b*, 45*c*) generally cooperating with complementary means (not shown) of the plate and/or cooperating with complementary means (34, 341) of the guide (3) and/or cooperating with at least one lock (8, 9, C, 10). For example, in some embodiments, the guide further comprises a locking means (34), for example a protruding end, able to be accommodated in a notch (45*b*, 45*a*) present at the surface of the anchors for locking them and maintaining them either in a folded-back position, for example as illustrated in the FIGS. 17A and 17B, or in a deployed position, for example as illustrated in the FIGS. 13C, 15C and 15D. In these examples, the locking means (34) is accommodated, when the anchors are in the folded-back position, in a notch (45*a*), for example as illustrated in the FIGS. 17A, 17B, 19A and 19F located at the anterior end of the anchor or in proximity thereto and when the anchors are in a deployed position, the locking means (34) is accommodated in a notch (45*b*) at the posterior end of the anchor or in proximity thereto, for example as illustrated in the FIGS. 15E and 19E. In some embodiments, the guide (3) comprises on at least one posterior portion, a hook (341) able to be accommodated in a notch (45*b*) of the anchor, for example as illustrated in the FIGS. 19A to 19C. In this embodiment, the anchors are locked and maintained in position as deployed anchors, for example as illustrated in the FIG. 19D. These two types of locking examples of the anchors with the guide (3) are purely illustrative and non-limiting. For example, the locking means (45*a*, 45*b*) of the anchors may be male or female elements as long as they are complementary to those of the guide (3) and/or of the plate (1). In some of these embodiments, the locking mechanisms (45*a*, 45*b*) of the anchors are positioned at the end of a portion cut out in the anchor, through a slot (45*c*) running along the body of the anchor, preferably in the direction of its length, for example as illustrated in the FIGS. 13A and 13D or 15A or 15F. This cut out or slot (45*c*) gives the possibility of providing elasticity facilitating the automatic locking and also facilitating the unlocking for example in the case of ablation (i.e., withdrawal of the anchors out of the bone tissue) if necessary. Preferably, this cut out or slot (45*c*) is made at the junction between the plate (40) (or the body) of the anchor (4) and the rib (41) (or the second plate) of the anchor, or even directly in this rib (41) or this second plate, in order to avoid making the anchor (4) fragile in portions which may be urged by the forces related to impaction or once set into place in the patient. In some embodiments, the guide (3) comprises an additional lock (9), for example as illustrated in the FIG. 17E. This lock is preferably accommodated inside a housing or a groove of the guide, which improves the locking since it is obtained with a lock which is in contact with the guide and will be less subject to shearing and therefore less brittle. This lock (9) comprises a protruding end (91) capable of being accommodated in a notch (45*b*, 45*a*) of the anchors so as to lock and maintain the anchors either in the folded-back position or in the deployed position. An illustrative and non-limiting example of this type of embodiments is illustrated in the FIGS. 17F and 17G, with the protruding end (91) of the locking means (9) accommodated in an anterior notch (45*a*) when the anchors are in a folded-back position and accommodated in a posterior notch (45*b*) when the anchors are in a deployed position.

Figure 11A:
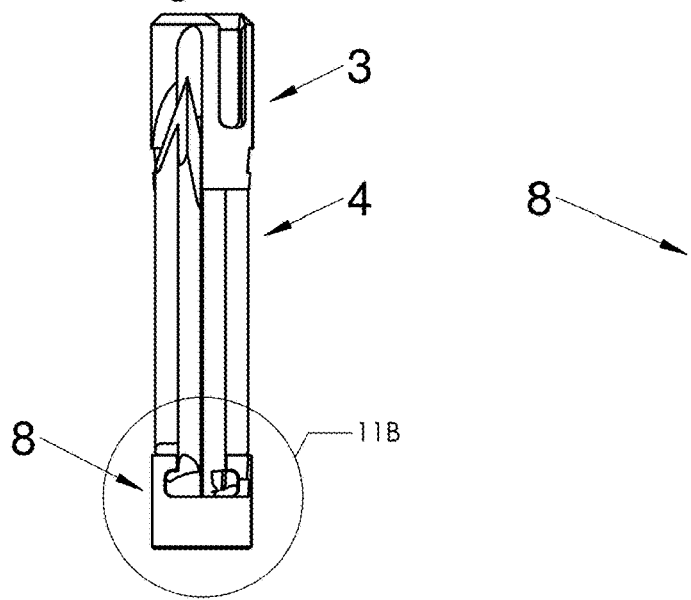
FIG. 11A illustrates a profile view of an embodiment of a bone anchoring system, comprising two anchors retained at their posterior end by a retaining element on the one hand, and at their anterior end by a guide on the other hand; the FIGS. 11C, 11D and 11E illustrate front perspective views of the system, respectively before, during and after the deployment of the anchors; the FIG. 11B illustrates a profile view of the posterior end of the anchors retained by the retaining element itself retained by the guide.
Figure 11B:
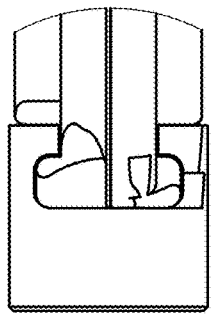
Figure 11C:
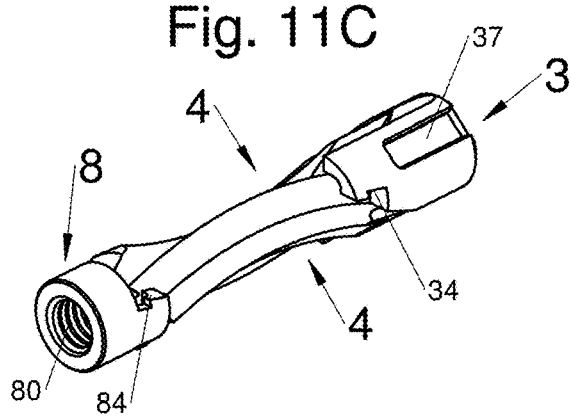
Figure 11D:
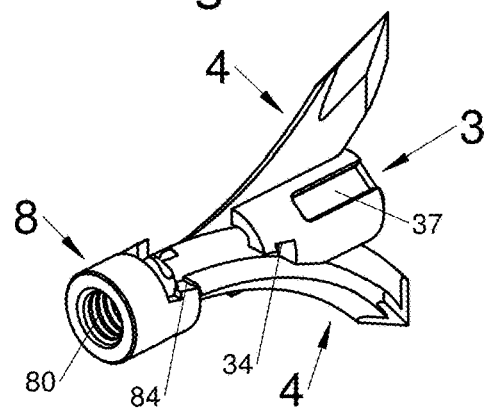
Figure 11E:
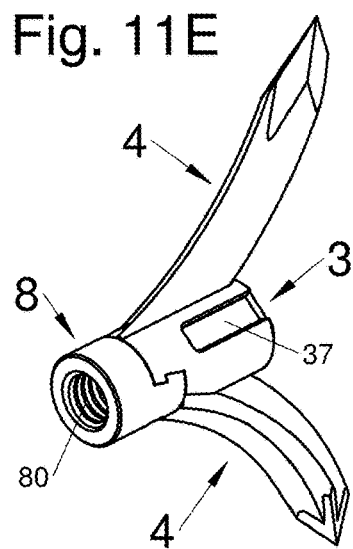
Figure 18A:
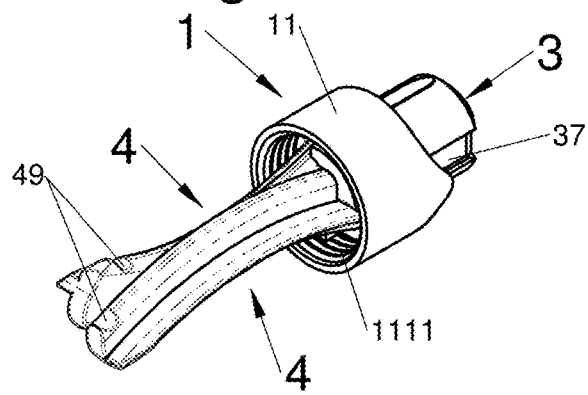
FIGS. 18A and 18B illustrate perspective views of a bone anchoring system according to an embodiment comprising an fixation plate, two anchors and a guide, respectively before deployment of the anchors and after deployment but before locking by a locking means; the FIGS. 18C and 18D illustrate respectively a perspective view and a sectional view along the plane 18D-18D of the FIG. 18C, of the anchoring system with the locking means locked on the fixation plate.
Figure 18B:
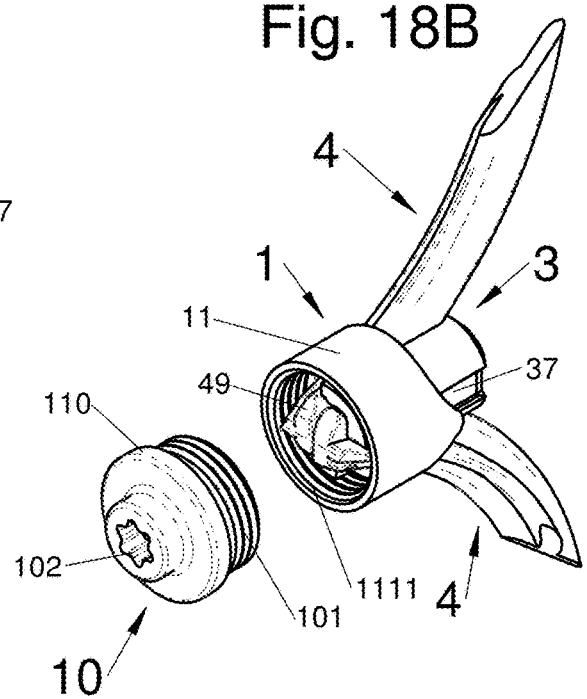
Figure 18C:
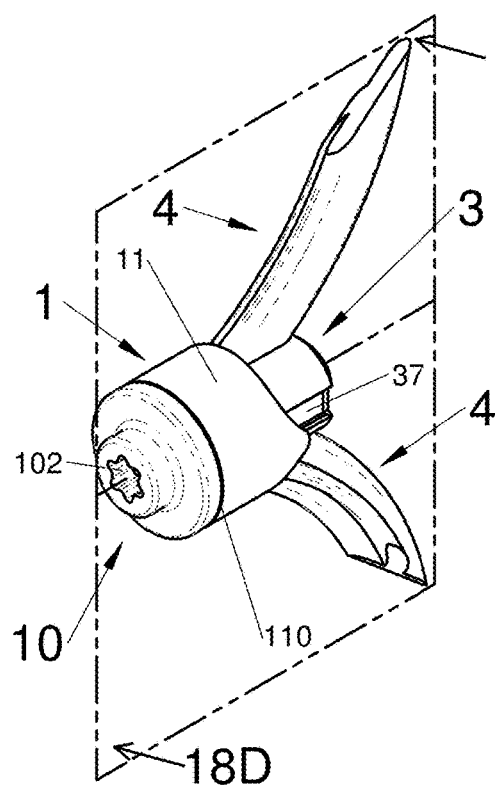
Figure 18D:
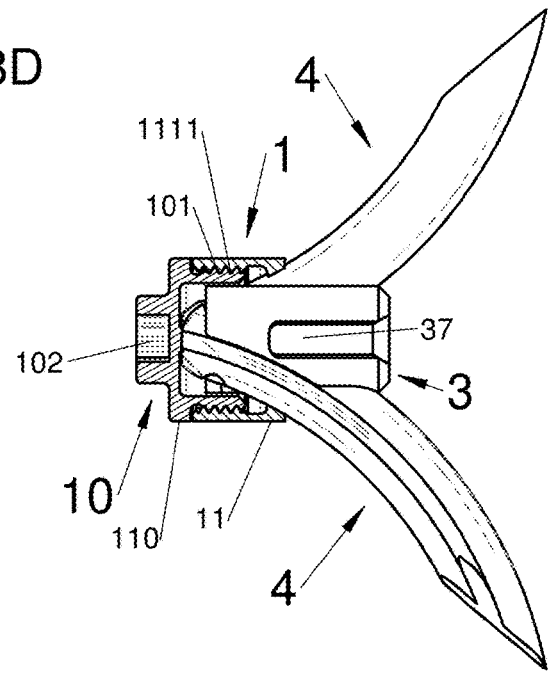

In some embodiments, the anchoring system further comprises a retaining element (8) giving the possibility of preventing the withdrawal on the one hand and the moving back of an anchor relatively to the other one so as to facilitate and maintain the deployment of the anchors, and of gripping the anchoring device with a gripping tool so as to introduce and/or withdraw the anchoring device. As particularly illustrated in the FIGS. 9B, 10C, 11B and 14A, both anchors of the anchoring device are retained by the retaining element (8) at their posterior end. This embodiment has the advantage of retaining the anchors together so as to prevent any backward or withdrawal movement of one anchor relatively to the other before and after deployment of the anchors. Also, in some embodiments where two anchors (4) are retained by at least one retaining element (8), for example as illustrated in figures of plates 9 to 11 and 14, the retaining element (8) forms an additional lock since it comprises locking means (84) giving the possibility of locking the anchoring devices to each other, when they are deployed. This retaining element is also a means for ablation of the anchoring device, so as to be withdrawn from the bone tissue by an ablation tool. In some embodiments, the retaining element (8) comprises a ring-shaped body arranged around or in proximity to the posterior end of the anchoring device (4). In some embodiments, the retaining element (8) comprises an external threading (80), for example as illustrated in the FIGS. 10A to 10E, or an internal tapping, for example as illustrated in the FIGS. 11C to 11E, with another instrument (1, 5, 6, 10) of the instrumentation. In some embodiments, the retaining element (8) comprises a groove (81) cooperating with a raised part (31) of a fixation plate (1), for example as illustrated in the FIGS. 14A to 14E (a sort of elastic circlips), so as to lock the fixation with the retaining element when the anchoring devices are deployed. In some embodiments, the retaining element (8) may cooperate with a locking means (10) for example as shown in FIG. 18B allowing hermetical locking of the anchoring device assembly (4) and retaining element (8) after implanting this assembly in the bone tissue (O). Thus, the retaining element (8) is an additional instrument giving the possibility of locking the posterior end of the anchoring devices on the one hand so as to facilitate their implantation by the impactor in the bone tissue, and withdraw the implanted anchoring devices of the bone tissue, when this is necessary.

Figure 16A:
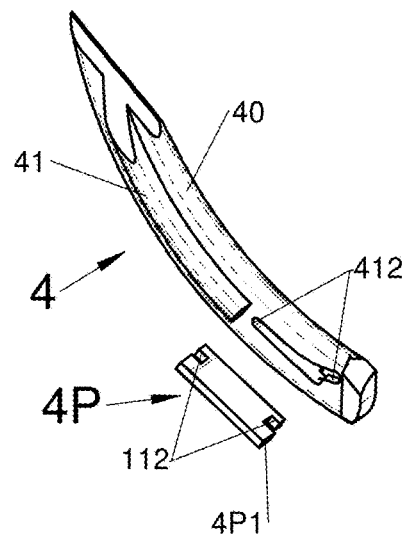
FIGS. 16A, 16B and 16C illustrate perspective views of an anchor of an embodiment of a bone anchoring system, with a retaining wing, respectively brought out, retracted and in a locked position in a housing of the posterior end of the anchor; the FIGS. 16D and 16E illustrate perspective views of the anchors retained by a guide according to this embodiment, respectively, before and after deployment of the anchors; the FIG. 16F illustrates a profile view of the posterior end of this system after deployment of the anchors.
Figure 16B:
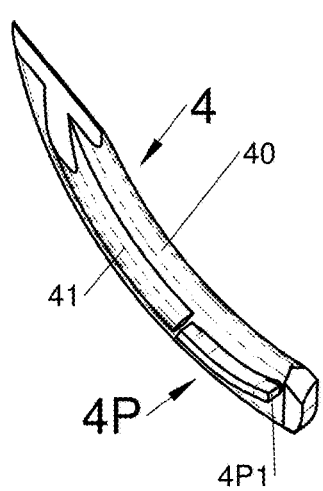
Figure 16C:
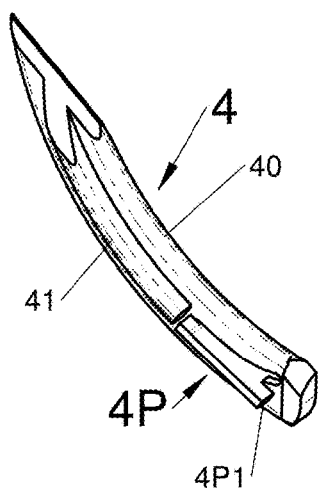
Figure 16D:
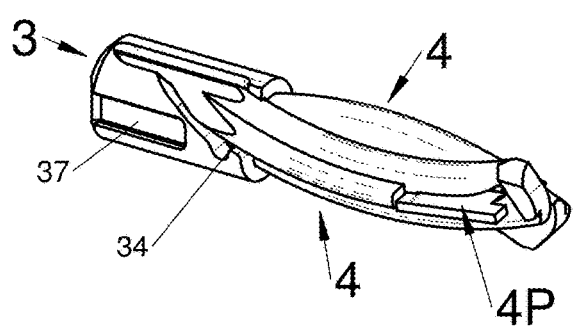
Figure 16E:
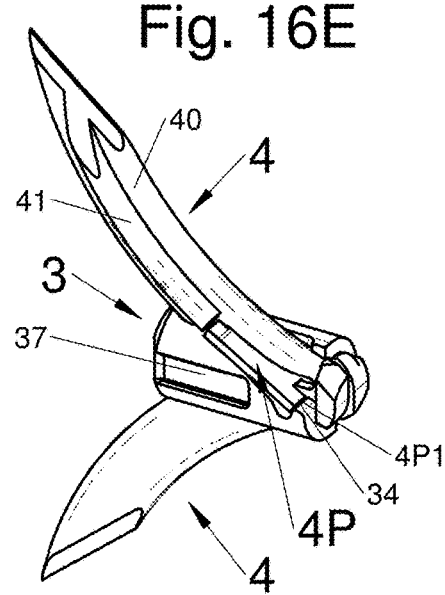
Figure 16F:
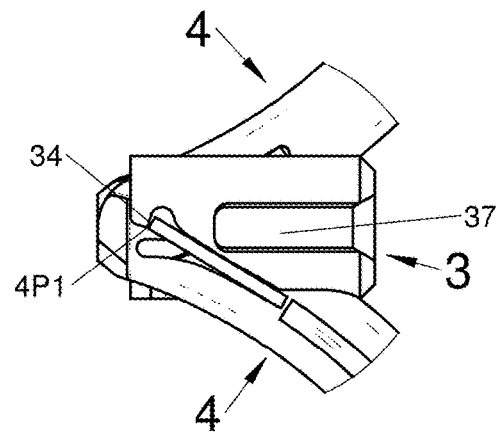

In some embodiments, an example of which is illustrated in the figures of plate 16, the locking of the anchor (4) with the guide (3) (or the plate) is obtained by means of a fin forming an additional lock, for example cooperating with the locking means (34) of the guide (3). The anchor (4) then comprises an opening (412) or a recess (412), on at least one posterior portion, able to receive a part or a fin (11, 111, 112). The part (11) fits into the opening (412) of the anchor through a tab (112) so that a tab (111) arranged outside the anchor is in abutment in a notch (34) of a guide (3). This gives the possibility of locking the anchor with the guide in a deployed position, for example as illustrated in the FIG. 16F. This solution gives the possibility, by adding an elastic fin, for example in Nitinol, of using a material for which the elastic characteristics are particularly adapted to the targeted function, which gives the possibility of limiting the dimensions of the cut outs in the anchor and of avoiding making it fragile.

Figure 22A:
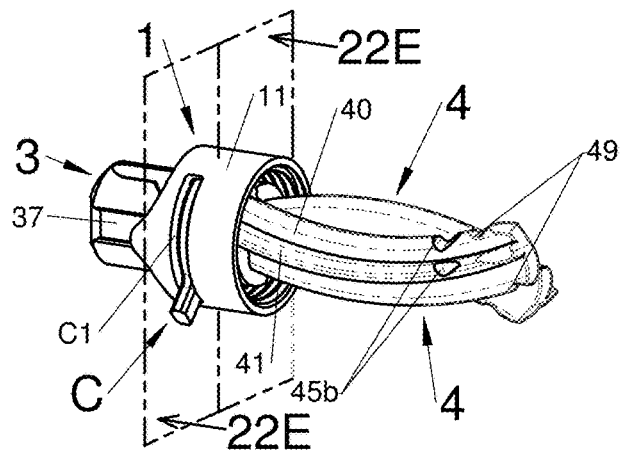
FIGS. 22A and 22B illustrate rear perspective views of a bone anchoring system according to an embodiment comprising two anchors, an fixation plate, a guide and a locking means, respectively before and after deployment of the anchors; the FIGS. 22C and 22D illustrate front perspective views of this system in which the plate has been omitted for more clarity, respectively before and after deployment of the anchors; the FIGS. 22E and 22F illustrate sectional views, respectively along the plane 22E-22E of the FIG. 22A and along the plane 22F-22F of the FIG. 22B, of this system, with the locking means in position, respectively, before locking and after locking.
Figure 22B:
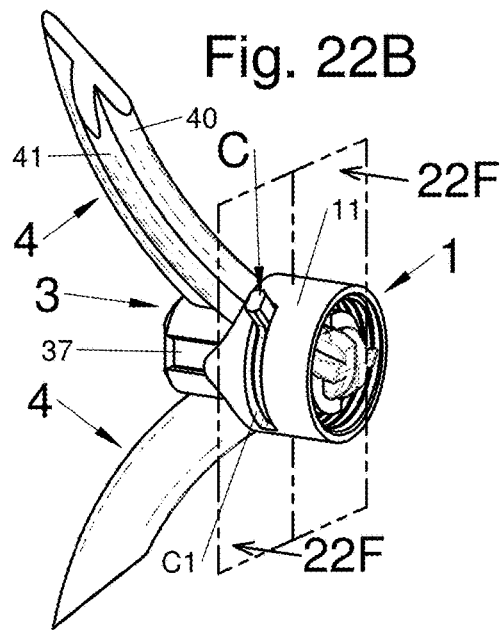
Figure 22C:
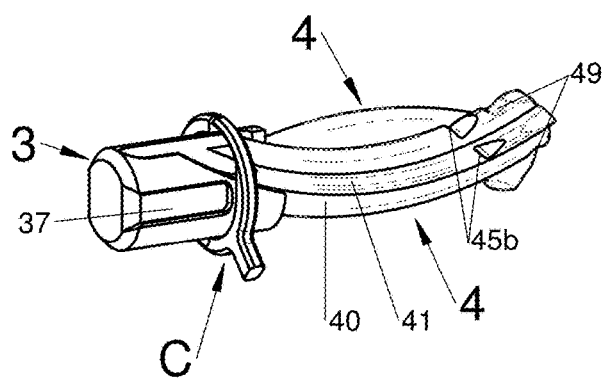
Figure 22D:
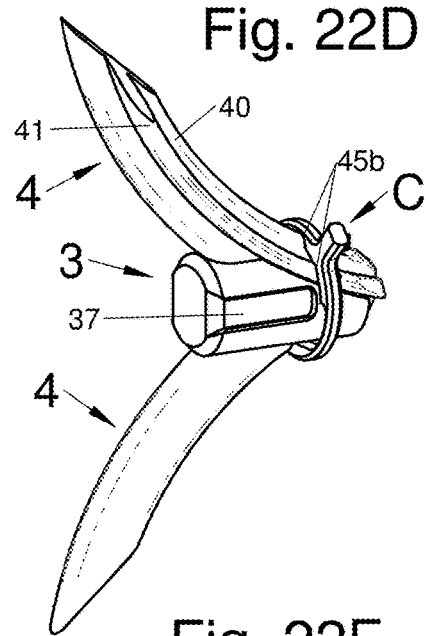
Figure 22E:
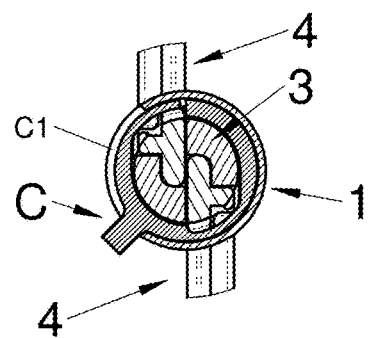
Figure 22F:
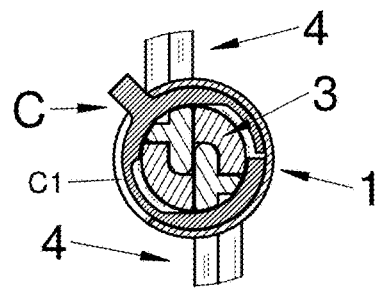
Figure 23A:
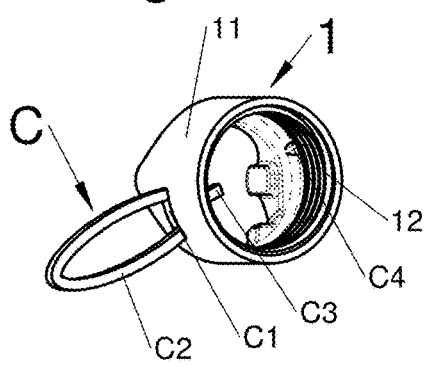
FIG. 23A illustrates a perspective view of an embodiment of a bone anchoring system comprising an fixation plate provided with a locking means; the FIGS. 23B, 23C and 23D illustrate perspective views, with a transparent portion, of the anchoring system completed with two anchors and a guide, respectively before, during and after deployment and locking of the anchors.
Figure 23B:
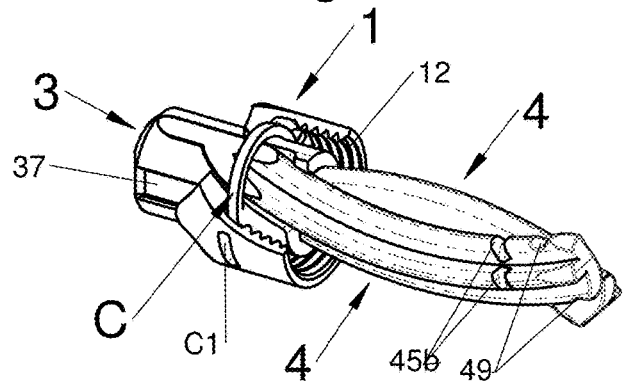
Figure 23C:
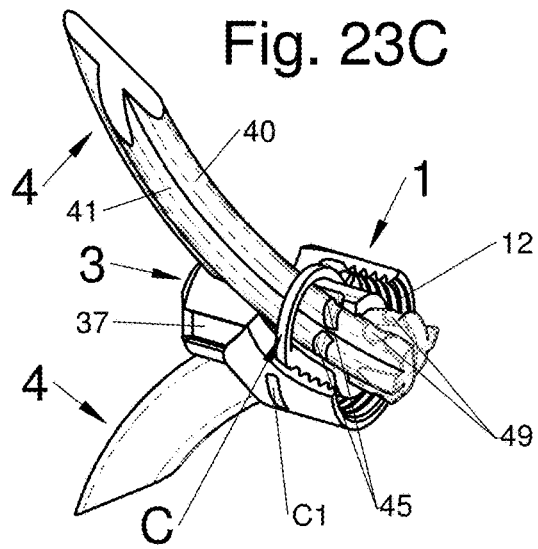
Figure 23D:
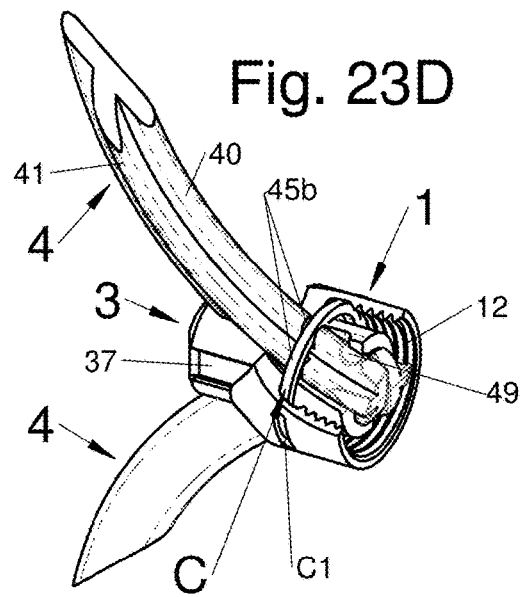

In some embodiments, the anchoring system further comprises a locking means (C), for example as illustrated in the FIGS. 22B, 22D and 23D. In this type of configuration, a fixation plate (1) comprises an additional locking means (C) also preventing withdrawal of the deployed anchors from each other. The FIGS. 22C and 22D more visibly show the locking by omitting the fixation plate. The locking means (C) also gives the possibility of locking the posterior end of the anchoring device with respect to the fixation plate, when the former is deployed and anchored in the bone tissue. This locking means (C) is for example formed by a ring or a split or open ring such as a circlip, able to be accommodated in a notch (45b) of the anchoring device (4) for locking its position with respect to that of the plate (1). It will be noted that the locking means where an element will be accommodated in a notch or a housing of another element, are not only very robust but generally allow locking in both directions, i.e. they prevent the anchors from advancing too much into the bone, in addition to preventing their withdrawal.

In some embodiments, the anchoring system further comprises a closing means (10), generally forming an additional lock, for example as a plug or a similar structure, giving the possibility of hermetically closing the posterior end of the anchoring device at the end of anchoring and when the anchors of the anchoring device are deployed. Indeed, without this closing means (10), a bone growth may obstruct the posterior end of the anchoring device, an end which comprises gripping means for withdrawing if need be the anchoring device. Indeed, bone regrowth in the posterior end of the unprotected anchoring device, makes its withdrawal difficult when ablation of the anchoring device is necessary after several months of implantation of the anchoring device in the bone tissue. This closing means (10) has a second advantage which is to block the assembling (suppress all the residual gaps) of the different instruments and implants (the anchors, the socket, the retaining element and/or the implant) at the end of the surgical operation. In some embodiments, for example as illustrated in the figures of plate 18, the closing means (10) is locked on a fixation plate (1), for hermetically closing and protecting the locking of the deployed anchors on the one hand, and for preventing the withdrawal of the locked and deployed anchors from each other on the other hand. In some embodiments, not shown in the figures, the closing means (10) may also be locked on a retaining element (8), illustrative examples of which are detailed hereafter, so as to fulfill similar functions, i.e. protect and prevent the withdrawal of the thereby locked anchors and/or avoid bone growth in the retaining element (8).

Anchor

In some embodiments, the anchoring device comprises either anchors as nails or even as screws (for example as illustrated in the FIGS. 2A and 2B), or elongated anchors, for example as a plate, for example a split plate (for example as illustrated in the FIGS. 2C and 2D), or curved anchors, for example as a plate or nails (for example as illustrated in the FIGS. 2E to 2G). Each type of anchor of the anchoring device is preferably used by the surgeon according to the desired application, as already known in the prior art and by one skilled in the art. Preferably, at least one curved anchor is used in the present application for the bone anchoring by means of deployment in a bone tissue, as detailed above. This configuration has the advantage of using less instruments than generally required and of reducing the time and the cost of a surgical operation. Preferably, the anchor has a sharpened anterior end in order to better penetrate the bone tissue. For example, a bevel or a chamfer made for producing sharp edges gives the possibility of facilitating the penetration and reinforces their anchorings in the bone tissue. In some embodiments, the anchor (4) may include at least one plate (40) or have the shape of a nail with a rounded or polygonal section, but may also have the shape of a staple. Generally, the anchor will be curved for improving reliability and facility of the bone anchoring.

For example, in the case of the use of a system for bone anchoring of a spinal implant, it will be generally provided that the anchoring device (4) be implantable in a bone tissue (O) according to an approach axis forming with the vertical axis of the rachis an angle of approximately 90°, by having its longitudinal axis substantially in the plane of the space of the bone tissue. As mentioned earlier, notably in the case of anchors in Nitinol, some embodiments in fact provide a different radius of curvature from one anchor to the other and/or several different radii of curvature on various portions of the body of a given anchor (4). Thus, for example, the body of the anchor (1) may have the shape of a circular arc or an elliptical arc. In the present description, the terms of "circular arc" or "radius of curvature", in fact correspond to the whole of these different possibilities. Thus, some embodiments of the present invention provide different alternatives as regards the radius of curvature and some aspects related to the anchoring device (4), as well as implants (7) and instrumentation which may be associated therewith. Indeed, for example depending on the use of the anchoring device and notably on the intended localization in a given bone or in the rachis for example, it may be preferable to have a more or less significant radius of curvature. Depending on the radius of curvature of the anchoring device, the axes respectively passing through the anterior end and through the posterior end of the device form an angle, typically comprised approximately between 90° and 180° although it is also possible to select it to be less than 90°. Preferably, this angle will be comprised between 110° and 160° which, under many circumstances will facilitate the implantation of the device (better than an angle outside these values). Depending on the fixation which is desirably obtained by means of the anchoring device, a more or less open angle will be selected. For example if a firm and solid fixation of the implant against the bone tissue is desirably promoted for example, an angle comprised between 120° and 180° may be preferred, while if the intention is rather to avoid displacement of the implant in the plane substantially parallel to the surface of the bone, an angle comprised between 90° and 150° will be preferable. Although these variations of the angle are not shown in the figures, different angles for the anchoring device thus give the possibility of covering the different desirable types of anchoring, in order to ensure a fixation, notably of the implants by adapting the system according to the needs.

In some embodiments, the anchoring device is rigid. The rigidity of this type of anchor allows efficient fixation, generally more efficient than staples or others thin and/or relatively flexible devices, or even fragile. However, some elasticity is tolerable in many cases and the rigidity is not indispensable in the system of the present application although it is advantageous in many cases. In some embodiments, the anchors penetrate the bone tissue through a passage (72) or a housing crossing at least one portion of an implant to be fixed. The rigidity of the anchor gives the possibility of crossing the implant without undergoing any deformation and therefore providing a reliable fixation since the portion of the anchor which remains in the implant has less risk of allowing undesirable movements than when it was flexible. Thus, it is also possible to provide an anchor, for which only the end intended to remain in the implant is rigid. Often the anchor will be selected so as to be rigid but relatively supple or elastic materials may be contemplated depending on the targeted applications. The plate shape allows the anchor (4) to ensure a good hold, at least in a direction substantially perpendicular to the plate since the width of the plate provides a surface opposed to the displacement of the anchor, and therefore of the implant, (perpendicularly to this surface) in the bone tissue in which it is planted. It will be noted that when the plate is curved, this maintaining is in fact ensured along at least one substantially radial direction to the radii of curvature of the plate.

In some embodiments, the bone anchoring device (4) has the shape of an elongated curved plate (40) along a longitudinal axis extending between its anterior end and its posterior end. Indeed, the anchor (4) advantageously has a plate shape which may provide a relatively thin thickness facilitating the penetration of the anchor (4) into the bone tissue. This small thickness of the plate (40) may pose a stability problem of the anchor (4) in the vertebrae, in so far that the plate may form a sort of blade capable of splitting the vertebrae in a direction oriented in the direction of the width of the plate (transversely to the longitudinal axis in some embodiments), notably during its impaction in the vertebra or later on, under the effect of significant stresses which will be applied to it during movements of the patient for example. Further, this small thickness may optionally reduce the rigidity of the plate. In some applications, the rigidity may be an important feature for efficient fixation, resulting in various more efficient embodiments than staples or others thin and/or relatively flexible or even fragile devices, which do not allow a good hold because of their flexibility and/or their fineness and/or their fragility. Thus, rigid anchors are preferred in many embodiments (curved anchors also being preferred, but for facilitating the approach to the vertebrae), instead of deformable anchors.

Figure 2B:
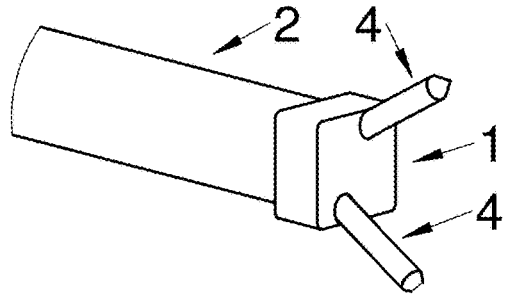
Figure 2C:
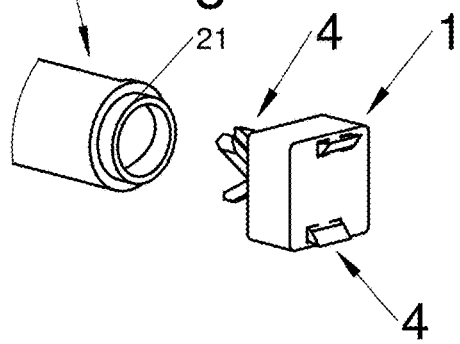
Figure 2D:
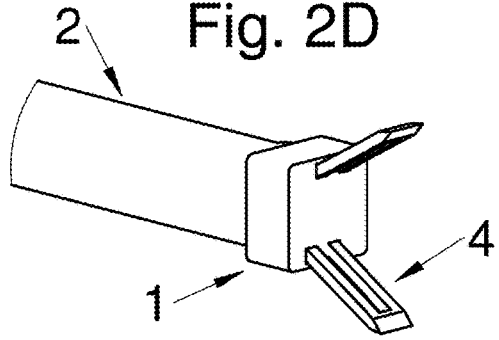
Figure 2E:
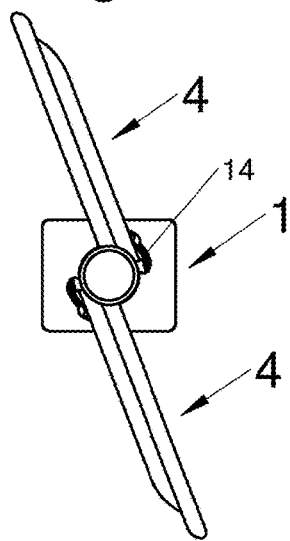
Figure 2F:
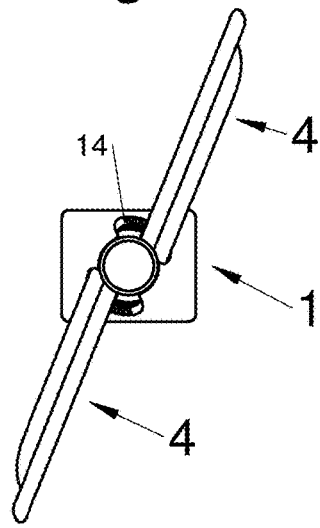
Figure 2G:
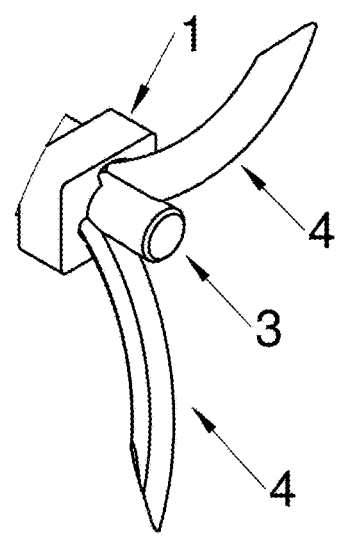
Figure 10A:
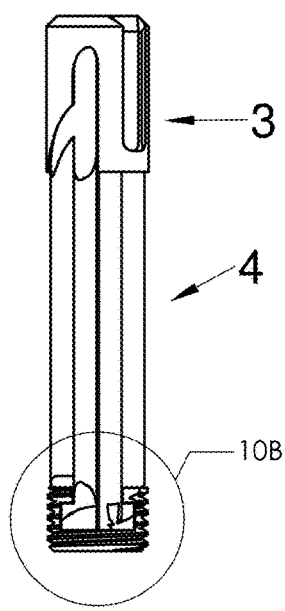
FIG. 10A illustrates a profile view of an embodiment of a bone anchoring system, comprising two anchors retained at their posterior end by a retaining element on the one hand, and at their anterior end by a guide on the other hand; the FIGS. 10C, 10D and 10E illustrate front perspective views of the system, respectively before, during and after the deployment of the anchors; the FIG. 10B illustrates a profile view of the posterior end of the anchors retained by the retaining element retaining the anchors together.
Figure 10B:
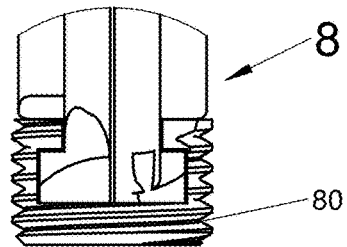
Figure 10C:
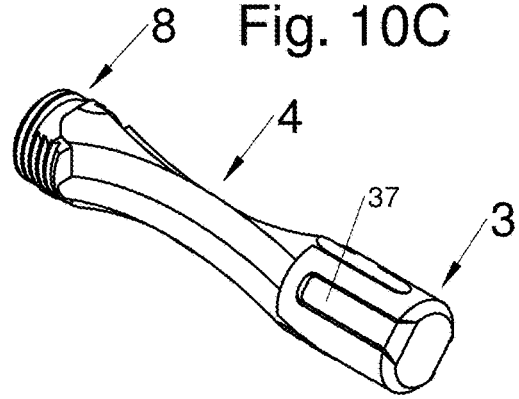
Figure 10D:
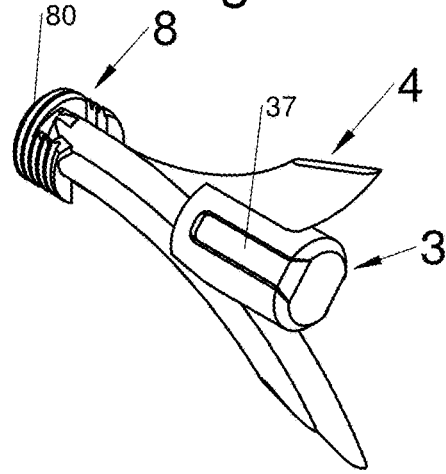
Figure 10E:
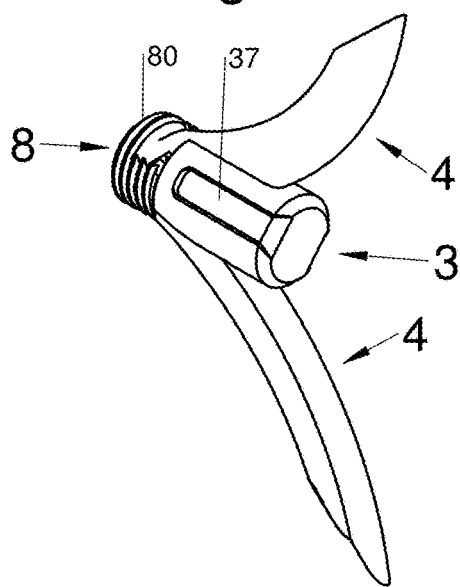

Thus, in some embodiments, the anchoring devices comprise an anchor with a rigid and elongated body, preferably curve as illustrated in the FIG. 2G, or a rectilinear anchor as illustrated in the FIG. 2D or a screw as illustrated in the FIG. 2B. However, the anchor (4) may also have the shape of a nail (with a round or polygonal section) or of a staple and the examples illustrated in the present application are not limiting.

In some embodiments, the anchor has the shape of a plate (40) provided with at least one rib (41) or a second longitudinal plate (41) or with at least one second plate extending along the longitudinal axis, not parallel to the first plate, and giving the anchoring device (4) an L-shaped, T-shaped, V-shaped, U-shaped or H-shaped section. Thus, the anchoring device (4) comprises one, two, three or several plates (40) with an L-shaped, T-shaped, V-shaped or H-shaped section. With these embodiments, the invention addresses the problems of stability and rigidity of the anchor (4) by the presence of at least one rib (41) or a second longitudinal plate (41) on at least one portion of at least one of the faces of the body of the anchor (4), which is preferably oriented in the direction of the length of the plate (40), substantially parallel to the longitudinal axis. The rib (41), which is a term optionally designating a second plate (41) not parallel to the first plate (40), gives the possibility of both rigidifying the anchor (4) and gives the possibility of limiting the risk or preventing that the anchor (4) be able to damage the bone tissues by "cutting" them in the direction of the width of the anchor (4). In order to prevent this displacement in the direction of the width of the anchor, designated hereafter as being "transverse" for more simplicity (it is transverse with respect to the length of the anchor), the rib (41) should preferably be of a sufficient height for allowing efficient blocking, while providing a sufficiently large surface for retaining the anchor transversely). Thus, the rib (41) forms a sort of fin preventing the anchor (4) from cutting the vertebra by a transverse displacement, which makes it fixation more reliable (improved) in the vertebra. Further, the increase in the rigidity of the anchor (4) generally tends to make its fixation also more reliable (improvement) in the vertebra: the plate will generally no longer be twisted or be folded, therefore having less risk of being ejected from the vertebra. Some embodiments of an anchor (4) comprising at least one rib therefore provide a good hold in 2 planes, instead of only one in the absence of such a rib (41).

In some embodiments of the anchor (4) (and optionally of the implant and/or of the instrumentation which may be associated with it), the width and/or the height of said rib (41) may vary along the longitudinal axis of the body. Thus, for example, as illustrated in some figures, the rib (41) begins to protrude in proximity to the anterior end of the anchor and its height gradually increases towards the posterior end. This height of the rib (41) may be constant over a determined portion, for example in proximity to the posterior end or vary over the whole of the length. For example and as illustrated in the FIG. 16, the height of the rib (41) is reduced for introducing a fin (11) into a complementary opening (412) in the plate (40). Further, in order to facilitate the penetration of the rib (41) into the bone tissue, the top of the rib (41); i.e. its upper portion (the one opposite to the plate), may be sharpened on at least one portion, for example in proximity to the anterior end. Also, the width of the rib (in the direction of the width of the plate) may also vary, for example by thickening towards the posterior end, either by this sharpening of the anterior end, or by pronounced thickening of the posterior end of the rib forming a stabilization structure of the anchor (1) in the implant (7, P), of the type of those described elsewhere in the present application.

It will be noted that various embodiments of the present invention provides various configurations of the anchor (4) as regards the direction of its curvature. Still referring to the insertion direction of the anchor, it is understood that some embodiments of the anchor are intended to penetrate the bone tissues from the periphery of the bone space as far as into the bone tissues, for example and in a non-limiting way in the lower vertebral plate of the upper vertebra or in the upper vertebral plate of the lower vertebra, notably in the case of intervertebral implants such as intersomatic cages or intervertebral disc prostheses. When the anchor is intended to be implanted in vertebral plates, for example through implants such as intersomatic cages or intervertebral disc prostheses, the curvature of the anchor is preferably configured so that, once the anchor planted into the vertebral body, the vertical axis of the spine is substantially tangent to a substantial part of the called anterior end of the anchor or at least that this portion of the anterior end forms an angle with a low value with the axis of the spine. Further in some embodiments, the anchoring device (4) is intended to be anchored in a bone tissue so as to fix the implant on/against this bone tissue. The anchoring device (4) according to various embodiments of the invention therefore includes at least one rigid and elongated body, preferably curved and with the shape of a plate or nail (with a rectangular, circular, square, polygonal or T-shaped, L-shaped, U-shaped or even H-shaped section), laid out for penetrating into a bone tissue through an implant for retaining this implant against this bone tissue.

In some embodiments, the anchoring device comprises at least one gripping means (49) capable of receiving a gripping tool with which the anchor may be grasped, either for handling the anchor before its implantation, or for withdrawing it from the bone tissue when ablation is desired. The gripping means (49) is for example and in a non-limiting way, either an opening, for example as illustrated in the FIG. 12A or 12D, or a notch, for example as illustrated in the FIG. 13A or 15A, or a protrusion (not shown).

Figure 28A:
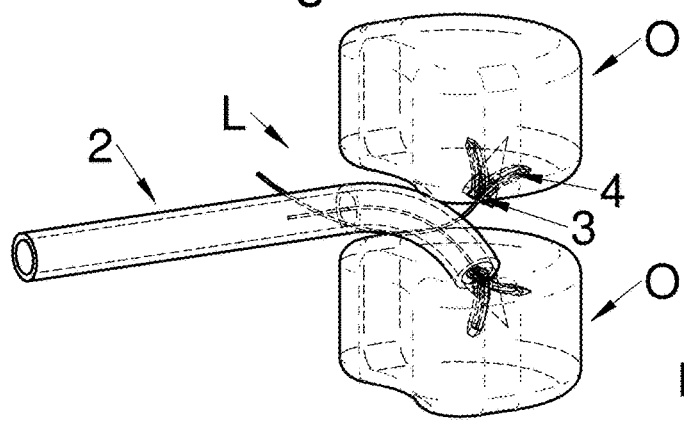
FIG. 28A illustrates a perspective view of a bone anchoring system according to an embodiment comprising a ligament associated with each bone anchoring, during impaction of the bone anchorings between two adjacent bone structures; the FIGS. 28B and 28C illustrate respectively rear perspective and profile views of the same bone anchorings once set into place, with the implant introduced between both adjacent bone structures in the FIG. 28C; the FIGS. 28D and 28E illustrate rear perspective views of this system, respectively during and after introduction of both implants between the two adjacent bone structures and locking of the implants by the ligaments associated with the bone anchorings.
Figure 28B:
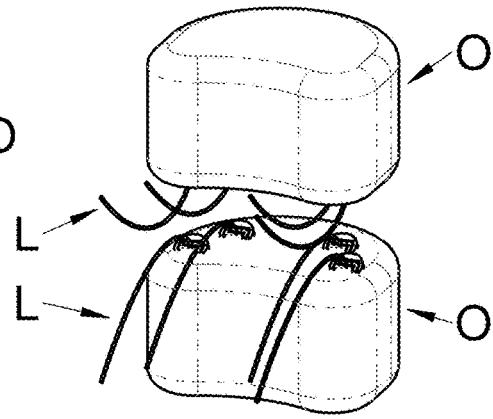
Figure 28C:
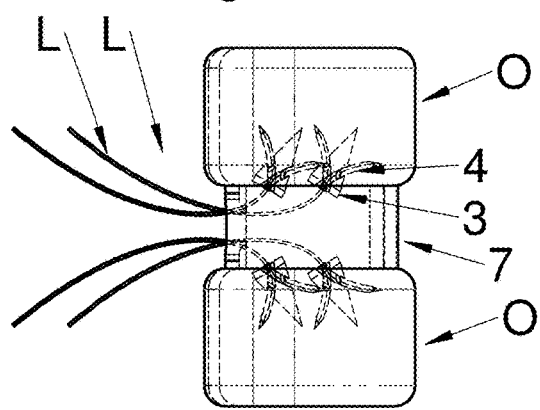
Figure 28D:
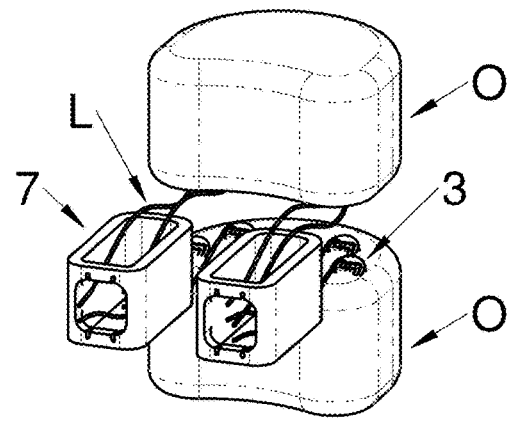
Figure 28E:
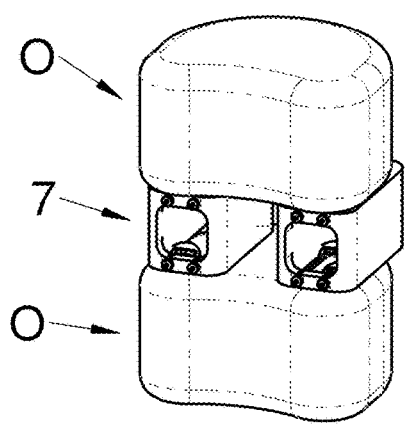

In some embodiments, the anchoring system comprises a ligament (L) allowing the implant (7, P) to be implanted after implantation of the anchoring device (4), for example as illustrated in FIGS. 28C and 28D. Thus, in some embodiments, the anchoring device (4) comprises at least one housing or a groove (4L) capable of receiving a binding means (L) giving the possibility of binding the anchoring device (4) to the implant (7, P), for example as illustrated in the figures of plate 26. In some embodiments, by additive manufacturing of anchoring devices allow to entangle the latter beforehand so as to produce anchoring devices at least partially entangled in each other, for example as illustrated in Figs. of the plate 25.

In some embodiments, the anchoring device comprises at least one cannula (400), preferably oriented in the length of the anchor as illustrated in the FIG. 3D, giving the possibility of injecting bone substitutes or grafts for growth for example. Preferably this cannula opens at each end of the anchor, in order to allow injection from the posterior end which remains outside the bone, in order to be able to inject the grafts or substitutes after bone anchoring. One or several cannulas (401) oriented perpendicularly to the surface of the anchor and crossing its thicknesses may also be contemplated.

Instrumentation

The figures of plates 1 to 31 show illustrative and non-limiting examples of various possible configurations of the bone anchoring instrumentation, i.e. combinations of instruments which may be used for implanting an anchoring device (4) in a bone tissue (O), an implant (7, P) and a bone anchoring system. The various instruments will now be described with reference to the illustrative and non-limiting figures. In some embodiments, the anchoring system comprises a support (2), a loader (5), a guide (3) and an impactor (6), for example as illustrated in the figures of plates 1 and 5. In this type of configuration, the anchoring device (4) and the guide (3) are temporarily accommodated in the loader (5) itself accommodated in the support (2), for example as illustrated in the FIGS. 1B, 1D and 5A, and then the anchoring device (4) and the guide (3) are pushed by the impactor (6) towards the bone tissue (O), as illustrated by the FIGS. 1B to 1E and 5B to 5D, and finally the anchoring device (4) is guided by the guide (3) and/or the fixation plate (1) for deployment of the anchors (4) of the device and for anchoring the latter in the bone tissue (O), for example as illustrated in the FIGS. 1E, 1F and 5B to 5D. Thus, these different configurations have the advantage of proposing non-exhaustive instruments (1, 2, 3, 4, 5, 6), giving the possibility of carrying out efficient and rapid anchoring of an anchoring device (4) in a bone tissue (O). Indeed, the instruments of the system assembled together by shape complementarity and/or coupling means, so as to facilitate the deployment of the anchors in a stable way. Further, it is possible to carry out an implantation of several anchoring devices successively. Indeed, for example as illustrated in the FIG. 5, several anchoring devices may be successively implanted in the bone tissue with the same anchoring instrumentation.

The Guide (3)

In some embodiments, the guide (3) of the anchoring system comprises means for cooperation or coupling with one or several instruments (1, 2, 4, 5) or with an implant (7, P) of the present invention.

In some embodiments, the guide (3) comprises at least one groove (37) intended to cooperate with the walls of the passage (72) in the implant (7) or in the plate (1), for example as illustrated in the FIG. 1B or 9B. The groove (37) is fixed, either complementarily or not, in the wall of the passage (72) of the implant, so as to consolidate the guide and anchoring device assembly in the implant.

Figure 25A:
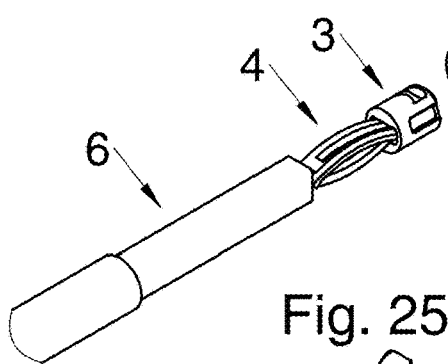
FIG. 25A illustrates a perspective view of a bone anchoring system according to an embodiment comprising two anchors, one fixation plate, one support, one guide and one impactor; the FIGS. 25B and 25C illustrate perspective views, respectively front and rear perspective views, of the system after deployment and withdrawal of the support and of the impactor; the FIGS. 25D and 25F illustrate views of the rear face of the guide without any fixation plate respectively with and without the anchors inside; and the FIGS. 25E and 25G illustrate profile views of this guide, respectively, during and after deployment of the anchors.
Figure 25C:
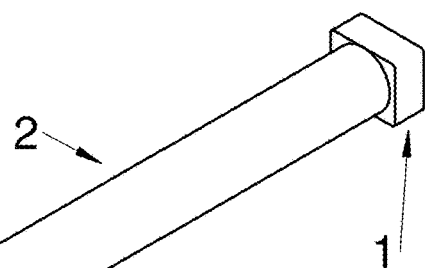
Figure 25B:
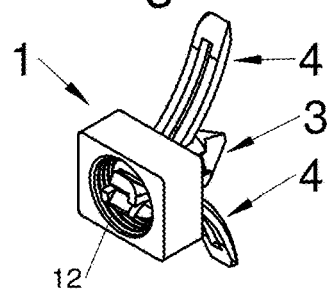
Figure 25D:
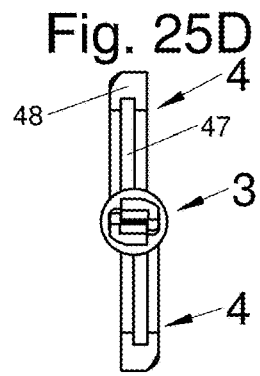
Figure 25E:
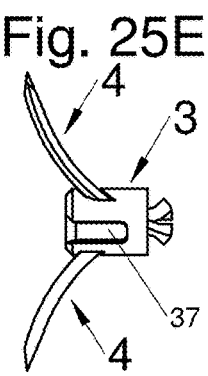
Figure 25F:
Figure 25G:
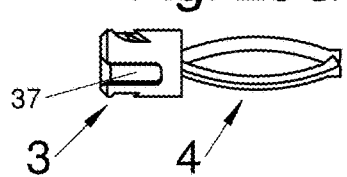
Figure 26A:
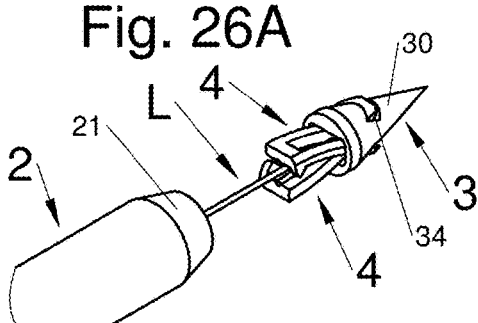
FIG. 26A illustrates a perspective view of a bone anchoring system according to an embodiment comprising two anchors, a support, a guide and a ligament; the FIGS. 26B and 26C illustrate perspective views of the anchoring system completed with an impactor, respectively before and after deployment of the anchors in a bone tissue; the FIGS. 26D and 26F illustrate respectively rear perspective and rear face views of the guide during the deployment of the anchors and before the locking of the ligament by the anchors and the FIG. 26E illustrates a rear perspective view of this same guide after deployment of the anchors and locking of the ligament.

In some embodiments, the anterior end (30) of the guide (3) comprises a chamfer or a bevelled profile facilitating the penetration of the element (3) in the bone tissue (O), for example as illustrated in the FIG. 25C or 26A. Indeed, the bevelled profile of the guide facilitates the penetration of the latter into the bone tissue, without exerting or very little additional force during the impaction, while guiding the deployment of the anchors of the anchoring device.

In some embodiments, the posterior end of the guide (3) is at least partially positioned in the opening (13) of the fixation plate (1), for example as illustrated in the FIG. 1C or 3A. This embodiment gives the possibility of cooperating and immobilizing the guide with the fixation plate, so as to obtain anchoring instrumentation in which the guide easily cooperates with the fixation plate.

The Support (2)

In some embodiments, the support (2) of the anchoring system comprises cooperation or coupling means with one or several instruments (1, 3, 4, 5, 6) or with an implant (7, P) of the present invention. In some embodiments, the support (2) of the system cooperates with a fixation plate (1) for facilitating the deployment of the anchors (4) towards the bone tissue (O). Indeed, the anterior end of the support (2) comprises, for example an external threading (21) intended to cooperate with a tapping (12) in the posterior end of the fixation plate (1), for example as illustrated in the FIG. 1A. This configuration is one of the embodiments giving the possibility of stabilizing the fixation of the support with the fixation plate, thereby facilitating the implantation of the anchoring device through the support and the plate in the bone tissue. The external threading (21) of the support (2) and the complementary tapping (12) of the fixation plate (1) may be replaced with a recess and with a complementary raised part or any equivalent giving the possibility of ensuring the stability of the anchoring instrumentation for implanting the anchoring device in the bone tissue.

For some embodiments, the support (2) cooperates with an implant (7, P) for facilitating the impaction of the anchors towards the bone tissue (O). Indeed, the anterior end of the support (2) comprises an external threading (27) intended to cooperate with a tapping in proximity to the passage (72) of the posterior end of the implant (7), for example as illustrated in the FIG. 7A. This configuration is one of the embodiments giving the possibility of stabilizing the fixation on the support with the implant, thereby facilitating the gripping and implantation of the implant by the support in the bone tissue. The external threading (27) of the support (2) and the complementary tapping of the implant may be replaced with a recess and with a complementary raised part or any equivalent giving the possibility of ensuring the stability of the gripping and of the implantation of the implant in the bone tissue.

In some embodiments, the support (2) of the system cooperates with an impactor (6) and/or a loader (5) for facilitating the impaction and the deployment of the anchors towards the bone tissue (O). Indeed, the posterior end of the support (2) is open for allowing insertion of the impactor (6) and/or the loader (5) into the support (2) in order to push and guide the anchoring device (4) towards the bone tissue (O). The support (2) is a rectilinear or partially curved conduit, allowing introduction of the implantation elements and/or of the elements participating in the implantation of the latter. Consequently, the support comprises an opening allowing introduction of the anchoring devices as an implantation element, as well as the impactor and the loader as elements participating in the implantation of the anchoring devices.

In some embodiments, the body (20) of the support is curved for guiding the anchoring device(s) along a curvilinear path for approaching the bone tissue (O), according to the FIGS. 4A and 28A. Various embodiments of the present invention also provide a curved support, at least partially curved, in order to facilitate the introduction of the instrumentation into an area with reduced access.

The Loader (5)

In some embodiments, the system includes at least one loader (5). The loader (5) is a adaptor laid out for loading the anchoring devices in the support (2). In other words, the loader (5) is capable of receiving and temporarily maintaining the anchoring devices on the one hand and capable of being accommodated in the internal conduit of the support (2) on the other hand. In some embodiments, the fixation plate (1) is able to cooperate with the anchoring device (4) by cooperation means (14), with the support (2) by cooperation means (12, 21), with the guide (3) by cooperation means (13), with the loader (5) and/or with the impactor (6) by cooperation means (151).

As already mentioned, and for example as illustrated in the FIGS. 1E, 3C, 4B and 5C, the support (2) and the loader (5) have a hollow and elongated body of a rectilinear shape, for example as illustrated in the FIG. 3B, or a curved shape, for example as illustrated in the FIG. 4B. Both of these different forms of the instrumentation allow the surgeon to either use a rectilinear shape or either a shape, at least partially curved of the instrumentation in order to adapt the latter with respect to the environment of the bone tissue. Indeed, a curved shape of the instrumentation may be advantageous for an implantation in a space which is difficult to access. For example, a curved instrumentation is used for implanting an anchoring device between two adjacent vertebrae along the surgical plane. In some embodiments, the anchors of an anchoring device may be of different length and/or of different radius of curvature. For example and in a non-limiting way, one of the anchors of the FIG. 4D is shorter as compared with the other anchor of the device. This type of dimensioning of the anchors may be used both in a curved instrument and in a rectilinear instrument. Thus, for example and in a non-limiting way, a shorter anchor implies a larger radius of curvature as compared with the associated anchor, so that each curvature of the anchors is in contact with the inner wall of the support. This difference in the dimensioning of the anchors provides more freedom to the surgeon for achieving surgery. For example, a device comprising one of these longer anchors gives the possibility of achieving oblique anchoring with or without bone implants in the space of the bone tissue.

In some embodiments, the loader (5) of the anchoring system comprises means for cooperation or coupling with one or several instruments (1, 2, 3, 4, 6) of various embodiments of the present invention. In some embodiments, the loader (5) cooperates with a guide (3) for facilitating the deployment of the anchors towards the bone tissue. Indeed, the anterior end of the loader (5) comprises a means (53) for cooperating with the posterior end of the guide (3), for example as illustrated in the FIG. 1D. This embodiment gives the possibility of immobilizing the guide with the loader during the implantation of the anchoring device in the bone tissue. This cooperation means has a shape which allows the loader to grip the posterior end of the guide so that the latter may follow the trajectory defined by the loader.

In some embodiments, the loader (5) cooperates with the anchors (4) of the anchoring device (4) for maintaining and guiding the deployment of the anchors. Indeed, the loader (5) comprises at least one opening (54) in a wall of the loader so as to allow at least partially the introduction of at least one anchoring device (4) inside the loader, for example as illustrated in the FIGS. 3B and 4B.

In some embodiments, the body (50) of the loader (5) is curved as illustrated in the FIG. 4B. Various embodiments of the present invention also provides a curved loader, at least partially curved, when the support is also curved or partially curved, in order to introduce the loader into the support.

The Fixation Plate (1)

In some embodiments, the fixation plate (1) of the anchoring system comprises means for cooperation or coupling with one or several instruments (2, 3, 4, 5, 6) of various embodiments of the present invention. In some embodiments, the fixation plate (1), intended to be placed bearing against the bone tissue (O) or an implant (7, P), comprising a body (11) crossed by a guide opening (14) capable of guiding at least one anchoring device (4) and of receiving the first end of the support (2). In some embodiments, the fixation plate (1) comprising, in addition to the guide opening (14) adapted for at least partially guiding the anchoring device (4), at least one opening (13) adapted for at least partially receiving the guide (3).

In some embodiments, the fixation plate (1) includes at least one abutment for maintaining the guide (3) in the plate (1). In some embodiments, the fixation plate comprises an abutment (151) giving the possibility of limiting the movement of the loader (5) or of the impactor (6) beyond this abutment (151), which gives the possibility of preventing a too deep and undesired implantation in the bone tissue. Thus, the fixation plate comprises cooperation means (12) able to cooperate with the support (2), cooperation means (137) able to cooperate with the guide (3), cooperation means (14) able to cooperate with the anchoring device (4), cooperation means (151) able to cooperate with the loader (5) and/or with the impactor (6). In some embodiments, for example, the internal diameter of the opening (13) of the fixation plate (1) is smaller on the anterior side than on the posterior side, which forms an abutment for a shoulder of the guide (3), the diameter of which is greater on the posterior side than on the anterior side.

In some embodiments, the fixation plate (1) comprises an abutment (151) giving the possibility of limiting the movement of the loader (5) and of stopping it at the entry of the guide opening (14) of the anchoring device (4). Alternatively or additionally, the anterior end of the loader (5) comprises a cooperation means (51) adapted so as to be in abutment in the fixation plate (1). In the case of absence of the loader, this will be an abutment for the impactor (6) which may be provided, notably if the latter is not stopped in its travel by the actual support (2). Indeed, as the plate is mounted at the end of the support (2), the latter remains immobile with respect to the plate and only the elements passing into the inside preferably have to be limited in their travel for avoiding damaging the various instruments.

Figure 14A:
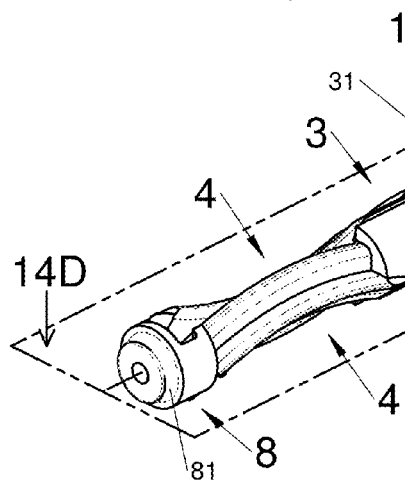
FIGS. 14A, 14B and 14C illustrate rear perspective views of an embodiment of a bone anchoring system, comprising an fixation plate and two retained anchors, on the one hand at their anterior end by a guide and on the other hand, at their posterior end by a retaining element respectively before, during and after deployment of the anchors; and the FIGS. 14D and 14E illustrate sectional views respectively along the plane 14D-14D of the FIG. 14A and along the plane 14E-14E of the FIG. 14C, of this system before and after deployment of the anchors.
Figure 14B:
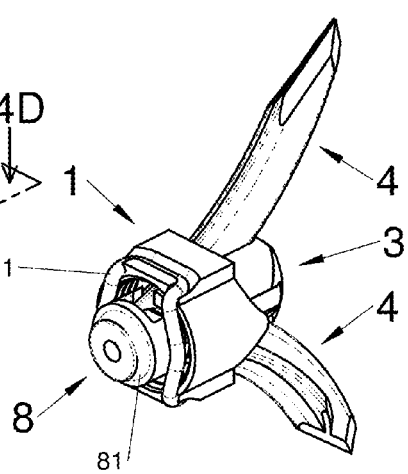
Figure 14C:
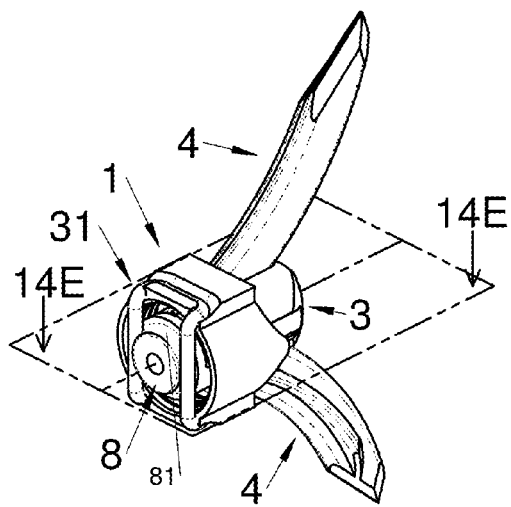
Figure 14D:
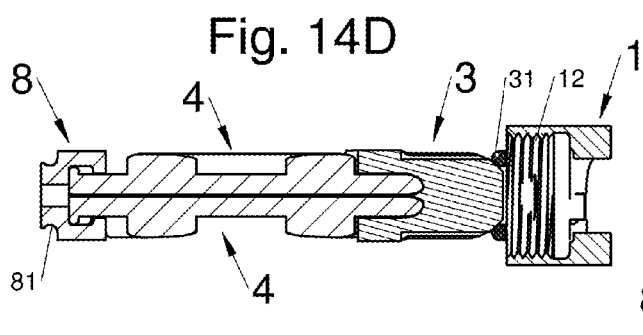
Figure 14E:
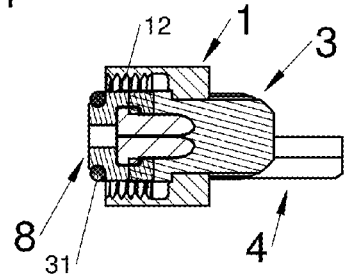

In some embodiments, for example as illustrated in the FIGS. 14A to 14C, the fixation plate comprises a locking means (31) giving the possibility of locking the fixation plate (1) on a retaining element (8), thereby immobilizing the anchoring device (4) deployed and anchored in the bone tissue. This locking means (31) may for example be a protrusion (31) able to be accommodated in a recess (81) of the retaining element (8).

The Impactor (6)

Figure 26B:
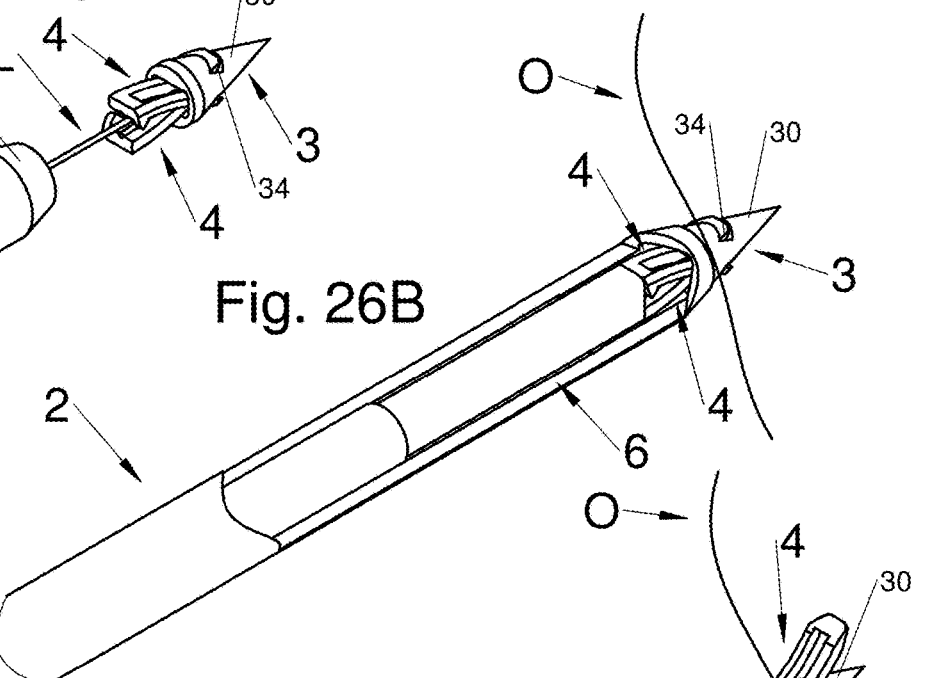
Figure 26C:
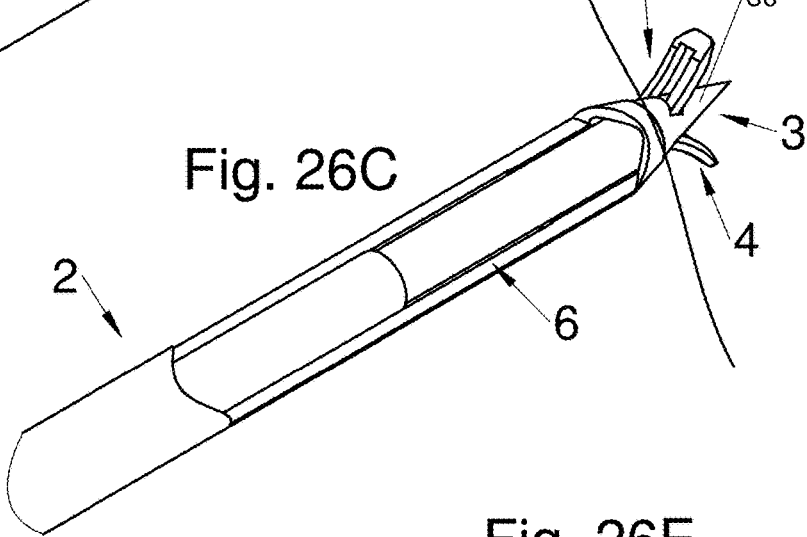
Figure 26D:
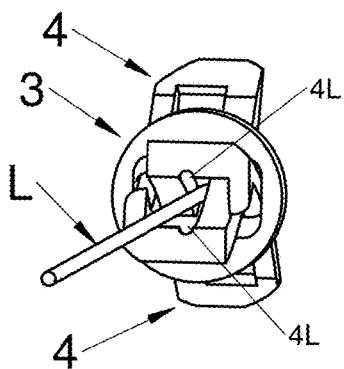
Figure 26E:
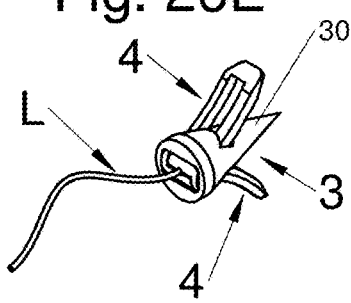
Figure 26F:
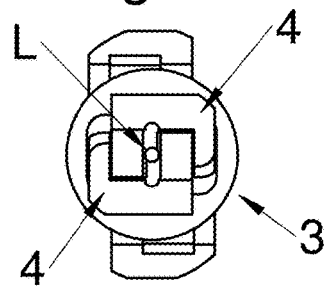

In some embodiments, the system comprises at least one impactor (6). In this type of configuration, the anchoring device (4) is accommodated in the support (2), for example as illustrated in the FIGS. 6A, 8A and 26B and the anchoring device (4) is then pushed by the impactor (6) towards the bone tissue (O), for example as illustrated in the FIGS. 7E, 8C and 26B, and finally the anchoring devices (4) are deployed for anchoring the latter in the bone tissue (O), for example as illustrated in the FIGS. 6C, 7E, 8C and 26C. The impactor (6) generally comprises a handle for sliding the body of the impactor relatively to a guide (61) and pushing the anchoring device (4) into the bone tissue, most often by repeated strikes in the insertion axis. This embodiment has the advantage of reinforcing the impaction of the anchoring devices, through the support to the bone tissue, via an impactor for reliable, stable and non-invasive anchoring. In some embodiments, the impactor (6) of the anchoring system comprises means for cooperation or coupling with one or several instruments (1, 2, 3, 4, 5) of various embodiments of the present invention.

In some embodiments, the pusher of the impactor (6) is adapted for pushing the head (61) of the impactor (6) in an opening (561) of the loader (5) so as to implant the anchoring device (4) contained in the loader (5) in the bone tissue (O). As particularly illustrated in the FIGS. 1D, 1E, 3B and 3C for example, the loader (5), comprising the anchoring device (4), is immobile in the support (2). The opening (561) of the loader (5) gives the possibility of introducing the head (61) of the impactor into the loader (5) so that it may cooperate with the anchoring device (4) and by means of the pusher of the impactor (6), the head (61) slides in the loader (5) causing displacement, along a defined trajectory, of the anchoring device (4) towards the bone tissue (O).

In some embodiments, the head (61) is of the same dimension as the loader (5) and the pusher of the impactor (6) comprises at least one abutment (65) allowing limitation of the movement of the head (61) beyond the loader (5). The movement of the head of the impactor is limited so that the anchoring device (4) may be anchored according to a defined depth in the bone tissue. Indeed, without this abutment (65), the head (61) will cause anchoring of the anchoring device (4) beyond the depth desired by the surgeon. Too deep anchoring of the anchoring device would make its withdrawal from the bone tissue more complicated, for example.

In some embodiments, the head (61) of the impactor (6) comprises on the one hand at least one pushing surface (640) able to cooperate with the posterior end of the anchoring device (4) and maintaining the latter against the impactor by the mutual cooperation between the cooperation abutment (64) of the impactor (6) and the cooperation abutment (46) of the anchoring device (4). As particularly illustrated and by no means in a limiting way in the FIG. 6D, the impactor (6) comprises cooperation means (640, 64, 460, 46) with the anchoring device (4) so that the impactor may direct the anchoring device (4) towards the bone tissue (O) without displacement of the anchoring device (4) facing the impactor (6) and obtained optimum implantation. Indeed, the anchor (4) comprises at least on a posterior part, a cooperation means (460), for example, a cut out (460), or another cooperation means (46), for example an opening (46). The impactor (6) comprises an additional cooperation means (64), for example a protrusion (64), able to cooperate with the cooperation means (46, 460) of the anchors either in the folded-back position or in the deployed position. As illustrated in the FIG. 6B, the anchor is in a folded-back position, in this case, the protrusion (64) of the impactor (6) is accommodated in the opening (46) of the anchor. On the other hand, when the anchor is in a deployed position, the protrusion (64) of the impactor (6) is found facing the cut out (460) of the anchor, for example as illustrated in the FIG. 6C, which gives the possibility of withdrawing the impactor (6) without pulling on the anchors which therefore remain anchored in the bone tissue. In these illustrative examples, mutual locking means (42, 44) of the anchors as described in the present application, may also be positioned in said posterior portion of the anchor in order to participate in the locking of the anchors while being accommodated in the opening (46), once the anchors (4) are in a deployed position.

In some embodiments, the bone anchoring instrumentation comprises at least one impactor (6) generally comprising a head (61), with adapted shapes and dimensions for sliding inside the support (2) and/or the loader (5), and pushing the anchoring device (4) towards the bone tissue (O). In some embodiments, the impactor also comprises at least one handle giving the possibility of pushing the head (61) for example retaining an anchoring device (4) and/or a retaining element (8) and/or an implant (7) in order to insert them, through a support (2), into a bone tissue. This handle may also consist in a block or plate on which the surgeon may tap, for example by means of a tool of a known type, for introducing the instruments mentioned above into the bone tissue. In some embodiments, the impactor comprises an abutment (65), positioned on one end of the handle for example, giving the possibility of limiting the travel of the impactor in the support and avoiding too deep anchoring of the anchors in the bone tissue, under some conditions, a withdrawal of the anchors may be required for replacing an anchor or after a complete bone fusion.

In some embodiments, on the one hand, the impactor (6) comprises at least one surface (640) for pushing the anchoring device (4) and, on the other hand, the anchoring device (4) and the impactor (6) comprise at least one mutual cooperation abutment (46, 64, respectively) for maintaining the anchoring device (4) in position with respect to the impactor (6). In this embodiment, the pushing surface (640) may be a cavity (640), on the anterior end of the implant, with adapted shape and dimensions for at least partially receiving the anchoring device (4), for example as illustrated in the figures of plate 6. This anterior end of the impactor may give the possibility of guiding this anchoring device (4) through the support (2) for implanting the anchoring device (4) in a bone tissue. For example, the anterior end of the impactor may comprise a complementary shape of the posterior end of the anchoring device. Further, this type of configuration facilitates deployment of the anchors towards the bone tissue.

In some embodiments, the impactor (6) comprises at least one abutment (65) limiting the penetration of the head (61) of the impactor (6) inside the support (2) and/or the loader (5), for example as illustrated in the figures of plate 1. In other embodiments, the abutment (65) is of greater dimensions than that of the head (61) in order to limit travel of the latter in the support (2). In some embodiments, such as for example illustrated in the FIGS. 1E, 4B, 5C and 8A, the head (61) of the impactor (6) may be slidably mounted inside the support (2) and/or the loader (5).

The Implant (7, P)

In some embodiments, the implant (7, P) of the anchoring system comprises means for cooperation or coupling with one or several instruments (1, 2, 3, 4,) of various embodiments of the present invention.

In some embodiments, for example as illustrated in the FIGS. 31A to 31E, in a first phase, the implant (7) is positioned between two bone tissues (O) by means of the support (2), and the anchoring device (4) is then anchored in the bone tissue (O) by the same support (2) or another one, for example along the side walls of the implant (7). Thus, in these types of configuration, the support (2) is also able to cooperate with the implant (7) by complementary cooperation means (not shown in the figures), such as for example and in a non-limiting way a threading, a recess or a raised part.

In some embodiments, the support (2) of the bone anchoring instrumentation comprises cooperation means (27) with at least one implant (7) so as to anchor the implant (7) in the bone tissue (O). These mutual cooperation means between the instrumentation and the implant give the possibility of gripping the implant with the instrumentation in order to implant the latter in the bone tissues. An intervertebral implant, for example as illustrated in the FIGS. 7, 8, 28, 30 and 31, may be implanted by the instrumentation of the present application between two adjacent bone tissues, for example adjacent vertebrae. In some embodiments, the anchoring device may be used with intersomatic cages or on prostheses, this anchoring device cooperates with a slot or a groove or a housing located on the implant which is intended to be fixed on the bone tissue.

Figure 29A:
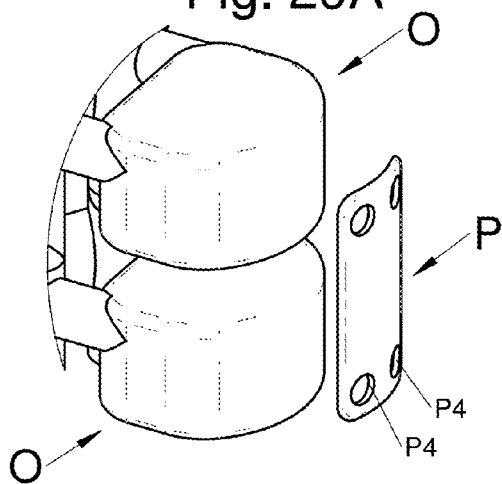
FIGS. 29A and 29B illustrate front perspective views of two adjacent vertebrae and of an embodiment of a bone anchoring system comprising an implant of the plate type respectively before and after affixing this plate against both adjacent vertebrae; the FIGS. 29C and 29D illustrate respectively front perspective and profile views of this system completed with a support for fixing the plate with a bone anchoring comprising two anchors, and a guide; and the FIG. 29E illustrates a profile view, with transparence of the vertebrae, of this system when the anchors are deployed through the plate into the vertebrae.
Figure 29B:
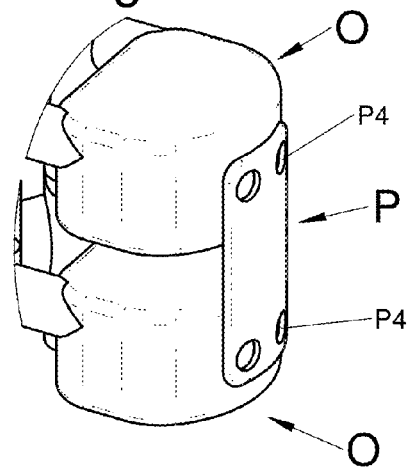
Figure 29C:
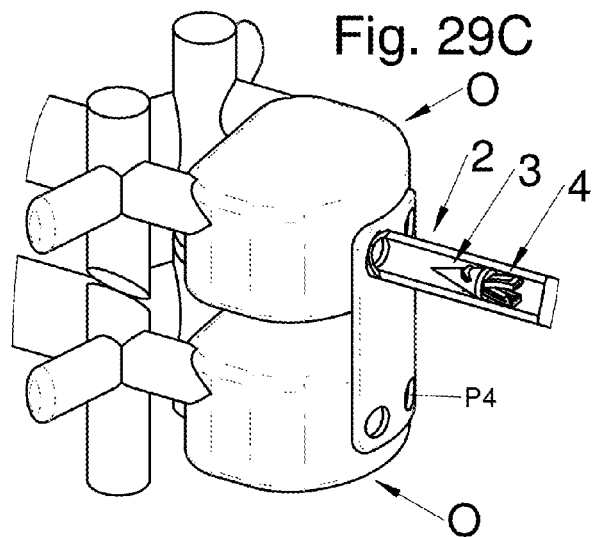
Figure 29D:
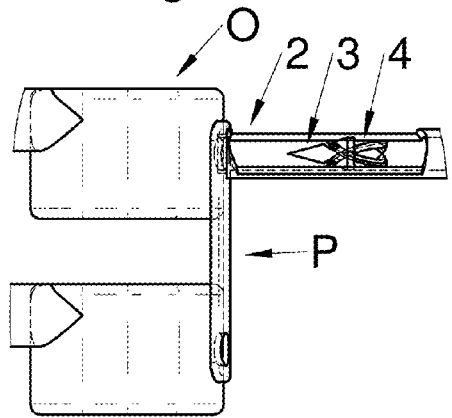
Figure 29E:
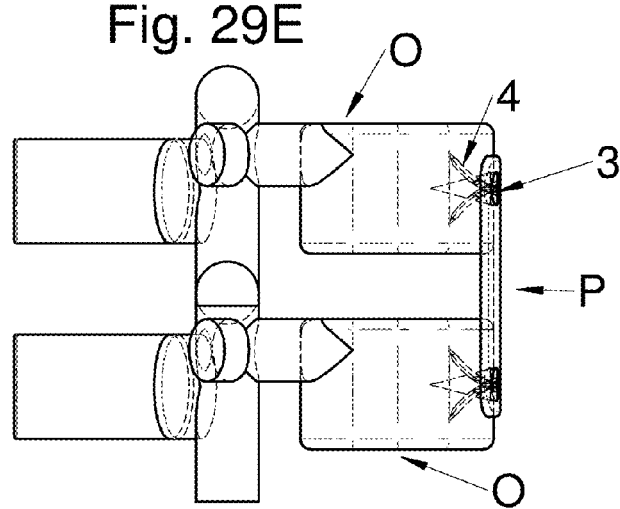

In some embodiments, a bone fixation plate (P) is able to be positioned against two adjacent bone tissues, for example as illustrated in the FIG. 29B, the anchoring device (4), which is accommodated in the support (2), is pushed through an opening (P4) of the plate (P) so as to attach the plate (P) against the bone tissues (O) and anchor the anchoring device (4) in the bone tissues (O) as illustrated in FIG. 29E. Thus, in some embodiments, the implant comprises at least one bone fixation plate (P) intended to be flattened and fixed against the bone tissues (O) by at least one anchoring device (4) of the instrumentation of the present application. In some embodiments, the fixation plate (P) has openings (P4) through which the anchoring devices are implanted in the bone tissue so as to fix and stabilize the fixation against the bone tissues. Further, the anchors are deployed in the fixation plate (P) and the anchors are thus locked to each other by their deployment in the opening (P4), thus it is possible not to provide any retention mechanism or means (42, 44) of the anchors or screws for preventing the anchors from moving backwards relatively to each other.

In some embodiments, the implant (7) comprises at least one opening able to receive a bone graft (G), for example as illustrated in the FIG. 30. Indeed, it is sometimes necessary to implant a bone graft beforehand in the implant, in order to facilitate and accelerate bone fusion. Once the graft is implanted, the anchoring device may be implanted for anchoring the assembly in the bone tissue. Thus, the instrumentation of the present application also provides means, such as an opening, for further facilitating the implantation of bone graft. In some embodiments, these bone implants comprising a cavity are generally used for confining bone tissue (graft) which will grow inside the space of the bone tissue and will allow fusion (arthrodesis) of the bone tissues between which the implant is implanted. The use of a substitute instead of a bone graft is also known.

In some embodiments, the implant (7) comprises at least one peripheral wall (70), for which at least one called posterior part comprises at least one passage (72) with adapted dimensions for receiving at least one anchoring device (4) so as to allow the passage of this rigid anchoring device (4) without any deformation in the bone tissue (O). In some embodiments, the passage (72) of the implant comprises a groove or a housing intended to receive at least one anchor of the anchoring device allowing a good fixation between the implant and the anchoring device.

In some embodiments, the peripheral wall (70) of the implant (7) is configured, at least at the posterior part, for cooperating with at least one end for gripping one of the instruments of said bone anchoring instrumentation. In some embodiments, the instrument, the gripping end of which cooperates with the peripheral wall (70) of implantation of the implant (7), is the support (2) and/or the fixation plate (1) and/or the guide (3). In some embodiments, this peripheral wall (70) cooperates with the gripping end of the instrumentation, through one of its rear faces, for example as illustrated in the FIG. 30, and/or through one of its side faces, for example as illustrated in the FIG. 31. In some embodiments, this peripheral wall (70) of the implant (7) comprises cooperation means (72) at its posterior part for cooperating with one of the instruments, preferably with the support (2), of the present instrumentation. In some embodiments, these cooperation means are defined as means for hooking up the instrumentation in order to allow the gripping or the retaining of the implant by the instrumentation. This hooking-up means may comprise at least one housing (72) intended to receive at least one gripping means (27) of the instrumentation, for example as illustrated in the FIG. 7.

These hooking-up means may be at least formed partially with different surface of the implant, the gripping means of the instrumentation then having a shape complementary to these surfaces so as to allow the gripping of the implant. It is also possible that the hooking-up means may include a protruding portion outside the implant and intended to be inserted in a housing of a gripping means of the instrumentation. Thus, these hooking-up means may, according to the embodiments, be associated with a particular shape of the implant in order to allow good cooperation with the instrumentation or even comprise one of these particular shapes cooperating with complementary forms of the instrumentation. For example, the instrumentation may comprise a contact surface fitting the shape of the implant in proximity to the passage (72). Also, as mentioned earlier, the implant may include a cavity in its centre or not, in so far that it is frequent to implant several bone implants in a same space of the bone tissue (in as much as the dimensions allow this). In some embodiments, as illustrated in a non-limiting way in the FIGS. 1 and 7D, the peripheral wall (70, 72) of the implant (7) cooperates with a cooperation means (37) of the guide (3) of the anchoring instrumentation. This embodiment gives the possibility of stabilizing the guide in the implant so as to lock the anchoring of the anchoring device and the fixation of the implant in the bone tissues. Indeed, these cooperation means (70, 72, 37) allow cooperation between the guide and the implant so that during and after implantation of the anchoring device, the anchoring implant and device assembly is stable and immobile so that the deployment of the anchors of the anchoring device or their anchorings in the bone tissue is efficient.

In some embodiments, the peripheral wall comprises, at an anterior portion, generally opposite to the one including the passage (72), at least one chamfer or a bevelled portion, so as to facilitate the insertion of the implant (7) between two bone tissues (O). This chamfer is arranged on at least one peripheral portion of at least one of its upper and lower surfaces, as particularly visible in the FIGS. 28, 30 and 31. This chamfer or bevelled profile may substantially be located in the implantation axis of the implant and gives the possibility of facilitating the implantation of the implant while giving it a substantially lower height on its leading edge (the one intended to be inserted first) than on the remainder of the implant.

In some embodiments, the elements or instruments (1, 2, 3, 4, 5, 6, 8, 10, 11) making up the anchoring system are made in a solid and biocompatible material, for example Titanium. In some embodiments, at least one portion of these elements or instruments, generally the fixation plate (1) and/or the guide (3) may be made in a more flexible material such as for example PEEK (polyetheretherketone), notably for preventing a metal/metal contact between the elements or instruments. Further, the advantage of the flexibility of this type of material is sometimes mentioned for better retaining the anchors which are then provided for slightly deforming the material and enters by force into its passage or housing. In some embodiments, at least one of these elements or instruments, preferably the anchoring device (4), may be made in a solid but flexible material such as for example Nitinol, in order to provide some flexibility to the anchors while guaranteeing good resistance.

Some embodiments also have the purpose of overcoming various drawbacks of the prior art by proposing an implant, in particular intended to be implanted in at least one bone tissue by bone anchoring implantation according to various embodiments of the invention allowing stable, easy, rapid implantation and with reduced invasivity. Thus, in some embodiments, the anchoring system for the implantation of at least one anchoring device in at least one bone tissue, further comprises an implant comprising at least one means (27) for cooperation with the support (2) and at least one coupling means with at least one anchoring device (4), such as for example a passage or a housing for receiving at least one anchor (4), either associated or not with a plate (1) and/or a guide (3). The bone anchoring instrumentation, generally at least the support (2), may also be configured for impacting the anchoring device in the bone tissue directly through the implant. This solution is described in the following patent applications of the applicant: FR 2 916 956, FR 2 954 692 and WO 2008/149223 but the present application provides many improvements as described above, notably as regards rapidity of the surgery, or as regards the locking of the anchors, or as regards the anchoring obtained by a combination of one or several anchors with each other, alone or as a combination with a guide and/or a plate. In particular, the anchoring system therefore provides an instrument, such as the support (2), achieving the gripping and the implantation of the implant in the bone tissue, for example as illustrated in the FIGS. 7 and 31, but at the same time allowing bone anchoring according to various advantageous embodiments detailed above. The anchoring system also provides instruments, from among those described in the present application (the support and the guide and/or the impactor and/or the loader and/or the retaining element and/or the locking plug), for the implantation of the anchoring device in the bone tissue. In some embodiments, for example as illustrated in the FIG. 28, the anchoring device may be implanted before or after implantation of the implant. This method gives the possibility, in some scenario, of improving the accuracy in the positioning of the anchoring in the bone tissue, without the implant interfering with the visibility and/or this accuracy, and of then more easily inserting the implant which is then guided as far as its final position by the anchors already deployed in the bone tissue(s), for example by bringing the implant in contact with or in proximity to these anchors. In some embodiments, for example as illustrated in the FIGS. 29 and 30, the anchoring device (4) may be implanted through the implant (7, P). In some embodiments, for example as illustrated in the FIG. 31, the anchoring device may be implanted in the bone tissue and go along at least one of the side walls of the implant. In this embodiment, the anchoring device and the implant are anchored, without any fixed connection between them, in the bone tissue, which gives the possibility of facilitating ablation. Indeed, the anchoring devices or the bone implants may be withdrawn independently of each other when this is required. Further, this configuration allows fixation of an anchoring device with an implant without passing of the anchoring device in the implant. Indeed, the surgeon has the possibility of implanting the anchoring device on the sides of the implant if an implantation of the anchoring device through the implant is not sufficient for stabilizing the latter with respect to the bone. Further, this configuration gives the possibility of achieving the fixation of several implants with an anchoring device connecting at least two implants. For example, two fixation plates (P) may be attached on the bone tissues by at least one anchoring device connecting both fixation plates together. Consequently, the surgeon, with the bone anchoring instrumentation of the present application, may modulate the implantation of one or several bone implants and of one or several anchoring devices in the bone tissues.

In some embodiments, a bone anchoring instrumentation comprises at least one support (2) able to receive at least one anchoring device (4) and of guiding it towards the bone tissue (O). This instrumentation allows stable, reliable and non-invasive anchoring of the anchoring device in the bone tissue. Further, this instrumentation may be associated with at least one implant (7, P), for example in order to fix the latter in or against a bone. The implant may naturally exert the function for which it is provided and the examples given in the present application are of course non-limiting since it is sufficient that the anchoring proposed here is compatible with the function of the implant. In some of these embodiments, the bone anchoring instrumentation further comprises at least one additional instrument (1, 3, 5, 6) as described in the present application.

Some embodiments have also the purpose of overcoming some drawbacks of the prior art by proposing a bone anchoring instrumentation, in particular intended for an implantation of at least one anchoring device in at least one bone tissue, allowing a stable, easy, rapid implantation and with reduced invasivity. In some embodiments, a bone anchoring instrumentation comprises at least one support (2) able to receive at least one anchoring device (4) and to guide it towards the bone tissue (O). This instrumentation allows stable, reliable and non-invasive anchoring of the anchoring device in the bone tissue. Further, this instrumentation may be associated with at least one implant (7, P), for example in order to fix the latter in or against a bone. The implant may naturally exert the function for which it is provided and the examples given in the present application are of course not limiting since it is sufficient that the anchoring proposed here is compatible with the function of the implant. In some of these embodiments, the bone anchoring instrumentation further comprises at least one additional instrument (1, 3, 5, 6) as described in the present application.

From the present application it is understood that the proposed system and instrumentation provide improvements of various structures and methods which may be used in various applications of orthopedic surgery for reducing the invasivity and the duration of the operations required for providing a reliable bone anchoring.

The present application describes various technical features and advantages with reference to the figures and/or to various embodiments. One skilled in the art will understand that the technical features of a given embodiment may in fact be combined with features of another embodiment unless explicitly mentioned otherwise, or that it is not obvious that these features are incompatible or that the combination does not provide a solution to at least one of the technical problems mentioned in the present application. Further, the technical features described in a given embodiment may be isolated from the other features of this embodiment unless explicitly mentioned otherwise.

It should be obvious for skilled practitioners that the present invention allows embodiments under many other specific forms without departing from the field of application of the invention as claimed. Therefore, the present embodiments have to be considered as an illustration, but may be modified in the field defined by the scope of the appended claims, and the invention should not be limited to the details given above.

The invention claimed is:

1. An anchoring system, for concurrent implantation of a pair of anchoring devices in a bone tissue, the system comprising:

a pair of anchoring devices, each anchoring device comprising a curved body extending between an anterior end configured to penetrate with limited deformation in the bone tissue and a posterior end configured to remain turned outward of the bone tissue and coupled to an implant, the pair of anchoring devices defining a longitudinal axis prior to implantation;

an guide retaining the pair of anchoring devices along the anterior ends of each anchoring device at least partially within a pair of guiding surfaces disposed within the guide, each guide surface of the pair of guiding surfaces curved in opposing directions and configured to guide one of the pair of anchoring devices;

a tubular support including an interior bore dimensioned to receive the guide retaining the pair of anchoring devices for insertion into an implant; and at least one impactor comprising a head, with shapes and dimensions adapted for sliding inside the tubular support and pushing the pair of anchoring devices towards the bone tissue.

2. The anchoring system according to claim 1, further comprising at least one implant, the at least one implant including a passage to receive the guide and the pair of anchoring devices.

3. The anchoring system according to claim 2, in which said implant comprises at least one bone fixation plate configured to be fixed on said bone tissue by at least one anchoring device of said system.

4. The anchoring system according to claim 2, in which the implant comprises at least one opening able to receive a bone graft.

5. The anchoring system according to claim 4, in which the implant comprises at least one peripheral wall, at least one part, called posterior, includes at least one passage including dimensions for receiving at least one anchoring device configured to allow the passing of at least a portion of the anchoring device into the bone tissue.

6. The anchoring system according to claim 5, in which the peripheral wall is configured, at least at the posterior part, to couple with at least one gripping end of an instrument.

7. The anchoring system according to claim 1, in which each anchoring device of the pair of anchoring devices has a shape of plate curved and elongated along a longitudinal axis extending between its anterior end and its posterior end.

8. The anchoring system according to claim 7, in which a plate of each anchoring device is provided with at least one longitudinal rib or with at least one second plate extending along the longitudinal axis, not parallel to a first plate, and giving to each anchoring device an L-shaped, T-shaped, V-shaped, U-shaped or H-shaped section.

9. The anchoring system according to claim 8, in which the impactor comprises at least one surface for pushing the pair of anchoring devices and, the anchoring device and the impactor comprise at least one mutual cooperation abutment for maintaining the pair of anchoring devices in position with respect to the impactor.

10. The anchoring system according to claim 9, in which the pair of anchoring devices are retained together by at least one retaining element.

11. The anchoring system according to claim 10, in which the retaining element comprises a ring-shaped body positioned around or in proximity to the posterior end of the pair of anchoring devices.

12. The anchoring system according to claim 11, in which the retaining element comprises an external threading or an internal tapping complementary of another instrument of the system.

13. The anchoring system according to claim 12, wherein each anchoring device of the pair of anchoring devices includes at least one radius of curvature and is positioned one beside the other inside the support, and the pair of anchoring devices are inside the tubular support, in a folded-back position in which their radii of curvature are oriented in different directions, so as to allow deployment towards a deployed position when they are implanted in the bone tissue.

14. The anchoring system according to claim 13, in which the plate of each anchoring device of the pair of anchoring devices comprises at least one housing or a groove able to receive a binding means allowing to bind each anchoring device to the implant.

15. The anchoring system according to claim 14, in which the support and the plate comprise mutual coupling means.

16. The anchoring system according to claim 15, in which the support and the implant comprise mutual coupling means.

* * * * *